US008350007B2

(12) United States Patent
Jennings et al.

(10) Patent No.: US 8,350,007 B2
(45) Date of Patent: Jan. 8, 2013

(54) CRYSTAL STRUCTURE OF HUMAN MITONEET PROTEIN

(75) Inventors: Patricia A Jennings, San Diego, CA (US); Jack Dixon, San Diego, CA (US); Rachel Nechushtai, Motza I'llit (IL)

(73) Assignees: The Regents of the University of California, Oakland, CA (US); Yissum, Research Development Company of Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 12/673,469

(22) PCT Filed: Aug. 15, 2008

(86) PCT No.: PCT/US2008/073366
§ 371 (c)(1),
(2), (4) Date: Jul. 21, 2011

(87) PCT Pub. No.: WO2009/026172
PCT Pub. Date: Feb. 26, 2009

(65) Prior Publication Data
US 2011/0269939 A1    Nov. 3, 2011

Related U.S. Application Data

(60) Provisional application No. 60/965,260, filed on Aug. 17, 2007.

(51) Int. Cl.
*C07K 1/00* (2006.01)
(52) U.S. Cl. ...................................................... 530/350
(58) Field of Classification Search .................. None
See application file for complete search history.

(56) References Cited

U.S. PATENT DOCUMENTS 7,158,888 B2 * 1/2007 McRee et al. ................... 702/19
2002/0165155 A1   11/2002 Schaffer et al.

FOREIGN PATENT DOCUMENTS

WO    WO 94/25026 A1   11/1994
WO    WO 03/093312 A1   11/2003

OTHER PUBLICATIONS

Alfarano et al,. "The Biomolecular Interaction Network Database and related tools 2005 update", Nucleic acids research, 2005; 33: D418-424.
Alizadeh et al., "Distinct types of diffuse large B-cell lymphoma identified by gene expression profiling", Nature, 2000; 403: 503-511.
Allen et al., Acta Oyst. B 1979; 35: 2331.
Bachman et al., "The PIK3CA gene is mutated with high frequency in human breast cancers", Cancer Biol Ther., 2004; 3(8): 772-775.
Bailey S., The CCP4 Suite Programs for protein crystallography, Acta Crystallogr D Biol Crystallogr. 1994; 50(Pt5): 760-763.
Bandyopadhyay et al., "Increased malonyl-CoA levels in muscle from obese and type 2 diabetic subjects lead to decreased fatty acid oxidation and increased lipogenesis; thiazolidinedione treatment reverses these defects", Diabetes, 2006; 55: 2277-2285.
Bedarkar et al., "Relaxin has conformational homology with insulin", Nature, 1977; 270: 449-451.
Beharry et al., "Histidine ligand protonation and redox potential in the rieske dioxygenases: role of a conserved aspartate in anthranilate 1,2-dioxygenase", Biochemistry, 2003, 42: 13625-13636.
Ben-Dor et al., "Tissue classification with gene expression profiles", J Comput Biol., 2000; 7: 559-583.
Blundell et al., "18th Sir Hans Krebs lecture. Knowledge-based protein modelling and design", Eur J Biochem, 1988; 172(3): 513-520.
Blundell et al., "Knowledge-based prediction of protein structures and the design of novel molecules", Nature, 1987; 326(6111): 347-352.
Bogacka et al., "Pioglitazone induces mitochondrial biogenesis in human subcutaneous adipose tissue in vivo", Diabetes, 2005; 54: 1392-1399.
Bowie et al., "A method to identify protein sequences that fold into a known three-dimensional structure", Science, 1991, 253: 164-170.
Burant et al., "Troglitazone Action Is Independent of Adipose Tissue", J Clin Invest 1997; 100: 2900-2908.
Busetta et al., "DOCKER, an interactive program for simulating protein receptor and substrate interactions", J Appl. Crystallogr., 1983; 16(4): 432-437.
Calvano et al., "A network-based analysis of systemic inflammation in humans", Nature, 2005; 437(7061): 1032-1037.
Campbell et al., "Mutation of the PIK3CA gene in ovarian and breast cancer", Cancer Res., 2004; 64: 7678-7681.
Chang et al., "LIBSVM : a library for support vector machines", Software available at http://www.csie.ntu.edu.tw/~cjlin/libsvm (2001).
Chen et al., "Detecting functional modules in the yeast protein-protein interaction network", Bioinformatics, 2006; 22(18): 2283-2290.
Claessens et al., "Modelling the polypeptide backbone with 'spare parts' from known protein structures", Protein Eng, 1989, 2(5): 335-345.
Colca et al., "Identification of a novel mitochondrial protein ("mitoNEET") cross-linked specifically by a thiazolidinedione photoprobe", Am J Physio; Endocrinol. Metab., 2004, 286: E252-E260.
Colca et al., "What has prevented the expansion of insulin sensitizers?", Expert Opin Investig Drugs, 2006; 15: 205-210.
Colca, "Insulin sensitizers may prevent metabolic inflammation", Biochem Pharma., 2006, 72(2): 125-131.
Cosper et al., "Redox-dependent structural changes in archaeal and bacterial Rieske-type [2Fe-2S] clusters", Prot. Sci. 2002, 11(12): 2969-2973.
de Jong et al., "Genes other than BRCA1 and BRCA2 involved in breast cancer susceptibility", J Med Genet., 2002; 39: 225-242.
DeLano et al., Abstr Pap Am Chem Soc. 2005; 230: U1371-U1372.
Doniger et al., "MAPPFinder: using Gene Ontology and GenMAPP to create a global gene-expression profile from microarray data", Genome Biol. 2003; 4: R7.

(Continued)

Primary Examiner — Suzanne M Noakes
Assistant Examiner — Jae W Lee
(74) Attorney, Agent, or Firm — Knobbe, Martens, Olson & Bear, LLP

(57) ABSTRACT

The present technology relates to the fields of crystallography, biochemistry, and drug design. In particular, methods and compositions for screening, identifying and designing compounds that interact with human mitoNEET.

4 Claims, 17 Drawing Sheets

OTHER PUBLICATIONS

Drăghici et al., "Global functional profiling of gene expression", Genomics, 2003; 81(2): 98-104.

Eigenbrot et al., X-ray structure of human relaxin at 1.5 A. Comparison to insulin and implications for receptor binding determinants, J Mol Biol., 1991; 221(1): 15-21.

Ein-Dor et al., "Outcome signature genes in breast cancer: is there a unique set?" Bioinformatics. 2005; 21(2): 171-178.

Ein-Dor et al., "Thousands of samples are needed to generate a robust gene list for predicting outcome in cancer", Proc Natl Acad Sci USA. 2006; 103(15): 5923-5928.

Emsley et al., "Coot: model-building tools for molecular graphics", Acta Crystallogr D Biol Crystallogr, 2004; 60(Pt 12 Pt 1): 2126-2132.

Evans et al., "CHOOCH: a program for deriving anomalous-scattering factors from X-ray fluorescence spectra", J Appl Crystallogr. 2001; 34: 82-86.

Feinstein et al., "Peroxisome proliferator-activated receptor-gamma agonists prevent experimental autoimmune encephalomyelitis.", Ann Neurol, 2002; 51(6): 694-702.

Feinstein et al., "Receptor-independent actions of PPAR thiazolidinedione agonists: Is mitochondrial function the key?", Biochem Pharma., 2005; 70(2): 177-188.

Fish et al., "Purification, crystallization and preliminary X-ray analysis of ferredoxin isolated from thermophilic cyanobacterium *Mastigocladus laminosus*.", Acta Crystallogr D Biol Crystallogr, 2003; 59(Pt 4): 734-6.

Fu et al., "Resonance Raman and magnetic circular dichroism studies of reduced [2Fe-2S] proteins", J Bio Chem., 1992; 267(22): 15502-10.

GO. Gene Ontology Consortium; http://www.geneontology.org/GO.consrtiumlist.shtml/, 2012.

Goebel et al., "An Approximation to the Distribution of Finite Sample Size Mutual Information Estimates", In IEEE Internatioanl Conference on Communications, Seoul, Korea, 2005; 2: 1102-1106.

Golub et al., "Molecular classification of cancer: class discovery and class prediction by gene expression monitoring", Science. 1999; 286(5439): 531-537.

Goodford, "A computational procedure for determining energetically favorable binding sites on biologically important macromolecules" J Med Chem. 1985; 28(7): 849-57.

Grootenhuis et al., Bull. Soc. Chim. Belg. 1992; 101: 661.

Han et al., "Fe2S2 protein resonance Raman spectra revisited: structural variations among adrenodoxin, ferredoxin, and red paramagnetic protein", J. Am. Chem. Soc. 1989, 111(10), 3505-3511.

Han et al., "Vibrational spectra and normal mode analysis for [2Fe-2S] protein analogs using sulfur-34, iron-54 and deuterium substitution . . . ", J Am Chem Soc. 1989; 111(10): 3496-3504.

Hanahan et al., "The hallmarks of cancer", Cell. 2000; 100(1): 57-70.

Heneka et al., "Acute treatment with the PPARgamma agonist pioglitazone and ibuprofen reduces glial inflammation and Abeta1-42 levels in APPV717I transgenic mice.", Brain, 2005; 128(Pt 6): 1442-53.

Hiragun et al., "Preadipocyte differentiation in vitro: identification of a highly active adipogenic agent", J Cell Physiol, 1988; 134(1): 124-30.

Hofmann et al., "New oral thiazolidinedione antidiabetic agents act as insulin-sensitizers", Diabetes Care, 1992; 15(8): 1075-1078.

Holm et al., "Dali: a network tool for protein structure comparison", Trends Biochem Sci. 1995; 20(11): 478-480.

Hou et al., "Crystallographic studies of human MitoNEET", J Biol Chem, 2007; 282(46): 33242-6.

Ideker et al., "Discovering regulatory and signalling circuits in molecular interaction networks", Bioinformatics, 2002; 18(Suppl 1): S233-240.

Iwasaki et al., "Characterization of the pH-dependent resonance Raman transitions of archaeal and bacterial Rieske [2Fe-2S] proteins", J Am Chem Soc., 2004; 126(15): 4788-9.

Iwasaki et al., "Redox-linked ionization of sulredoxin, an archaeal Rieske-type [2Fe-2S] protein from *Sulfolobus* sp. strain 7", J Biol Chem., 1996; 271(44): 27659-63.

Jones et al., "Using known substructures in protein model building and crystallography", EMBO J, 1986, 5(4): 819-822.

Joshi-Tope et al. "Reactome: a knowledgebase of biological pathways", Nucleic Acids Res. 2005; 33: D428-432.

Kanehisa et al., "The KEGG resource for deciphering the genome", Nucleic Acids Res.,2004; 32: D277-280.

Kang et al., "Breast cancer bone metastasis mediated by the Smad tumor suppressor pathway", Proc Natl Acad Sci USA. 2005; 102: 13909-13914.

Kiaei et al., "Peroxisome proliferator-activated receptor-gamma agonist extends survival in transgenic mouse model of amyotrophic lateral sclerosis", Experimental Neurology, 2005, 191(2): 331-336.

Kim et al., "A high-resolution map of active promoters in the human genome", Nature, 2005; 436: 876-880.

Kirkpatrick et al., "Structure-based drug design: combinatorial chemistry and molecular modeling", Comb Chem High Throughput Screen., 1999, 2: 211-221.

Kletzien et al., "Enhancement of adipocyte differentiation by an insulin-sensitizing agent.", Mol Pharmacol, 1992; 41(2): 393-8.

Klingen et al., "Negatively charged residues and hydrogen bonds tune the ligand histidine pKa values of Rieske iron-sulfur proteins", Biochemistry. 2004; 43(39): 12383-12389.

Klotz et al., "Proinflammatory stimulation and pioglitazone treatment regulate peroxisome proliferator-activated receptor gamma levels in peripheral blood mononuclear cells from healthy controls and multiple sclerosis patients.", J Immunol., 2005; 175(8): 4948-55.

Kounosu et al., "Engineering a Three-cysteine, One-histidine Ligand Environment into a New Hyperthermophilic Archaeal Rieske-type [2Fe-2S] Ferredoxin from *Sulfolobus solfataricus*", J Biol Chem., 2004; 279(13): 12519-12528.

Kuila et al., "Resonance Raman spectra of the [2Fe-2S] clusters of the Rieske protein from *Thermus* and phthalate dioxygenase from *Pseudomonas*", J Am Chem Soc., 1987; 109(5): 1559-1561.

Kuila et al., "Resonance Raman studies of Rieske-type proteins," Biochimica et Biophysica Acta (BBA)—Bioenergetics, 1992, 1140(2): 175-183.

Kuntz et al., "A geometric approach to macromolecule-ligand interactions", J Mol Biol., 1982, 161(2): 269-288.

Laskowski et al., "PROCHECK: A program to check the stereochemical quality of protein structures", J. Appl. Crystallogr., 1993, 26(pt2): 283-291.

Lawrence et al., "CLIX: A search algorithm for finding novel ligands capable of binding proteins of known three-dimensional structure", Proteins Struct Funct Genet. 1992; 12(1): 31-41.

Leach et al., "Conformational analysis of flexible ligands in macromolecular receptor", J Comput Chem., 1992; 13(6): 730-748.

Lehmann et al., "An antidiabetic thiazolidinedione is a high affinity ligand for peroxisome proliferator-activated receptor gamma (PPAR gamma)", J Biol Chem, 1995, 270: 12953-12956.

Leslie, AGW, "The integration of macromolecular diffraction data", Acta Crystallogr Section D., 2006; 62: 48-57.

Lewis, Richard A., "Automated site-directed drug design: a method for the generation of general three-dimensional molecular graphs," J Mol Graph. 1992, 10(3): 131-143.

Li et al., "Roles of the mammalian cytosolic cysteine desulfurase, ISCS, and scaffold protein, ISCU, in iron-sulfur cluster assembly", J Biol Chem, 2006; 281(18): 12344-51.

Lill et al., "Mechanisms of iron-sulfur protein maturation in mitochondria, cytosol and nucleus of eukaryotes," Biochim Biophys Acta (BBA), 2006, 1763(7): 652-667.

Lin et al., "Crystal structure of human mitoNEET reveals distinct groups of iron sulfur proteins.", Proc Natl Acad Sci USA, 2007; 104(37): 14640-5.

Lin et al., "Rieske protein from Thermus thermophilus: 15N NMR titration study demonstrates the role of iron-ligated histidines in the pH dependence of the reduction potential", J Amer Chem Soc., 2006; 128(33): 10672-3.

Lovell et al., "Structure validation by Calpha geometry: phi,psi and Cbeta deviation", Proteins, 2003; 50(3): 437-50.

Lüthy et al., "Secondary structure-based profiles: use of structure-conserving scoring tables in searching protein sequence databases for structural similarities", Proteins Struct. Funct. Genet., 1991, 10: 229-239.

Mak et al., "CellCircuits: a database of protein network models", Nucleic Acids Res., 2007; 35: D538-545.

Mansy et al., "Iron-sulfur cluster biosynthesis: toward an understanding of cellular machinery and molecular mechanism", Acc Chem Res, 2004; 37(9): 719-25.

McPhillips et al., "Blu-Ice and the Distributed Control System: software for data acquisition and instrument control at macromolecular crystallography beamlines", J Synchrotron Radiat, 2002; 9(Pt 6): 401-6.

Mendelsohn et al., "Protein interaction methods—toward an endgame", Science. 1999; 284(5422): 1948-1950.

Miranker et al., Functionality Maps of Binding-sites—A Multiple Copy simultaneous Search Method. Proteins: Struct Funct Genet. 1991; 11(1): 29-34.

MSigDB. Molecular Signature Database; http://www.broadinstitute.org/gsea/msigdb/index.jsp, 2012.

Netz et al., "The Cfd1-Nbp35 complex acts as a scaffold for iron-sulfur protein assembly in the yeast cytosol.", Nat Chem Biol, 2007; 3(5): 278-86.

Nikitin et al., "Pathway studio—the analysis and navigation of molecular networks", Bioinformatics. 2003; 19: 2155-2157.

Online Mendelian Inheritance in Man, O.T. McKusick-Nathans Institute for Genetic Medicine, Johns Hopkins University (Baltimore, MD) and National Center for Biotechnology Information, National Library of Medicine (Bethesda, MD), {Jun. 30, 2006}. http://www.ncbi.nlm.nih.gov/omim/.

Overington et al., "Tertiary structural constraints on protein evolutionary diversity: templates, key residues and structure prediction", Proc Biol Sci., 1990; 241(1301): 132-145.

Paddock, et al, MitoNEET is a uniquely folded 2Fe 2S outer mitochondrial membrane protein stabilized by pioglitazone, Proc. Natl. Acad. Sci. U.S.A., 2007, vol. 104, pp. 14342-14347.

Pähler et al., "A probability representation for phase information from multiwavelength anomalous dispersion", Acta Crystallogr. 1990; A 46( Pt 7): 537-540.

Pattabiraman et al. "Computer Graphics in Real-time Docking with Energy Calculation and Minimization", J Comput Chem. 1985; 6: 432.

Pavlidis et al., "Exploring gene expression data with class scores", Pac Symp Biocomput. 2002; 7: 474-485.

Pavlidis et al., "Using the gene ontology for microarray data mining: a comparison of methods and application to age effects in human prefrontal cortex", Neurochem Res. 2004; 29(6): 1213-1222.

Payne et al., "Molecular recognition using a binary genetic search algorithm", J Mol Graphics. 1993; 11(2): 74-91.

Peri et al., "Development of human protein reference database as an initial platform for approaching systems biology in humans", Genome Res. 2003; 13(10): 2363-2371.

Pershadsingh et al., "Effect of pioglitazone treatment in a patient with secondary multiple sclerosis," J. Neuroinflammation, 2004; 1(1):3.

Perrakis et al., "Automated protein model building combined with iterative structure refinement.", Nat Struct Biol. 1999; 6(5): 458-463.

Petricoin et al. "Mapping molecular networks using proteomics: a vision for patient-tailored combination therapy", J Clin Oncol. 2005; 23: 3614-3621.

Presnell et al., "A segment-based approach to protein secondary structure prediction.", Biochem. 1992; 31(4): 983-93.

Ramani et al., "Consolidating the set of known human protein-protein interactions in preparation for large-scale mapping of the human interactome", Genome Biol. 2005; 6(5): R40.1-R40-12.

Ramaswamy et al., "A molecular signature of metastasis in primary solid tumors", Nat Genet. 2003; 33(1): 49-54.

Ramelot et al., "Solution NMR Structure of the Iron-Sulfur Cluster Assembly Protein U (IscU) with Zinc Bound at the Active Site," J Mol Biol., 2004; 344(2): 567-583.

Rapaport et al., "Classification of microarray data using gene networks", BMC Bioinformatics. 2007; 8: 35 (pp. 15).

Roglic et al. "The burden of mortality attributable to diabetes: realistic estimates for the year 2000", Diabetes Care 2005; 28(9): 2130-2135.

Rose et al., "Investigation of the Electronic Structure of 2Fe__2S Model Complexes and the Rieske Protein Using Ligand K-Edge W-ray Absorption Spectroscopy", J Am Chem Soc. 1999; 121(11): 2353-2363.

Rotsaert et al., "N-isotope effects on the Raman spectra of Fe(2)S(2) ferredoxin and Rieske ferredoxin: evidence for structural rigidity of metal sites", J Biol Inorg Chem, 2003; 8(3): 318-26.

Rotstein et al., "GenStar: a method for de novo drug design", J Comput Aided Mol Des. 1993; 7(1): 23-43.

Rotstein et al., "GroupBuild: a fragment-based method for de novo drug design.", J Med Chem, 1993; 36(12): 1700-10.

Rual et al., "Towards a proteome-scale map of the human protein-protein interaction network", Nature. 2005; 437: 1173-1178.

Rusinko et al., "Using CONCORD to construct a large database of three-dimensional coordinates from connection", J Chem Inf Comput Sci. 1989; 29(4): 251-255.

Sali et al., "Definition of general topological equivalence in protein structures. A procedure involving comparison of properties and relationships through simulated annealing and dynamic programming", J. Mol. Biol., 1990, 212(2): 403-428.

Saltiel, A.R., New perspectives into the molecular pathogenesis and treatment of type 2 diabetes, Cell, 2001, 104: 517-529.

Schütz et al, "The Oral Antidiabetic Pioglitazone Protects from Neurodegeneration and Amyotrophic Lateral Sclerosis-Like Symptoms in Superoxide Dismutase-G93A Transgenic Mice,", J. Neurosci. 25(34): 7805-7812, 2005.

Segal et al., "Module networks: identifying regulatory modules and their condition-specific regulators from gene expression data", Nat Genet. 2003; 34(2): 166-176.

Sharan et al., "Conserved patterns of protein interaction in multiple species",. Proc Natl Acad Sci USA. 2005; 102(6): 1974-1979.

Sjöblom et al., "The Consensus Coding Sequences of Human Breast and Colorectal Cancers", Science 2006; 314(5797): 268-274.

Sparks et al, "Antidiabetic AD4743 enhances adipocyte differentiation of 3T3 T mesenchymal stem cells.", J Cell Physiol, 1991; 146(1): 101-9.

Spiegelman B. M., "PPAR-γ: Adipogenic Regulator and Thiazolidinedione Receptor", Diabetes. 1998; 47: 507-514.

Spiro et al, "Biological Applications of Raman Spectroscopy," 1988, John Wiley & Sons (Spiro T.G. ed) 3: 1-37 & 523-553.

Srinivasan et al., "An evaluation of the performance of an automated procedure for comparative modelling of protein tertiary structure." Protein Eng. 1993; 6(5): 501-12.

Stark et al., ESCI Award 2006. Mitochondrial function and endocrine diseases, Eur. J. Clin. Invest., 2007, 37(4): 236-248.

Stelzl et al., "A human protein-protein interaction network: a resource for annotating the proteome", Cell. 2005; 122(6): 957-968.

Storici et al., "Structures of gamma-aminobutyric acid (GABA) aminotransferase, a pyridoxal 5'-phosphate, and [2Fe-2S] cluster-containing enzyme, complexed with gamma-ethynyl-GABA and with the antiepilepsy drug vigabatrin.", J Biol Chem, 2004; 279(1): 363-73.

Subramanian et al., "Gene set enrichment analysis: a knowledge-based approach for interpreting genome-wide expression profiles", Proc Natl Acad Sci USA. 2005; 102: 15545-15550.

Summers et al., Analysis of side-chain orientations in homologous proteins, J Mol Biol, 1987, 196(1): 175-198.

Sutcliffe et al, "Knowledge based modelling of homologous proteins, Part II: Rules for the conformations of substituted sidechains", Protein Eng, 1987, 1(5): 385-392.

Sutcliffe et al., "Knowledge based modelling of homologous proteins, Part I: Three-dimensional frameworks derived from the simultaneous superposition of multiple structures", Protein Eng, 1987, 1(5): 377-384.

Swets et al., J. Psychological Science Can Improve Diagnostic Decisions. Psychological Science in the Public Interest. 2000; 1(1): 1-26.

Symmans et al., "Breast cancer heterogeneity: evaluation of clonality in primary and metastatic lesions", Hum Pathol. 1995; 26(2): 210-216.

Takeda Pharmaceutical Company Limited; Pioglitazone/Metformin Fixed-Dose Combination Product, 1.14 Labelin—Revised Proposed Patient Information Sheet; Aug. 8, 2005; http://www.fda.gov/cder/foi/label/2005/021842lbl.pdf; pp.

Tang et al., "Resonance Raman scattering and optical absorption of adrenodoxin and selena-adrenodoxin", Biochem Biophys Res Comm. 1973; 53(3): 869-874.

Terwilliger et al., "Automated MAD and MIR structure solution", Acta Cryst. 1999; D55: 849-861.

Terwilliger, TC, "Maximum-likelihood Density Modifaction.", Acta Crystallogr D Biol Crystallogr, 2000; 56(Pt 8): 965-72.

Tian et al., "Discovering statistically significant pathways in expression profiling studies", Proc Natl Acad Sci USA. 2005; 102: 13544-13549.

Tomioka et al., "A Method for Fast Energy Estimation and Visualization of Protein-Ligand Interaction", J Comp Molec. Design, 1987; 1(3): 197-210.

Tomlins et al., "Recurrent fusion of TMPRSS2 and ETS transcription factor genes in prostate cancer", Science. 2005; 310: 644-648.

Topham et al, "An assessment of COMPOSER: a rule-based approach to modelling protein structure", Biochem. Soc. Symp, 1990, 57: 1-9.

Topham et al., "Fragment ranking in modelling of protein structure. Conformationally constrained environmental amino acid substitution tables," Journal of Molecular Biology, 1993, 229(1):194-220.

Tourassi et al., "Application of the mutual information criterion for feature selection in computer-aided diagnosis", Medical Physics. 2001; 28(12): 2394-2402.

Turner et al., "Hallmarks of 'BRCAness' in sporadic cancers", Nat Rev Cancer. 2004; 4(10): 814-819.

van de Vijver et al., "A gene-expression signature as a predictor of survival in breast cancer", N Engl J Med. 2002; 347(25): 1999-2009.

van't Veer et al., "Gene expression profiling predicts clinical outcome of breast cancer", Nature. 2002; 415: 530-536.

Vriend, G. "What If: a molecular modeling and drug design program.", J Mol Graph, Mar. 1990; 8(1):52-56.

Wang et al., "Gene-expression profiles to predict distant metastasis of lymph-node-negative primary breast cancer", Lancet. 2005; 365: 671-679.

Wei et al., "A Markov Random Field Model for Network-based Analysis of Genomic Data", Bioinformatics. 2007; 23(12): 1537-1544.

Weigelt et al., "Breast cancer metastasis: markers and models", Nat Rev Cancer. 2005; 5(8): 591-602.

Whittle et al., Protein structure—based drug design, Annu. Rev. Biophys. Biomol. Struct., 1994, 23: 349-375.

Wiley, et al, MitoNEET is an iron-containing outer mitochondrial membrane protein that regulates oxidative capacity, Proc Natl Acad Sci U S A, 2007, 104(13): 5318-5323.

Wiley, et al, The outer mitochondrial membrane protein mitoNEET contains a novel redox-active 2Fe-2S cluster, J. Biol. Chem., 2007, 282(33): 23745-23749.

Williams et al, Diabetes. 1993; 42 (Supplement 1):, 59A.

Winn et al, "Macromolecular TLS Refinement in REFMAC at Moderate Resolutions,", Methods in Enzymology, Academic Press, 2003, vol. 374, Macromolecular Crystallography, Part D, pp. 300-321.

Wodak et al., Computer analysis of protein-protein interaction, J Mol Biol., 1978; 124(2): 323-342.

Yachandra et al., "Resonance Raman spectra of spinach ferredoxin and adrenodoxin and of analog complexes", J Am Chem Soc. 1983; 105: 6462-6468.

Yang et al, "Automated and accurate deposition of structures solved by X-ray diffraction to the Protein Data Bank.", Acta Crystallogr D Biol Crystallogr, Oct. 2004; 60(Pt 10):1833-9.

Yue, et al, "The determination of the pKa of histidine residues in proteins by Raman difference spectroscopy.", Biochim Biophys Acta, 1991; 1078(2):296-302.

International Search Report and Written Opinion dated Mar. 5, 2009 in PCT/US08/073366, filed Aug. 15, 2008.

International Preliminary Report on Patentability dated Mar. 5, 2009 in PCT/US08/073366, filed Aug. 15, 2008.

* cited by examiner

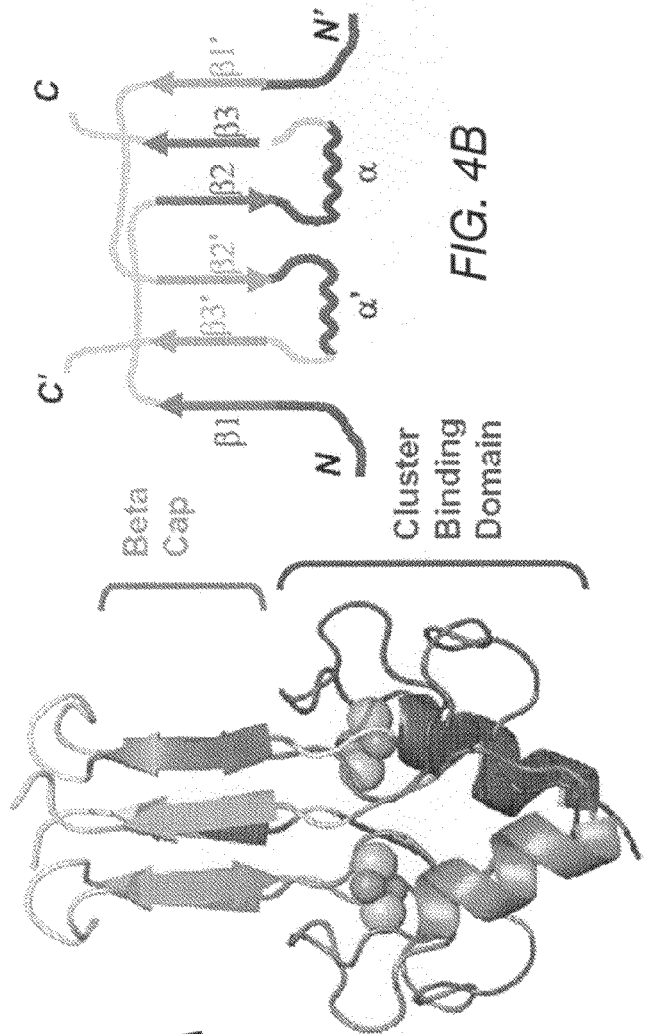
FIG. 4A
FIG. 4B
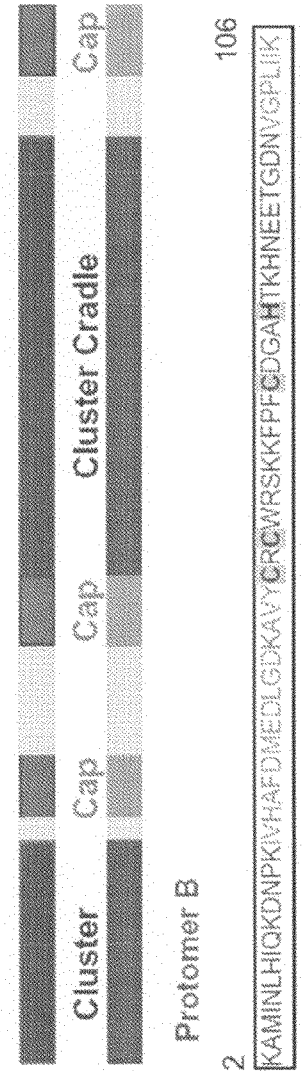
FIG. 4C

FIG. 5C
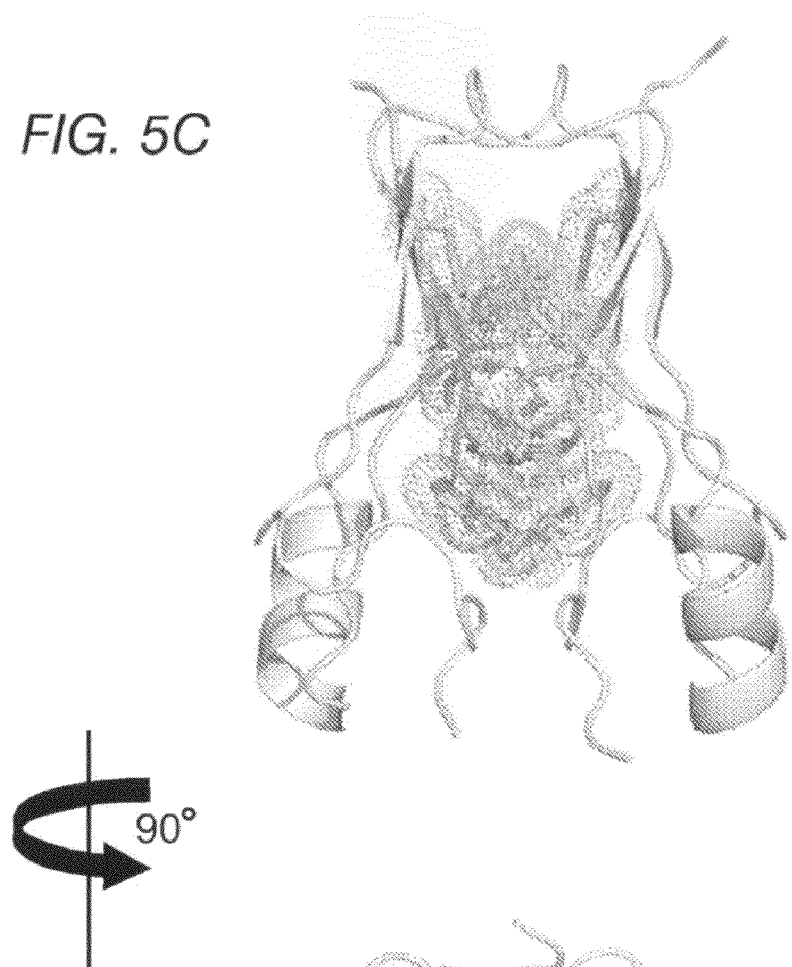
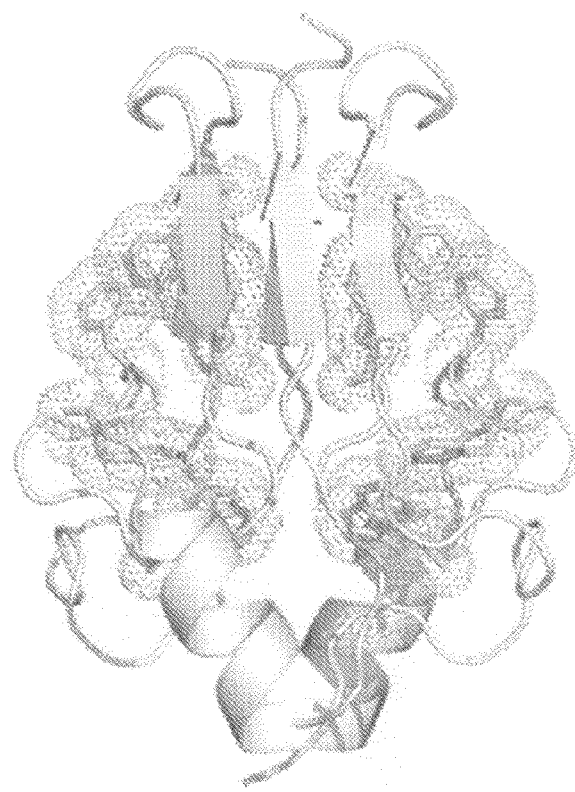
FIG. 5D

SEQUENCE LISTING

```
<160> NUMBER OF SEQ ID NOS: 2

<210> SEQ ID NO 1
<211> LENGTH: 76
<212> TYPE: PRT
<213> ORGANISM: Homo Sapiens

<400> SEQUENCE: 1

Arg Phe Tyr Val Lys Asp His Arg Asn Lys Ala Met Ile Asn Leu His
  1               5                  10                  15

Ile Gln Lys Asp Asn Pro Lys Ile Val His Ala Phe Asp Met Glu Asp
             20                  25                  30

Leu Gly Asp Lys Ala Val Tyr Cys Arg Cys Trp Arg Ser Lys Lys Phe
         35                  40                  45

Pro Phe Cys Asp Gly Ala His Thr Lys His Asn Glu Glu Thr Gly Asp
     50                  55                  60

Asn Val Gly Pro Leu Ile Ile Lys Lys Lys Glu Thr
 65                  70                  75

<210> SEQ ID NO 2
<211> LENGTH: 9
<212> TYPE: PRT
<213> ORGANISM: Homo Sapiens

<400> SEQUENCE: 2

Ala His Thr Lys His Asn Glu Glu Thr
  1               5
```

CRYSTAL STRUCTURE OF HUMAN MITONEET PROTEIN

CROSS-REFERENCE TO RELATED APPLICATIONS

This application is the U.S. National Phase under 35 U.S.C. §371 of International Application No. PCT/US2008/073366, filed Aug. 15, 2008 under the Patent Cooperation Treaty (PCT), which was published by the International Bureau on Feb. 26, 2009 in English, which designates the United States and claims priority to U.S. Provisional Application 60/965,260 entitled "NEW APPROACH FOR DESIGNING DIABETES DRUGS" and filed on Aug. 17, 2007, the disclosures of which are hereby incorporated herein by reference in their entireties for any purpose.

STATEMENT REGARDING FEDERALLY SPONSORED R&D

This invention was made with government support under NIH Grant/Contract Numbers GM41637, GM54038, DK54441, GM18024 and GM18849 awarded by the National Institutes of Health of the United States of America. The government has certain rights in the invention.

REFERENCE TO SEQUENCE LISTING

The present application is being filed along with a Sequence Listing in electronic format. The Sequence Listing is provided as a file entitled UCSD018.001.TXT, created Aug. 14, 2008, which is 1.22 KB in size. The information in the electronic format of the Sequence Listing is incorporated herein by reference in its entirety.

FIELD OF THE INVENTION

The present technology relates to the fields of crystallography, biochemistry, and drug design. In particular, the present technology relates to methods and compositions for screening, identifying and designing compounds that interact with human mitoNEET.

BACKGROUND

Diabetes is the fifth most common cause of death and was responsible for over 5% of worldwide deaths in 2000 (Roglic, G.: Unwin, N.; Bennett, P. H.; Mathers, C.; Tuomilehto, J.; Nag, S.; Connelly, V.; King, H; *Diabetes Care* 2005, 28, 2130-2135). Type II Diabetes is characterized by insulin resistance of the peripheral tissues, including the skeletal muscle, liver, and adipose. The resulting hyperglycemia is often accompanied by defective lipid metabolism that can lead to cardiovascular complications such as atherosclerosis and hypertension. Accordingly, it often leads to serious complications such as renal disease, blindness, heart disease and stroke, and the treatment of diabetes annually incurs nearly 100 billion dollars of medical costs in the United States alone (Saltiel, A. R.; *Cell* 2001, 104, 517-529).

The most broadly successful class of drugs used to treat type II diabetes is the thiazolidinediones (TZDs), some examples of which are pioglitazone and rosiglitazone (trade names Actos and Avandia, respectively). The antidiabetic activity of TZDs was first elucidated in the 1970s, where they were first identified as high affinity ligands for the nuclear transcription factor peroxisome proliferator-activated receptor gamma (PPARγ) (Colca, J. R.; Kletzien, R. F.; *Expert Opin. Invest. Drugs* 2006, 15, 205-210, Lehmann, J. M.; Moore, L. B.; Smitholiver, T. A.; Wilkison, W. O.; Willson, T. M.; Kliewer, S. A., *J. Biol. Chem.* 1995, 270, 12953-12956).

However, the link between TZDs, PPARγ, and antidiabetic benefits came into question and ultimately led to the identification of a previously unknown outer mitochondrial membrane protein that directly binds to TZDs (Colca, J. R.; Kletzien, R. F., *Expert Opin. Invest.; Drugs* 2006, 15, 205-210, Also known as CISD1 (CDGSH Iron Sulfur Domain 1), ZCD1, C10orf70, MGC14684, MDS029, Colca, J. R.; McDonald, W. G.; Waldon, D. J.; Leone J. W.; Lull, J. M.; Bannow, C. A.; Lund, E. T.; Mathews, W. R., *Am. J. Physio.; Endocrinol. Metab.* 2004, 286, E252-E260). The outer mitochondrial membrane protein was named mitoNEET based on its subcellular localization (mito) and the presence of the amino acid sequence Asn-Glu-Glu-Thr (NEET).

MitoNEET is an integral protein of the outer mitochondrial membrane (OMM), as shown by immuno-electron microscopy and fractionation of highly purified rat liver mitochondria. An amino terminal signal sequence within the first 32 residues, containing a predicted transmembrane domain, targets mitoNEET to the outer membrane. The orientation of mitoNEET towards the cytoplasm was established by proteolytic digestion of the protein on intact rat liver mitochondria.

Mitochondrial dysfunction has been further associated with insulin resistance and the development of type II diabetes (Stark, R. & Roden, M. (2007) *Eur. Clin. Invest.* 37, 236-248). Some studies indicate that disease pathogenesis involves diminished mitochondrial oxidative capacity in insulin sensitive tissues, and agents, such as TZDs, are known to enhance oxidative capacity and normalize lipid metabolism (Bandyopadhyay, G K, Yu, J G, Ofrecio, J, & Olefsky, J M (2006) *Diabetes* 55, 2277-2285; Bogacka, I, Xie, H, Bray, G A, & Smith, S R (2005) *Diabetes* 54, 1392-1399). Moreover, deficiency of mitoNEET in mice results in a compromise in the respiratory capacity of heart mitochondria (Wiley, S E, Murphy, A N, Ross, S A, van der Geer, P, & Dixon, J E (2007) *PNAS* 104, 5318-5323). Accordingly, mitoNEET is a candidate target for drugs to treat several disorders including type II diabetes.

SUMMARY

Some embodiments relate to a crystal containing a human mitoNEET protein, in which the crystal effectively diffracts X-rays for the determination of the atomic coordinates of the mitoNEET protein to a resolution of greater than about 1.5 Å. In some such embodiments, the human mitoNEET protein includes SEQ ID NO: 1, or an amino acid sequence having at least 85% amino acid identity to the polypeptide of SEQ ID NO: 1.

In more embodiments, a crystal can have an orthorhombic space group P212121 and unit cell dimensions of about a=46.8 Å, b=49.6 Å, and c=59.0 Å. In even more embodiments, a crystal can have a three dimensional structure characterized by the atomic coordinates of Table 2. In certain embodiments, a crystal can contain a human mitoNEET protein having tertiary structure containing a NEET fold. In exemplary embodiments, a crystal can contain a truncated human mitoNEET protein.

Some methods relate to methods for designing a compound that binds human mitoNEET protein with steps that can include: accessing at least a portion of the data of Table 2; and modeling the binding of the compound to human mitoNEET utilizing the data. In more methods, the modeling further includes predicting the likelihood of the compound increasing 2Fe-2S cluster stability in a human mitoNEET protein. More embodiments include methods further including testing the stability of the 2Fe-2S cluster in the presence of the compound.

In some methods the compound is designed de novo. In other embodiments, the compound is designed from a known chemical entity or a fragment thereof. In some such methods, the known chemical entity or a fragment thereof includes a thiazolidinedione. In further embodiments, the thiazolidinedione is selected from the group consisting of pioglitazone, troglitazone, rivoglitazone, and rosiglitazone.

Some embodiments relate to methods for identifying a compound for use in the treatment of a mitoNEET-associated disorder that include the steps of accessing at least a portion of the data of Table 2; and modeling the binding of the compound to human mitoNEET utilizing the data, in which the mitoNEET-associated disorder is selected from the group consisting of type II diabetes, insulin resistance, multiple sclerosis, Alzheimer's disease, and amyotrophic lateral sclerosis.

Some embodiments relate to compounds identified by accessing at least a portion of the data of Table 2; and modeling the binding of the compound to human mitoNEET utilizing the data.

More embodiments relate to computer readable media containing the atomic coordinates of Table 2. Even more embodiments relate to methods for using computer readable media containing the atomic coordinates of Table 2 with steps that include: loading the co-ordinates of Table 2 into memory; processing the co-ordinates to create a three dimensional representation; and displaying the three dimensional representation on a display.

Some embodiments relate to methods for screening for an agent that modulates 2Fe-2S cluster stability in mitoNEET with steps that include: selecting or designing a candidate agent by performing structure based drug design with a computer system encoded with computer readable data containing atomic coordinate data or binding site data or both, in which the selecting step is performed in conjunction with computer modeling; contacting the candidate agent with mitoNEET; and detecting the ability of the candidate agent to modulate 2Fe-2S cluster stability.

Certain embodiments relate to methods for identifying a compound which stabilizes the 2Fe-2S cluster with one or more steps that include comparing the stability of said 2Fe-2S cluster in the presence and absence of said compound. In some such methods, the stability is measured in vitro, and in particular, using spectroscopic methods.

BRIEF DESCRIPTION OF THE DRAWINGS

FIG. 4 shows schematic views of the primary, secondary and tertiary structure of mitoNEET. FIG. 4A shows a ribbon diagram of mitoNEET. FIG. 4B depicts secondary structure of mitoNEET. FIG. 4C shows the primary structure of mitoNEET with regions corresponding to regions depicted in FIG. 4A. The primary structure shown in FIG. 4C corresponds to positions SEQ ID: 1, positions 10-74.

FIG. 5 shows ribbon diagrams of mitoNEET. FIGS. 5C and 5D show ribbon diagrams of mitoNEET with aromatic residues emphasized with a contoured cloud over the backbone of each protomer.

FIG. 6 shows schematic views of the 2Fe-2S cluster binding cradle.

FIGS. 12A-C show resonance Raman spectra for native mitoNEET at pH values of 7.5, 7.0, and 6.2, respectively. FIGS. 12 D-F show resonance Raman spectra for mutant H87C mitoNEET at pH values of 7.5, 7.0, and 6.2, respectively. Grey curves are Raman data. Solid-filled curves are the Gaussian decompositions, with the black-dashed lines are the sum of Gaussian decompositions. Peak positions are identified from the decompositions.

DETAILED DESCRIPTION

The present technology relates to methods and compositions for screening, identifying, and designing compounds that interact with mitoNEET. Such methods include identifying compounds that can be useful to treat metabolic dysfunctional disorders, such as type II diabetes. More methods can include screening, identifying, and designing compounds that stabilize the 2Fe-2S cluster of mitoNEET.

Iron sulfur (Fe—S) proteins are key players in vital processes involving energy homeostasis and metabolism from the simplest to most complex organisms. Described herein is a 1.5 Å X-ray crystal structure of mitoNEET, an outer mitochondrial membrane Fe—S protein.

Figure 1:
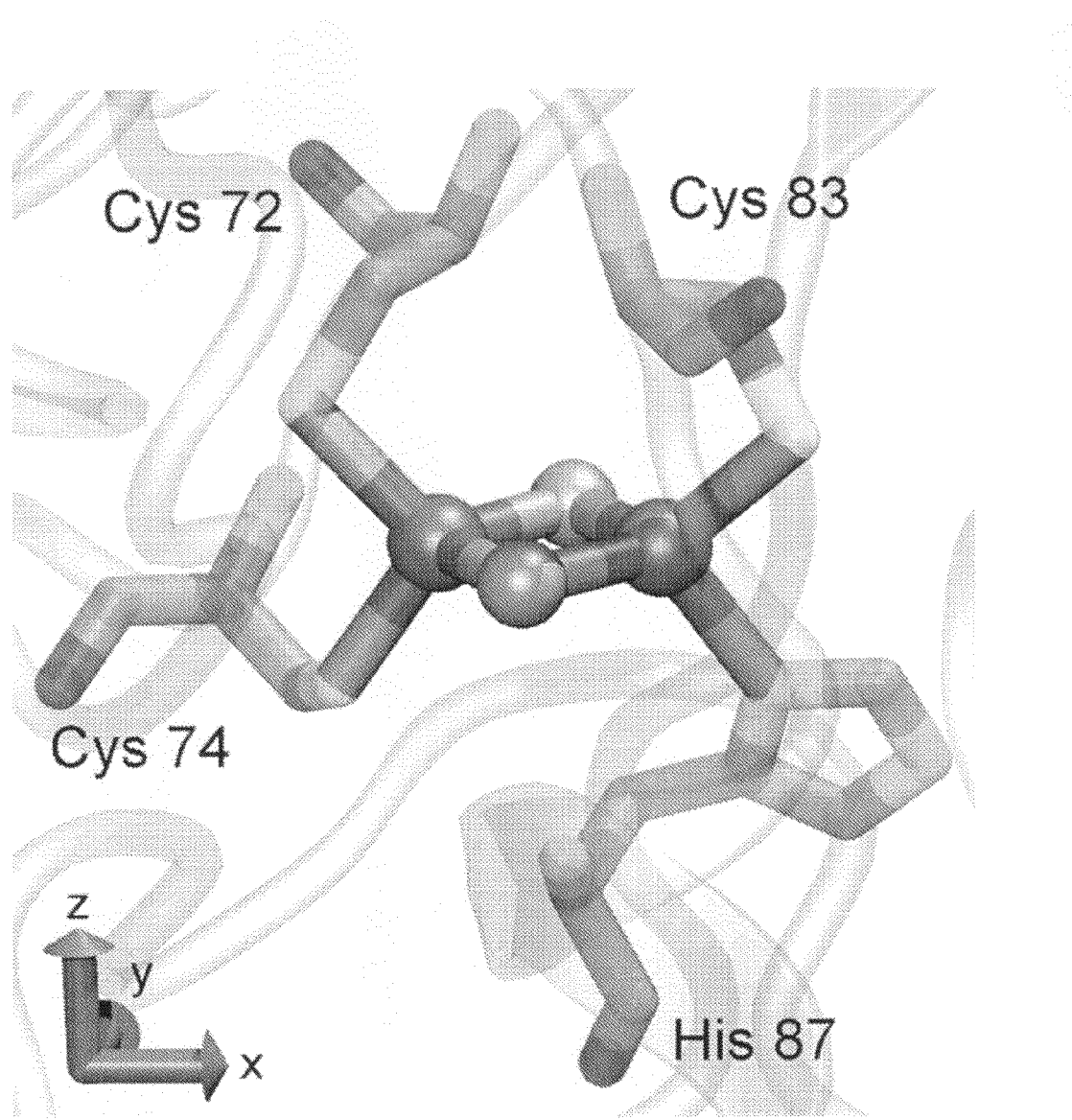
FIG. 1 shows a cluster binding domain of mitoNEET containing 3 cysteine residues and 1 histidine residue, coordinating an acid-labile 2Fe-2S cluster.

The mitoNEET protein is composed of two protomers intertwined to form a dimeric structure that contains a NEET fold. The protomers form a two-domain structure with a beta cap domain and a cluster binding domain. The cluster binding domain is composed of 3 cysteine residues and 1 histidine residue, and coordinates two acid-labile 2Fe-2S clusters (FIG. 1). This domain is unique among 2Fe-2S cluster binding proteins, which have previously been observed primarily with 4(Cys) or 2(Cys)2(His) ligation environments, referred to as ferredoxins and Rieske-type proteins, respectively.

The biophysical properties of mitoNEET suggest that it may play a role in metal-cluster transfer or electron transfer reactions (Paddock, M. L.; Wiley, S. E.; Axelrod, H. L.; Cohen, A. E.; Roy, M.; Abresch, E. C.; Capraro, D.; Murphy, A. N.; Nechushtai, R.; Dixon, J. E.; Jennings, P. A.; *Proc. Natl. Acad. Sci. U.S.A.* 2007, 104, 14342-14347). In both cases, the protonation state of the ligating histidine residue is significant because the cationic form of the residue at low pH likely facilitates release of the metal cluster and different protonation states may tune the redox potential (Beharry, Z. M.; Eby, D. M.; Couter, E. D.; Viswanathan, R.; Neidle, E. L.; Phillips, R. S.; Kurtz, D. M.; *Biochemistry* 2003 42, 13625-13636).

Initial spectroscopic work has been performed on mitoNEET using techniques such as visible absorption, NMR, EPR, and mass spectrometry (Paddock, M. L.; Wiley, S. E.; Axelrod, H. L.; Cohen, A. E.; Roy, M.; Abresch, E. C.; Capraro, D.; Murphy, A. N.; Nechushtai, R.; Dixon, J. E.; Jennings, P. A.; *Proc. Natl. Acad. Sci. U.S.A.* 2007, 104, 14342-14347; Wiley, S. E.; Paddock, M. L.; Abresch, E. C.; Gross L.; van der Geer, P.; Nechushtai, R.; Murphy A. N.; Jennings, P. A.; Dixon J. E.; *J. Biol. Chem.* 2007, 282, 23745-23749). The absorption spectrum of mitoNEET has a peak near 460 nm attributed to the 2Fe-2S cluster that is reversibly reduced by dithionite and oxygen. The cluster is labile at pH≦8.0 as shown by the loss of the spectral signature and of the 2Fe and 2S as shown by mass spectroscopy (Wiley, S E, Paddock, M L, Abresch, E C, Gross, L, van der Geer, P, Nechushtai, R, Murphy, A N, Jennings, P A, & Dixon, J E (2007) J Biol. Chem., 282 (33): 23745-9).

The mitoNEET protein interacts with pioglitazone, a member of the TZD family of compounds. TZDs have been used to treat disorders including type II diabetes. As described further herein, binding of pioglitazone, stabilizes mitoNEET against 2Fe-2S cluster release. Without wishing to be bound to any one theory, such stabilization may be a mechanism by which compounds such as TZDs can have a therapeutic effect. However, stabilization of the 2Fe-2S cluster in mitoNEET may be one of several effects that compounds such as TZDs can have on mitoNEET.

The following description includes methods and compositions for screening, identifying, and designing compounds that interact with mitoNEET.

MitoNEET Crystals

Some embodiments disclosed herein relate to crystals of mitoNEET. The crystals can contain a structure that can be characterized as a NEET fold. An example of preparing crystals can be found in Example 1.

In some embodiments a crystal can contain the human mitoNEET protein in which the crystal can be used to diffract X-rays to determine the atomic coordinates of the mitoNEET protein to a resolution less than about 5 Å, less than about 2 Å, less than about 1.5 Å, less than about 1 Angstrom. In such embodiments, the human mitoNEET protein can comprise a polypeptide with at least 50%, at least 60%, at least 65%, at least 70%, at least 75%, at least 80%, at least 85%, at least 90%, at least 95%, and at least 99%, identity to SEQ ID No.: 1. In more embodiments, a mitoNEET crystal can comprise a polypeptide with 100% identity to SEQ ID No.: 1. In more embodiments, the polypeptide can contain insertions, deletions, and/or mutations.

MitoNEET X-Ray Crystallography Data

Some embodiments relate to methods utilizing data obtained from mitoNEET crystals. Specific details of crystallographic analysis can be found in Example 1. A summary of crystal parameters for an exemplary mitoNEET polypeptide can be found in Example 1, Table 1; crystal coordinates are provided in Table 2. Table 2 contains header information describing the structure determination in rows beginning with ""REMARK," "CISPEP," and "SCALE." Subsequent to these headers, Column 1 indicates the presence of an atom, Column 2 shows the serial number or atom number, Column 3 the atom name, Column 4 the residue name and polypeptide chain A or polypeptide chain B, Column 5 the residue number, Column 6 the X coordinate, Column 7 the Y coordinate, Column 8 the Z coordinate, Column 9 the atomic occupancy, Column 10 the temperature factor, and Column 11 the chain ID. Figures were generated using the X-ray crystallographic data, including FIGS. 1, 2, 3A-C, 4A-F, and 5A-B.

The crystal coordinates shown in Table 2 provide a measure of atomic location in Å. The coordinates are a relative set of positions that define a shape in three dimensions. An entirely different set of coordinates having a different origin and/or axes may define a similar or identical shape. However, varying the relative atomic positions of the atoms of the structure so that the root mean square deviation of the conserved residue backbone atoms, namely, the nitrogen-carbon-carbon backbone atoms of the protein amino acid residues, is less than 1.5 Å, when superimposed on the coordinates provided in Table 2 for the conserved residue backbone atoms, may generally result in structures which are substantially the same as the structure defined by Table 2 in terms of both its structural characteristics and its usefulness for structure-based drug design. Thus, in some embodiments the coordinates of Table 2 can be transposed to a different origin and/or axes; the relative atomic positions of the atoms of the structure are varied so that the root mean square deviation of conserved residue backbone atoms is less than 1.5 Å, when superimposed on the coordinates provided in Table 2 for the conserved residue backbone atoms; and/or the number and/or positions of water molecules is varied. References herein to the coordinates of Table 2, thus includes the coordinates in which one or more individual values of the Table 2 are varied in this way.

Modifications in the mitoNEET crystal structure due to, for example, mutations, additions, conservative and non-conservative substitutions, and/or deletions of amino acid residues may account for variations in the mitoNEET atomic coordinates.

Identifying Compounds in Silico

Some embodiments described herein relate to methods for screening, identifying and/or designing compounds that interact with mitoNEET. Such methods can include the step of accessing any portion of the data contained in Table 2, and modeling one or more compounds using that data. The modeling can include, for example, predicting the interactions between a compound and the mitoNEET protein. More exemplary embodiments can include predicting the interactions between a compound and a modified mitoNEET protein. The modified mitoNEET protein can be modified with one or more insertions, deletions and/or mutations. Even more exemplary embodiments can include predicting the interactions between the mitoNEET protein and a TZD, such as pioglitazone, rosiglitazone, troglitazone, ciglitazone, or rivoglitazone. Even more exemplary embodiments can include predicting the likelihood of a compound increasing the stability of the 2Fe-2S cluster of mitoNEET.

Some embodiments include designing compounds using techniques of structure-based drug design. Structure-based drug design involves the rational design of ligand molecules to interact with the three-dimensional (3-D) structure of target receptors; the ultimate goal being to identify or design molecules with 3-D complementarity to the target protein, namely, mitoNEET (Kirkpatrick et al. (1999) Comb. Chem. High Throughput Screen. 2: 211-21). The accuracy required of a protein structure depends on the question addressed by the design process, with some processes predicated on the assumption that a lead molecule will need to complement a known binding site for a ligand precisely, or match the presumed transition state structure of a reaction closely (Whittle and Blundell (1994) Annu. Rev. Biophys. Biomol. Struct. 23: 349-75). Such cases call for an accurate model at the highest resolution possible. Alternatively, the design process may exploit the structure to indicate the general availability of space to fill, hydrogen bonds to make, or electrostatic interactions to optimize, in which case knowledge of the general topography of the binding site is often useful (Whittle and Blundell (1994) Annu. Rev. Biophys. Biomol. Struct. 23: 349-75).

Factors that affect the accuracy of structure-based drug design include aspects of the determination of the 3-D structure of proteins such as refinement, resolution, the number of restraints introduced in the structure analysis, statistical indicators of agreement between the model and the experimental data, and the conformity of the model to stereochemistry found in proteins in general (Whittle and Blundell (1994) Annu. Rev. Biophys. Biomol. Struct. 23: 349-75).

Most statistical parameters can be optimized, at least within the constraints of the data. However, if the data is of poor quality or the conformations are incorrect, particularly for the sidechains and loops, then it is difficult to optimize all of the parameters at the same time (Whittle and Blundell (1994) Annu. Rev. Biophys. Biomol. Struct. 23: 349-75). Computer programs are available to introduce a check on such parameters, including PROCHECK™, which analyzes the distribution of a range of conformational parameters and compares them with expected distributions (Laskowski et al. (1993). J Appl. Crystallogr. 26:283).

Sequence-dependent indications of the probability that the structure is correct can be derived through a comparison of the local environment in the proposed structure to the propensity of an amino acid (Luthy et al. (1991) Proteins Struct. Funct. Genet. 10: 229; Novotny et al. (1988) Proteins Struct. Funct. Genet. 4: 19), the knowledge-based potential (Hendlich et al. (1990) J Mol. Biol. 216: 167), or the probability of amino acid substitution (Overington et al. (1990) Proc. R. Soc. London Ser. B 241: 132; Topham et al. (1991) Biochem. Soc. Syrup. 57: 1) in the proposed structure.

Protein structures cannot generally be predicted by simulation of the folding pathway due to the fact that the forces between the atoms of the protein, and particularly with the surrounding solvent and counter-ions, are not well described (Whittle and Blundell (1994) Annu. Rev. Biophys. Biomol. Struct. 23: 349-75). However, some proteins belong to families with a common fold, including more than 1500 groups of homologous proteins that can be recognized by sequence searches alone, and over 500 that have common topologies or folds (Whittle and Blundell (1994) Annu. Rev. Biophys. Biomol. Struct. 23: 349-75).

Profiles or templates are useful in the search for the common fold and alignment of sequences for proteins with sequence identities of <30% (Whittle and Blundell (1994) Annu. Rev. Biophys. Biomol. Struct. 23: 349-75). Structural information can be used to identify key features in protein architecture and then to associate these with invariant or conserved sequences (Bedarkar et al. (1977) Nature 270: 449; Eigenbrot et al. (1991) J. Mol. Biol. 221; 15). Projection of the restraints of the 3-D fold onto the one dimension of the sequence and comparison to sequence templates or profiles provides a more systematic approach (Sali et al. (1990) J. Mol. Biol. 212: 403).

The template search can also be approached by determining the propensity of an amino acid to occur in each class of local structural environment defined by solvent accessibility and secondary structure, or by calculation of amino acid substitution tables as a function of local environment (Bowie et al. (1991) Science 253: 164; Johnson et al. (1993) J. Mol. Biol. 231: 735; Luthy et al. (1991) Proteins Struct. Funct. Genet. 10: 229; Overington et al. (1990) Proc. R. Soc. London Ser. B 241: 132).

The 3-D structure of a protein can also be predicted by using information derived from the identification of a new sequence with a known fold (Summers et al. (1987) J. Mol. Biol. 196: 175; Sutcliffe et al. (1987) Protein Eng. 1: 385). Some methods depend on the assembly of rigid fragments to select sets of fragments that define the framework: the structurally variable (mainly loop) regions and the sidechains (Blundell et al. (1988) Eur. J. Biochem. 172: 513; Blundell et al. (1987) Nature 326: 347; Claessens et al. (1989) Protein Eng. 2: 335; Jones et al. EMBO J. 5: 819; Topham et al. (1993) J. Mol. Biol. 229: 194). Such modeling procedures are very successful when the percentage sequence identity to the unknown is high (greater than 40%) and when the known structures cluster around that to be predicted (Srinivasan & Blundell (1993) Protein Eng. 6: 501).

Where a common fold is not known, combinatorial approaches that depend upon the identification of secondary-structure elements using conformational propensities and residue patterns can be valuable (Presnell et al. (1992) Biochemistry 31: 983). The elements of secondary structure are then assembled by docking and/or by using rules concerning supersecondary structures (Whittle and Blundell (1994) Annu. Rev. Biophys. Biomol. Struct. 23: 349-75).

Computational Approaches to Structure Based Drug Design

Once the 3-D structure of a target protein has been defined, computational procedures may be used to suggest ligands that will bind at the active site. Any compound can be a candidate as a putative ligand to mitoNEET. In some embodiments, a compound can be designed de novo. In more embodiments, a compound can be designed using the structure of a compound known to interact with the mitoNEET protein.

Interactive graphics approaches explore new ligand designs manually in ways that might involve, for example, modification of groups on the ligand to optimize complementarity with receptor/enzyme subsites, optimization of a transition state to reflect data from mechanistic studies, replacement of peptide bonds with groups that improve hydrolytic stability while maintaining key hydrogen bond interactions, or linking of adjacent side groups to increase the rigidity of the ligand (Whittle and Blundell (1994) Annu. Rev. Biophys. Biomol. Struct. 23: 349-75). Most of these steps can now be done using systematic computational approaches that fall into three classes: 1) automated docking of whole molecules into receptor sites; 2) precalculating potentials at grid points and fitting molecules to these potentials; and 3) docking fragments and either joining them or growing them into real molecules (Whittle and Blundell (1994) Annu. Rev. Biophys. Biomol. Struct. 23: 349-75).

Attempts at automated docking through the evaluation of electrostatic, steric, or more complex energy states during a systematic search of rotational and translational space for the two molecules has been successful, but the simplification of energy functions required to achieve reasonable computational times has proved limiting (Kuntz et al. (1982). J Mol. Biol. 161: 269; Wodak (1978) J Mol. Biol. 124: 323; Whittle and Blundell (1994) Annu. Rev. Biophys. Biomol. Struct 23: 349-75). Interactive or manual docking involving the positioning of molecules with constant feedback of the energy has been used as an alternative, but the many degrees of freedom and modes of interaction, however, have imposed their own limitations on the utility of this approach (Busetta et al. (1983) J Appl. Crystallogr. 16: 432; Pattabiraman et al. (1985) J Comput. Chem. 6: 432; Tomioka et al. (1987) J Comput. Aided Mol. Des. 1: 197).

Precalculating terms for each point on a grid can be used to identify hydrogen-bonding sites within enzyme active sites and also significantly reduces computational time (Goodford (1985) J Med. Chem. 28: 849). A similar approach involves the use of pseudoenergies calculated from pairwise distributions of atoms in protein complexes or crystals of small molecules, with probe molecules then fitted to these potentials and ranked according to energy (Whittle and Blundell (1994) Annu. Rev. Biophys. Biomol. Struct. 23: 349-75). For example, software such as DOCK (available from University of California, San Francisco), creates a negative image of the target site by placing a set of overlapping spheres so that they fill the complex invaginations of the proposed binding site, and the putative ligands are then placed into the site by matching X-ray or computer derived structures on the basis of a comparison of internal distances (Whittle and Blundell (1994) Annu. Rev. Biophys. Biomol. Struct. 23: 349-75). The candidates are then ranked on the basis of their best orientations.

Other methods include a directed version of DOCK that allows for hydrogen-bond information to be used and conformational flexibility to be allowed, and a method that uses least squares fitting to maximize overlap of enzymes and putative ligands (Leach & Kuntz (1992) J. Comput. Chem. 13: 730; Bacon & Moult (1992) J. Mol. Biol. 225: 849).

Still further methods involve the use of genetic algorithms and graph theory to generate molecular structures within constraints of an enzyme active site or a receptor binding site (Payne & Glen (1993) J Mol. Graph. 11: 76; Lewis (1993) J Mol. Graph. 10: 131). For all of these methods to be useful in drug discovery, however, they must depend upon the existence of large data bases of small molecule structures, such as the Cambridge Structure Data Base and the Fine Chemicals Directory (Allen et al. (1979) Acta Oyst. B 35: 2331; Rusinko et al. (1989) J Chem. Inf. Comput. Sci. 29: 251).

Methods involving fragment docking and then developing algorithms to grow them into larger structures to fill the space available depend upon the exploration of electrostatic, van der Waals, or hydrogen bonding interactions involved in molecular recognition (Whittle and Blundell (1994) Annu. Rev. Biophys. Biomol. Struct. 23: 349-75). Many of these methods incorporate the GRID algorithm as a starting point, and then use GenStar and/or GroupBuild to generate chemically reasonable structures to fill the active sites of enzymes (Rotstein and Murcko (1993) J Comput. Aided Mol. Des. 7: 23; Rotstein and Murcko (1993) J Med. Chem. 36: 1700). Alternatively, the program can start with a docked core or the structure of a fragment from an inhibitor complex and for each atom generated, several hundred candidate positions, representing different bond lengths and torsion angles, are scored on the basis of contacts with the enzyme (Whittle and Blundell (1994) Annu. Rev. Biophys. Biomol. Struct. 23: 349-75).

Numerous computer programs are available and suitable for rational drug design and the processes of computer modeling, model building, and computationally identifying, selecting and evaluating potential inhibitors in the methods described herein. These include, for example, SYBYL (available from TRIPOS, St. Louis Mo.), DOCK (available from University of California, San Francisco), GRID (available form Oxford University, UK), MCSS (available from Molecular Simulations Inc., Burlington, Mass.), AUTODOCK (available from Oxford Molecular Group), FLEX X (available from TRIPOS, St. Louis Mo.), CAVEAT (available from University of California, Berkeley), HOOK (available from Molecular Simulations Inc., Burlington, Mass.), and 3-D database systems such as MACCS-3D (available from MDL Information Systems, San Leandro, Calif.), UNITY (available from TRIPOS, St. Louis Mo.), and CATALYST (available from Molecular Simulations Inc., Burlington, Mass.).

Potential interactive compounds may also be computationally designed de novo using such software packages as LUDI (available from Biosym TechMA), and LEAPFROG (TRIPOS Associates, St. Louis, Mo.). Compound defamation energy and electrostatic repulsion, may be evaluated using programs such as GAUSSIAN 92, AMBER, QUANTA/ CHARMM, and INSIGHT II/DISCOVER. These computer evaluation and modeling techniques may be performed on any suitable hardware including for example, workstations available from Silicon Graphics, Sun Microsystems, and the like. These techniques, methods, hardware and software packages are representative and are not intended to be comprehensive listing.

Other modeling techniques known in the art may also be employed in accordance with this invention. See for example, N. C. Cohen, Molecular Modeling in Drug Design, Academic Press (1996); Whittle and Blundell (1994) Annu. Rev. Biophys. Biomol. Strltct. 23: 349-75; Grootenhuis et al. (1992) Bull. Soc. Chim. Belg. 101: 661; Lawrence and Davis (1992) Proteins Struct. Funct. Genet. 12: 31; Miranker and Karplus (1991) Proteins Struct. Funct. Genet. 11: 29).

Other methods and programs include CLIX (a suite of computer programs that searches the Cambridge Data base for small molecules that have both geometrical and chemical complementarity to a defined binding site on a protein of known three-dimensional structure), and software identified at internet sites including the CAOS/CAMM Center Cheminformatics Suite at www.caos.kun.nl/. and the NIH Molecular Modeling Home Page at cmm.cit.nih.gov/modeling/.

Computer Readable Media

One embodiment of the present invention is a computer-readable medium encoded with atomic coordinate data or binding site data or both, wherein said atomic coordinate data is defined by Table 2, and wherein said binding site data can be defined by any one of the Figures including 1, 2, 3A-C, 4A-F, and 5A-B. In particular embodiments, computer readable media can contain more than about 1%, 5%, 10%, 20%, 30%, 40%, 50%, 60%, 70%, 80%, 90%, 95%, 99% of the coordinates of Table 2.

Another embodiment of the present invention is a method of using the foregoing computer-readable medium wherein a graphical display software program is used to create an electronic file using the atomic coordinate data or the binding site data, wherein the electronic file can be visualized on a computer capable of representing the electronic file as a three dimensional image. Computer readable media, which include both volatile and nonvolatile media, removable and non-removable media, may be any available medium that can be accessed by computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of the any of the above are also included within the scope of computer readable media.

Computer Systems

Some embodiments described herein relate to computer systems containing any portion of the coordinates of Table 2, and methods of screening, identifying, and/or designing compounds using computer systems. Computer systems include the hardware components and means, software components and means and data storage components and means used to analyze atomic coordinate data. The minimum hardware components and means of the computer-based systems of the present invention comprises a central processing unit (CPU), input components and means, output components and means and data storage components and means. Desirably a monitor is provided to visualize structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

Crystallographic Evaluation of Compounds Interacting with mitoNEET

Some embodiments described herein relate to methods and compositions to refine models used to predict interactions between candidate compounds and mitoNEET. In such embodiments, crystals of mitoNEET can be exposed to a candidate compound or mixture of compounds. In other embodiments, mitoNEET can be co-crystallized with a can didate compound. Acquisition and analysis of X-ray diffraction data from these crystals may then be performed using standard methods. If a compound interacts with mitoNEET then positive difference electron density will be observed in the Fourier maps calculated using the X-ray diffraction intensities and phases obtained from the mitoNEET model presented herein. Models of the chemical entities may then be built into the electron density using standard methods, and the resulting structures may be refined against the X-ray diffraction data, providing experimental data describing the interaction of the compounds of interest. Those skilled in the art may use these models to design compounds based either on purely structural data; or on combination of structural data, biological/chemical activity based structure-activity relationship, and in silico drug design. The compounds that are thus designed or selected may further be tested in in vitro and in vivo assays to determine if they regulate mitoNEET. Examples of such assays are described herein.

Identifying Compounds that Interact with MitoNEET In Vitro

Some embodiments described herein relate to in vitro methods for screening and identifying compounds that interact with mitoNEET. In particular embodiments, such compounds can stabilize the 2Fe-2S cluster of mitoNEET. The increase in stability of a 2Fe-2S cluster of a mitoNEET protein associated with a stabilizing compound compared to the stability of a 2Fe-2S cluster of a mitoNEET protein not associated with a stabilizing compound can be an increase of more than about 2-fold, about 3-fold, about 4-fold, about 5-fold, about 10-fold, about 20-fold, and about 100-fold.

Any compound can be screened to identify a compound that can stabilize the 2Fe-2S cluster of mitoNEET, and a variety of methods can be used to identify compounds that interact with mitoNEET. Such methods can include spectroscopic methods for example, optical spectroscopy, electron paramagnetic spectroscopy, NMR spectroscopy, IR spectroscopy, and Raman spectroscopy. Examples of using optical spectroscopy and NMR spectroscopy to identify and characterize a compound that can interact with mitoNEET are described in Example 1. Briefly, in one embodiment, the presence of a candidate compound can cause an increase in the stability of a mitoNEET species at an absorbance of 460 nm at pH 6.0. An example of using Raman spectroscopy to identify and characterize a compound that interacts with mitoNEET is described in Example 2.

In some embodiments, the mitoNEET protein used to identify a compound that can stabilize the 2Fe-2S cluster of mitoNEET can be a modified mitoNEET protein. Such modified mitoNEET proteins can contain mutations that increase the sensitivity of a method used to identify a stabilizing compound. For example, mitoNEET can be modified to modulate binding of the 2Fe-2S cluster, such as a D84N modified mitoNEET where a two-fold increase in stoichiometric in iron/protein be observed; H87Q modified mitoNEET where a lack of stoichiometric iron/protein can be observed; and H87C modified mitoNEET where different Raman spectra can be observed (Wiley et al., The outer mitochondrial membrane protein mitoNEET contains a novel redox-active 2Fe-2S cluster, J. Biol. Chem. 282: 23745-23749 (Aug. 17, 2007)).

Treatment of mitoNEET Associated Disorders

Some embodiments relate to the use of compounds that are identified using the atomic coordinates of any portion of Table 2, namely the 3-D coordinates of mitoNEET, for the treatment of mitoNEET-associated disorders in mammals.

Such disorders can include metabolic dysfunctional diseases or conditions including, but not limited to, those thought to be PPARγ associated diseases or conditions, diabetes, type II diabetes, or syndrome X, cardiovascular diseases, neurodegenerative diseases, cancers, and inflammatory diseases.

Syndrome X (including metabolic syndrome) is loosely defined as a collection of abnormalities including hyperinsulemia, obesity, elevated levels of triglycerides, uric acid, fibrinogen, small dense LDL particles, plasminogen activator inhibitor 1 (PAI-1), and decreased levels of HDL. Similar metabolic conditions include dyslipidemia including associated diabetic dyslipidemia and mixed dyslipidemia, heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular embodiments, the compounds identified using methods described herein can be useful in the treatment and prevention of diabetes and cardiovascular diseases and conditions including hypertension, atherosclerosis, arteriosclerosis, hypertriglyceridemia, and mixed dyslipidaemia.

In more embodiments, compounds that are identified herein can be useful in the treatments of disorders treated with TZDs, such as rosiglitazone or pioglitazone. For example, pioglitazone has been demonstrated to be a potential treatment of neurodegenerative diseases including multiple sclerosis (Feinstein, D. L. et al. (2002) Ann Neurol. 51, 694-702; Pershadsingh, H. A., et al. (2004) J. Neuroinflammation 1, 3; Klotz, L., Schmidt, M., Giese, T., Sastre, M., Knolle, P., Klockgether, T., and Heneka, M. T. (2005) J. Immunol. 175, 4948-4955), Alzheimer disease (Heneka, M. T., Sastre, M., Dumitrescu-Ozimek, L., Hanke, A., Dewachter, I., Kuiperi, C., O'Banion, K., Klockgether, T., Van Leuven, F., and Landreth, G. E. (2005) Brain 128, 1442-1453), and amyotrophic lateral sclerosis (☐ Schutz, B., Reimann, J., Dumitrescu-Ozimek, L., Kappes-Hom, K., Landreth, G. E., Schurmann, B., Zimmer, A., and Heneka, M. T. (2005) J. Neurosci. 25, 7805-7812; Kiaei, M., Kipiani, K., Chen, J., Calingasan, N. Y., and Beal, M. F. (2005) Exp. Neurol. 191, 331-336). Moreover, TZDs have been found to be efficacious inducers of differentiation in cultured pre-adipocyte cell lines (Hiragun et al., J. Cell Physiol. 134:124-130, 1988; Sparks et al., J. Cell. Physiol. 146:101-109, 1991; Kletzien et al., Mol. Pharmacol. 41:393-398, 1992). Treatment of pre-adipocyte cell lines with pioglitazone results in increased expression of the adipocyte-specific genes aP2 and adipsin as well as the glucose transporter proteins GLUT-1 and GLUT-4. These data suggest that the hypoglycemic effects of TZDs seen in vivo may be mediated through adipose tissue. However, as estimates of the contribution of adipose tissue to whole body glucose usage range from only 1-3%, it remains unclear whether the hypoglycemic effects of TZDs can be accounted for by changes in adipocytes only. Furthermore, adipose tissue may not be required for the pharmacology of these compounds (Burant, et al. J Clin Invest 100: 2900-2908, 1997). Additionally, thiazolidinediones have been implicated in appetite regulation disorders, see PCT patent application WO 94/25026 A1, and in increase of bone marrow fat content, (Williams, et al, Diabetes 42, Supplement 1, p. 59A1993).

EXAMPLES

Example 1

Crystal Structure of mitoNEET

Construction of Bacterial Expression Plasmid and Purification of mitoNEET

The portion of the human mitoNEET cDNA corresponding to amino acids 33-108 was amplified by PCR and cloned into the pet21a+ vector. Expression in BL21-CodonPlus-R1L and purification was carried with the time after induction extended to 18 hr at 22° C. as previously described in Wiley, S E, Paddock, M L, Abresch, E C, Gross, L, van der Geer, P, Nechushtai, R, Murphy, A N, Jennings, P A, & Dixon, J E (2007) J Biol. Chem., 282 (33): 23745-9, hereby incorporated by reference in its entirety. We included an additional cation exchange chromatography step using HiTrap (GE Healthcare) to achieve crystal quality purification. The purified material had a peak centered at 458 nm and an optical ratio ($A_{278}/A_{458}$) of 2.3-2.4 under these buffer conditions. Optical spectra were measured on a Cary50 spectrometer (Varian, Walnut Creek, Calif.).

Pioglitazone Binding to mitoNEET

Pioglitazone was solubilized in 0.1 N HCl to a concentration of 3.5 mM. Protein samples containing 15 µM 2Fe-2S centers (7.5 µM dimeric mitoNEET=15 µM monomeric mitoNEET) were measured in 200 mM phosphate-HCl, pH 7.5 with and without stoichiometric (±10%) pioglitazone (25 DC). The stability of the 2Fe-2S clusters were determined from monitoring their characteristic absorbance at 460 nm ($\lambda_{max}$ at pH 6.0) as a function of time (Wiley, S E, Paddock, M L, Abresch, E C, Gross, L, van der Geer, P, Nechushtai, R, Murphy, A N, Jennings, P A, & Dixon, J E (2007) J Biol. Chem., 282 (33): 23745-9). Measurements performed in the NMR buffer (50 mM potassium phosphate, 50 mM sodium chloride, 5 mM Tris at pH 7.8) gave the same results. The measured pH was the same at the beginning and end of each experiment. Control experiments using equal volume addition of 0.1 N HCl did not change the solution pH (±0.01 units) nor alter the physical and spectral properties (±2%) of the protein.

NMR Spectroscopy of mitoNEET

NMR samples of 0.4 mM mitoNEET (protomer concentration) were prepared in 98% $D_2O$ or 90% $H_2O$/10% D20, 50 mM potassium phosphate, 50 mM sodium chloride, 5 mM Tris at pH 7.8. Similar results were obtained in buffers at pH 7.5 and 8.0. Ten µl of pioglitazone was added in 1 µl incremental amounts to 450 µl of mitoNEET sample. This was necessary to avoid locally high acidic spots that would destabilize the 2Fe-2S cluster. Following temperature equilibration, NMR spectra were acquired at 36° C. using Bruker DMX 500 MHz and Bruker DRX 600 MHz spectrometers. Homonuclear IH 2D NOESY spectra were acquired with a mixing time of 400 ms. Spectral processing was performed using Felix Software (Accelrys, San Diego, Calif.).

Crystallization of mitoNEET

Initial crystallization screening was performed both in house and at Hauptman-Woodward Institute (Buffalo, N.Y.). Screens were attempted around initial conditions that yielded crystals. Final conditions were 100 mM Tris-HCl pH 8, 100 mM NaCl and 30-32% PEG3000 in the reservoir. Samples were frozen (77 K) after 1 minute soak in 100 mM Tris-HCl pH 8, 40% PEG3000 sent frozen (77 K) to SSRL in an SSRL supplied cassette system for data collection and analysis.

X-Ray Diffraction of mitoNEET

Frozen crystals were screened using the Stanford Automated Mounter operated by Blu-Ice (Cohen, A E, Ellis, P J, Miller, M D, Deacon, A M, & Phizackerley, R P (2002) J Appl Crystallogr 35, 720-726; McPhillips, T M, McPhillips, S E, Chiu, H J, Cohen, A E, Deacon, A M, Ellis, P J, Garman, E, Gonzalez, A, Sauter, N K, Phizackerley, R P, et al. (2002) J Synchrotron Radiat 9, 401-406). The data were recorded on a 325 mm Marmosaic CCD detector. Datasets were collected from two crystals. A 1.5 Å resolution dataset, used for structure refinement, was collected at SSRL BL11-1 from a 0.9 mm×0.075 mm×0.075 mm crystal. Data was collected from two locations on opposite ends of this crystal using a 0.1×0.075 mm beam size. A 3 wavelength Fe-MAD dataset, used for initial phasing, was collected at SSRL BL9-2 from a 1.0 mm×0.2 mm×0.1 mm crystal. The wavelengths for data collection were selected using a plot of f and f' calculated with the program CHOOCH from the X-ray fluorescence spectrum of the crystal (Evans, G & Pettifer, R F (2001) J Appl Crystallogr 34, 82-86). A total of 360° were collected at each wavelength following the inverse-beam method with a wedge size of 30°. All data were processed with XDS (Kabsch, W (1993) J Appl Crystallogr 26, 795-800).

Structural Determination of mitoNEET

The structure of mitoNEET was determined by MAD phasing (Pahler, A, Smith, J L, & Hendrickson, W A (1990) Acta Crystallogr A 46 (Pt 7), 537-540; Terwilliger, T C & Berendzen, J (1999) Acta Crystallogr D 55, 849-861). Data reduction and primary phasing at a resolution of 2 Å were accomplished using an automated MAD script developed by Ana Gonzalez (SSRL) that integrates [MOSFLM] (Leslie, A G W (2006) Acta Crystallogr D 62, 48-57) and scales [SCALA] (Bailey, S (1994) Acta Crystallogr D 50, 760-763) the data, phase the structure [SOLVE] (Terwilliger, T C & Berendzen, J (1999) Acta Crystallogr D 55, 849-861), and auto builds a partial model [RESOLVE] (Terwilliger, T C (2000) Acta Crystallogr D 56, 965-972). Several rounds of automated model-building and refinement were implemented using ARP/wARP (Perrakis, A, Morris, R, & Lamzin, V S (1999) Nat Struct Biol 6, 458-463) which resulted in significantly improved electron density maps and placement of 97 amino acid sidechains into electron density.

The data from several independent sets were processed using an automated script developed by Qingping Xu at the Joint Center for Structural Genomics (SSRL) that runs XDS (Kabsch, W (1993) J Appl Crystallogr 26, 795). Model completion and refinement were performed in COOT (Emsley, P & Cowtan, K (2004) Acta Crystallogr D 60, 2126-2132) and REFMAC5 (Winn, M D, Murshudov, G N, & Papiz, M Z (2003) Methods Enzymol 374, 300-321) respectively. Analysis of the stereochemical quality of the models were accomplished using an automated validation server developed by Chris Rife at the JCSG (SSRL) implementing MolProbity (Lovell, S C, Davis, I W, Arendall, W B, 3rd, de Bakker, P I, Word, J M, Prisant, M G, Richardson, J S, & Richardson, D C (2003) Proteins 50, 437-450), ADIT (Yang, H W, Guranovic, V, Dutta, S, Feng, Z K, Berman, H M, & Westbrook, J D (2004) Acta Crystallogr D 60, 1833-1839), and WHATIF 5.0 (Vriend, G (1990) J Mol Graphics 8, 52-56). Structural Figures were rendered with PyMol (Delano, W L & Lam, J W (2005) Abstr Pap Am Chem S 230, U1371-U1372).

Structure and Domain Topology of mitoNEET

A soluble form of recombinant human mitoNEET corresponding to amino acids 33-108 (lacking the amino-terminal targeting and transmembrane sequences) was produced for structural analysis. The isolated recombinant protein crystallized in the orthorhombic space group P212121, with unit-cell parameters a=46.81 Å, b=49.62 Å, c=59.01 Å. The Matthews coefficient ($V_m$) of the crystal was 1.9 Å$^3$/Dalton with an estimated solvent content of 33%.

The crystal structure of mitoNEET was determined by MAD phasing (Pahler, A, Smith, J L, & Hendrickson, W A (1990) Acta Crystallogr A 46 (Pt 7), 537-540). For primary phasing, X-ray diffraction intensities were collected at Stanford Synchrotron Radiation Laboratory (SSRL) BL9-2 to a resolution of 1.8 Å at three wavelengths corresponding to the inflection, absorption peak and high energy remote. X-ray diffraction data from a second crystal were collected to an enhanced resolution of 1.5 Å for refinement of the atomic coordinates (Table 1).

TABLE 1

Summary of crystal parameters, data collection, and refinement statistics for mitoNEET

| Space group | P212121 | | | |
|---|---|---|---|---|
| Unit cell parameters | a = 46.81 Å; b = 49.62 Å; c = 59.01 Å | | | |
| Data collection | $\lambda_1$ MADFe | $\lambda_2$ MADFe | $\lambda_3$ MADFe | $\lambda_4$ Native |
| Wavelength (Å) | 1.7418 Å | 1.3624 Å | 1.7374 Å | 0.97945 Å |
| Resolution range (Å) | 59.1-1.80 | 59.1-1.80 | 59.1-1.80 | 46.83-1.50 |
| Number of observations | 151,028 | 180,578 | 152,038 | 604,446 |
| Number of unique reflections | 12,896 | 13,466 | 12,933 | 21,479 |
| Completeness (%) | 95.6 (72.4)$^a$ | 99.6 (100.0) | 95.9 (74.0) | 95.6 (76.4) |
| Mean I/o (I) | 20.8 (2.8)$^a$ | 26.2 (12.4) | 21.4 (3.1) | 30.0 (3.5) |
| Rsym on 1 (%) | 9.4 (45.3)$^a$ | 8.8 (23.7) | 9.8 (40.4) | 5.8 (71.0) |
| Highest resolution shell (Å) | 1.90-1.80 | 1.90-1.80 | 1.90-1.80 | 1.58-1.50 |
| Model and refinement statistics | | | | |
| Resolution range (Å) | 59.1-1.50 | Data set used in refinement | | MNative |
| No. of reflections (total) | 21,479$^b$ | Cutoff criteria | | $|F| > 0$ |
| No. of reflections (test) | 1081 | Rcryst | | 0.182 |
| Completeness (% total) | 95.9 | Rfree | | 0.222 |
| Stereochemical parameters Restraints (RMS observed) | | | | |
| Bond angle (0) | | 1.70 | | |
| Bond length (Å) | | 0.012 | | |
| Average isotropic B-value (Å$^2$) | | 33.1 | | |
| ESU based on Rfree (Å) | | 0.084 | | |

$^a$Highest resolution shell in parentheses.
ESU = Estimated overall coordinate error (Lovell, SC, Davis, IW, Arendall, WB, 3rd, de Bakker, PI, Word, JM, Prisant, MG, Richardson, JS, & Richardson, DC (2003) Proteins 50, 437-450; 31-Bailey, S (1994) Acta Crystallogr D 50, 760-763).
$R_{sym} = \Sigma|I_i - <I_i>|/\Sigma|I_i|$, where $I_i$ is the scaled intensity of the i$^{th}$ measurement and $<I_i>$ is the mean intensity for that reflection.
$R_{cryst} = \Sigma||F_{obs}| - |F_{calc}||/\Sigma|F_{obs}|$, where $F_{calc}$ and $F_{obs}$ are the calculated and observed structure factor amplitudes, respectively.
$R_{free}$ = as for $R_{cryst}$ but for 5.0% of the total reflections chosen at random and omitted from refinement.
$^b$Typically, the number of unique reflections used in refinement is less than the total number that were integrated and scaled. Reflections are excluded due to systematic absences, negative intensities, and rounding errors in the resolution limits and cell parameters.

Figure 2:
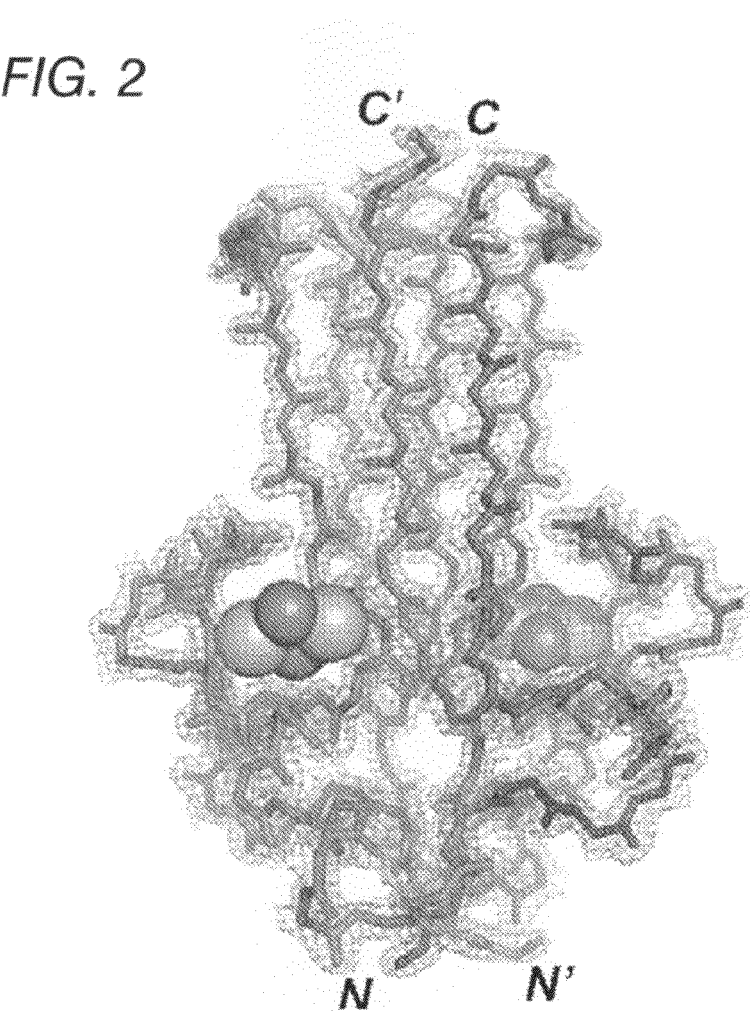
FIG. 2 shows a schematic view of the structure of mitoNEET contoured with an electron density map.
Figure 3:
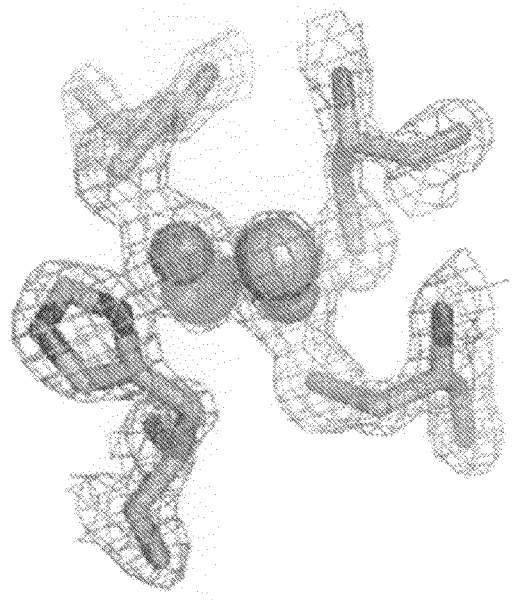
FIG. 3 shows a schematic view of a 2Fe-2S cluster contoured with an electron density map.

The model was refined to an R-factor of 18.2% ($R_{free}$=22.2%). The high quality of the electron density is shown in FIG. 2. FIG. 2 shows the backbone tracing of each protomer chain, namely, chain N—C (darker-shaded), and N'—C' chain (lighter shaded), together with the 2F$_o$—F$_c$ electron density map contoured at 1.50 σ over each chain. The protomers pack in a parallel fashion with each protomer harboring a 2Fe-2S cluster, depicted as lighter-shaded (sulfur) and darker-shaded (iron) spheres; N- and C-termini indicated. FIG. 3 shows an expanded view of one 2Fe-2S cluster (rotated ~90° from the backbone tracing view) and ligands and the corresponding $2F_o-F_c$ electron density map contoured at 2.00σ.

As illustrated in FIG. 4, each protomer is composed of a helical turn (Met62-Asp64), an alpha helix (Ala86-Thr94), an anti-parallel β-structure (Lys68-Tyr71, Leu101-Lys104), an additional "swapping" strand (Ile56-Asp61) and eleven interconnecting β-turns and loops. The protein is folded into two spatially distinct sub-regions: a beta rich or "Beta Cap" domain and a helical 2Fe-2S binding or "Cluster Binding" domain. The refined model reveals a parallel homodimeric structure that includes the cytoplasmic fragment of each protomer from Lys42 to Lys106 on Protomer A and from Ala43 to Glu107 on Protomer B of the dimmer (FIG. 4). The homodimer is tightly packed with 2020 Å$^2$ of buried surface area at the interface. Model validation using the MOLPROBITY (Lovell, S C, Davis, I W, Arendall, W B, 3rd, de Bakker, P I, Word, J M, Prisant, M G, Richardson, J S, & Richardson, D C (2003) Proteins 50, 437-450) structure validation tool indicates that 96.8% of the amino acid residues are in the favored region of ΦΨ space.

FIG. 4A provides a detailed topological analysis of each domain of mitoNEET, and shows a ribbon diagram highlighting the two domains of the mitoNEET dimer: a six stranded beta sandwich forms the intertwined beta cap domain and a larger cluster binding domain carries two 2Fe-2S clusters. The beta rich domain contains a strand swap from opposite ends of the primary sequence to form the Beta Cap structure. This domain contains twenty-eight residues within beta-strands with residues Ile56-Asp61 from Protomer A and Lys68-Tyr71 and Leu101-Lys104 from Protomer B making one three stranded sheet and Ile56-Asp61 from Protomer B and Lys68-Tyr71 and Leu101-Lys104 from Protomer A making the second beta sheet (FIG. 4A). These two strand-swapped sheets pack together to form the Beta Cap domain and form the narrowest end (15 Å across) of the structure (FIG. 4A). FIG. 4B shows a topology diagram highlighting the organization of the secondary structural units (numbered) and illustrates the strand swap between protomers which come from opposite ends of the primary sequence. A prominent feature of the structure is the presence of two 2Fe-2S clusters that are separated by approximately 16 Å from each other within the larger helical cluster binding domain (~30 Å across) (FIG. 4A). The N-termini protrude from the bottom of the cluster binding domain and link to the membrane spanning sequence (not shown) in the full-length protein, orienting this domain close to the OMM. A structural similarity search using the DALI server (Holm, L & Sander, C (1995) Trends Biochem Sci 20, 478-480) revealed that this fold is novel not only when compared to the greater than 650 known Fe—S proteins, but it is also unique when compared to the over 44,200 known members of the structural data bases. Hence this structural class is termed the NEET fold.

FIG. 4C shows coded segments contributing to each domain highlighted on the primary sequence and block diagram. Protomer sequences within the cluster binding domain are labeled with the corresponding regions for cluster, cap and cluster cradle domains. The amino acid sequence of the resolved amino acid for protomer A is shown in the box; the numbers indicate the first (Lys42) and last (Lys106) resolved amino acid. The ligands to the 2Fe-2S cluster, namely, Cys72, Cys74, Cys83, and His87 are indicated in bold and highlighted in grey. The 2Fe-2S binding cradle is located sequentially between two partial beta cap domains. Rendered with Pymol (Delano, W L & Lam, J W (2005) Abstr Pap Am Chem S 230, U1371).

The Buried Interface of MitoNEET

Molecular representations of mitoNEET are shown in FIG. 5 and highlight the packing of hydrophobic and charged residues. In FIGS. 5A and 5B, ribbon diagrams represent mitoNEET in two orientations. The structure shown in FIG. 5B is rotated 90° along the vertical axis shown, with respect to the structure shown in FIG. 5A. One protomer of the dimer is shaded more lightly than the other protomer. Each 2Fe-2S cluster is shown with light-shaded (sulfur) and dark-shaded (iron) spheres.

FIGS. 5C and 5D represent the ribbons of each protomer where five aromatic residues from each protomer are packed together and are emphasized by dotted cloud over the ribbon backbones. The structure shown in FIG. 5D is rotated 90° along the vertical axis shown, with respect to the structure shown in FIG. 5C. Apolar residues are also localized to this region, but are not shown. As is represented in FIGS. 5C and 5D, the hydrophobic/aromatic residues predominantly cluster in the center of the molecule and stabilize the individual protomers.

Figure 5A:
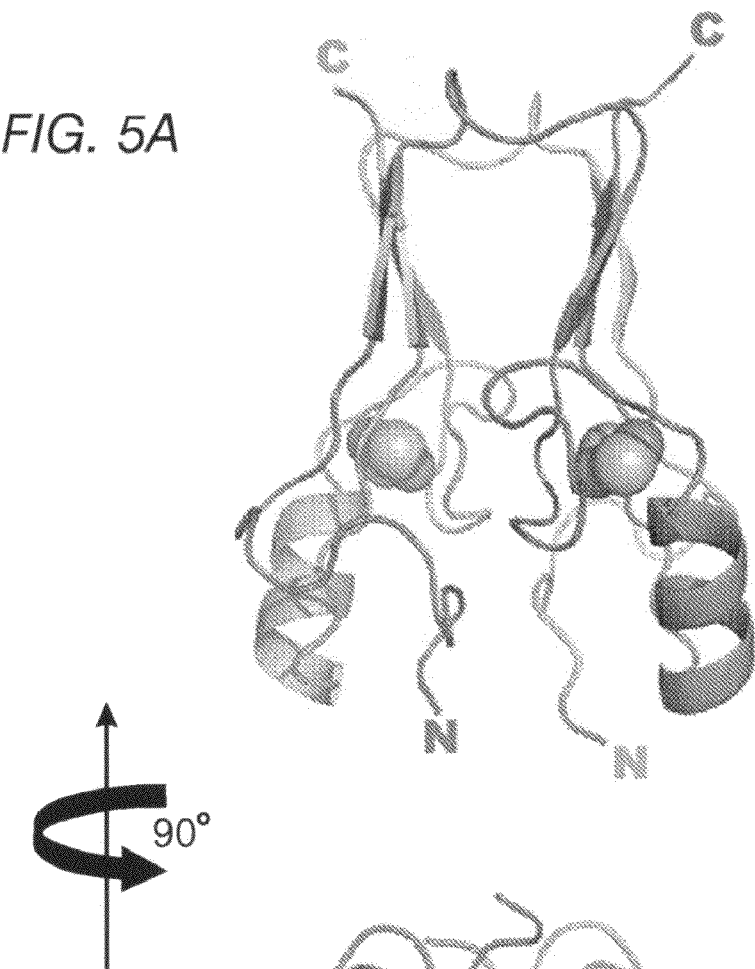
FIGS. 5A and 5B show ribbon diagrams depicting the structure of mitoNEET.
Figure 5B:
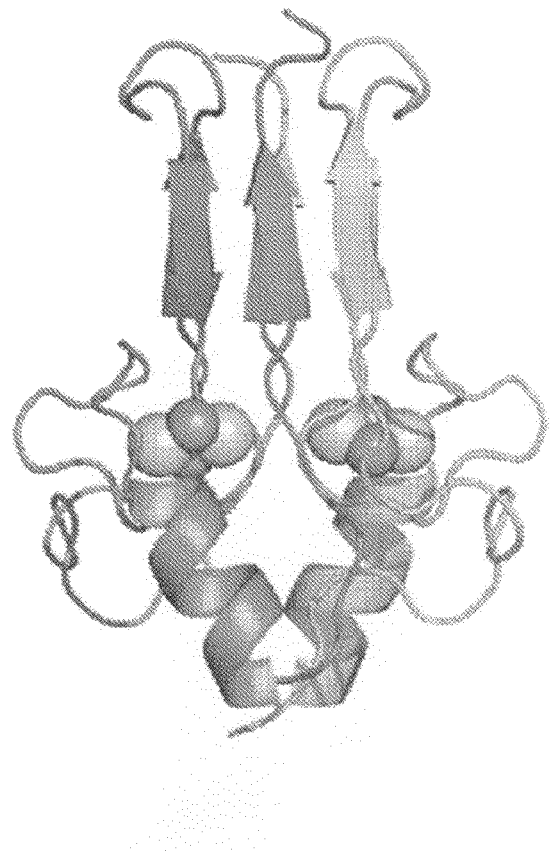
Figure 5E:
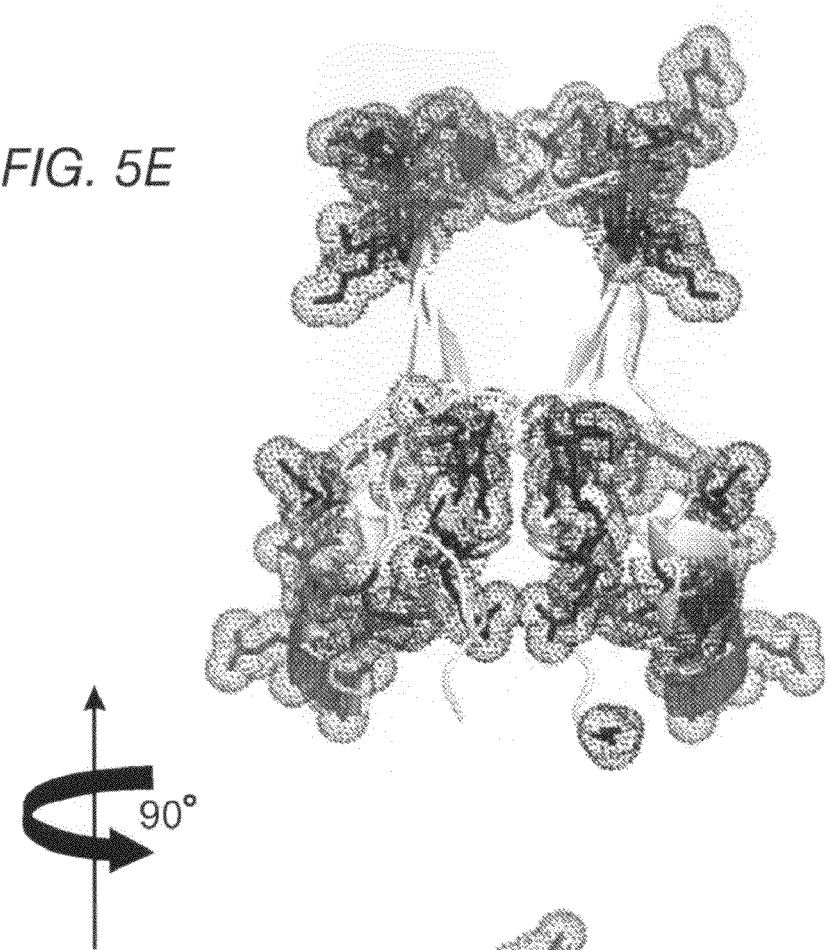
FIGS. 5E and 5F show ribbon diagrams of mitoNEET with negatively- and positively-charged residues emphasized with a contoured cloud over charged residues. Color images of FIGS. 5A-5F can be found in FIG. 2 of Paddock el al. PNAS (2007) 104: 14342-14347, incorporated herein in its entirety.
Figure 5F:
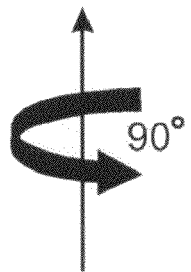
Figure 5F:
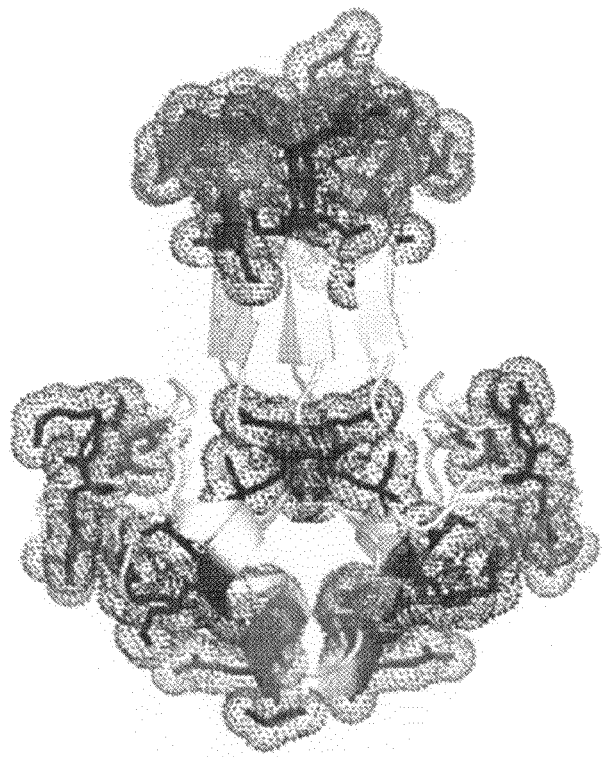

FIGS. 5E and 5F illustrate the separation of charged residues in mitoNEET with negatively charged residues (light-shaded) and positively charged residues (dark-shaded). The structure shown in FIG. 5F is rotated 90° along the vertical axis shown, with respect to the structure shown in FIG. 5E. FIG. 5E emphasizes both the asymmetry of charges within the interior of the molecule and the separation of these charges by the nonpolar residues. Charged residues cluster at the top of the beta cap domain and at the 2Fe-2S cluster binding domain (FIGS. 5E and 5F). This distribution creates a dimer that is polar at the top and bottom separated by a hydrophobic region.

Figure 6A:
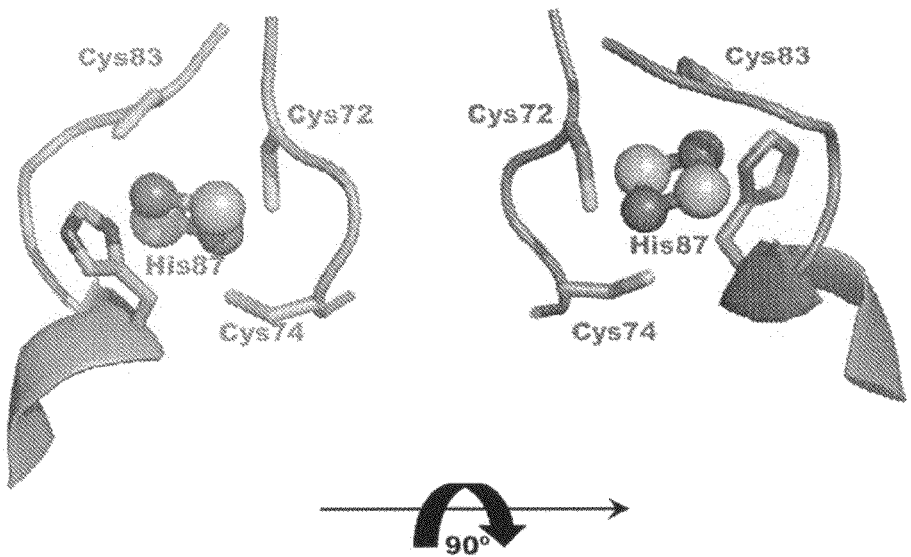
FIG. 6A residues of each promoter, namely, Cys72, Cys 74, Cys83 and His 87.
Figure 6B:
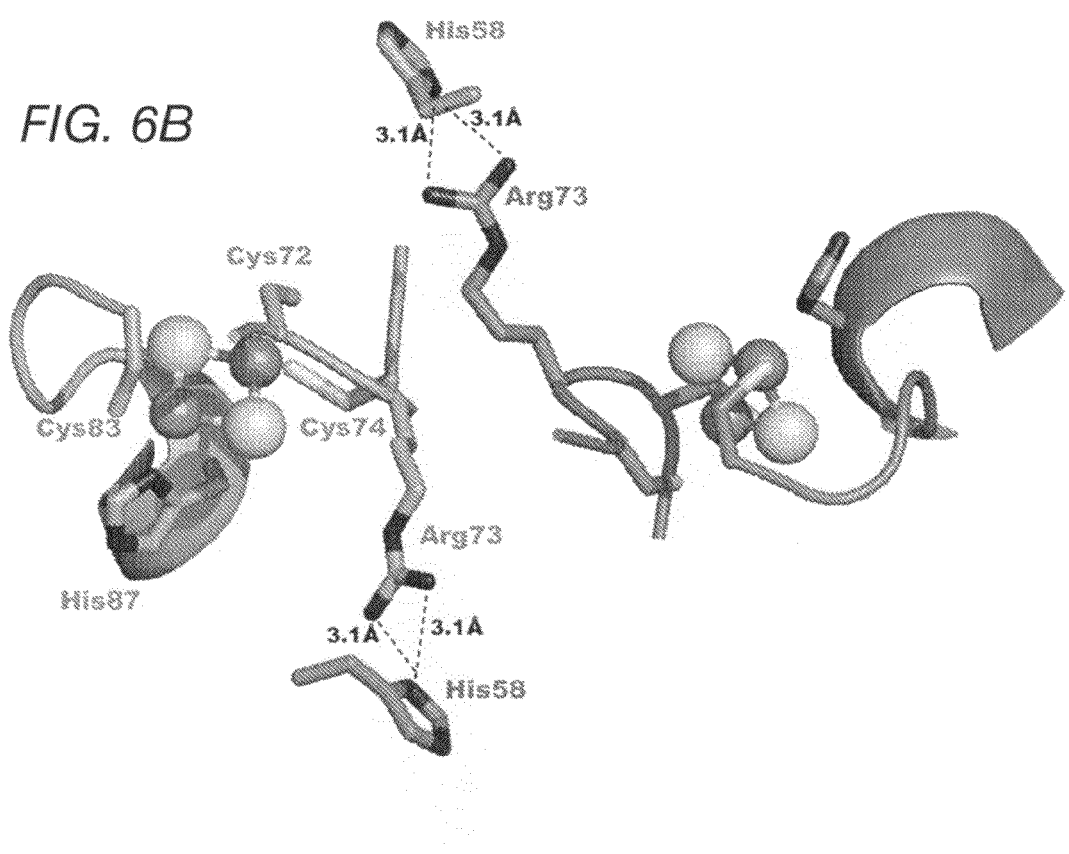
FIG. 6B represents the cluster cradle rotated 90° clockwise from the view presented in FIG. 6A.

An asymmetry of charge is located within the interior of the protein forming a macrodipole with the negative end at the top of the beta cap domain and the positive end within the cluster binding domain, formed by an unexpected interprotomer hydrogen bond between His58 and Arg73 located near the cluster (FIGS. 5E, 5F, 6A, and 6B). The conserved Arg73 is located directly between the Cys ligands of the innermost Fe of the cluster (FIGS. 6A and 6B). This interaction stabilizes the dimer interface. Separating the poles of the dipole are the hydrophobic residues that form a ring around the two protomers within the dimer (FIGS. 5C and 5D). The hydrophobic nature of this area may playa role in flexibility and mobility in the vicinity of the 2Fe-2S cluster contributing to its binding and release.

The 2Fe-2S Cluster Cradle

FIGS. 6A and 6B show schematic views of the 2Fe-2S cluster binding cradle. FIG. 6A represents the 2Fe-2S cluster (Fe represented as darker-shaded spheres and S represented as lighter-shaded spheres) from a perspective rotated ~15° from that shown in FIG. 5A. The amino acids belonging to the individual protomers are shown. The two 2Fe-2S cradles are related to each other via a 180° rotation along the C2 symmetry axis of the dimer. Cys83 and His87 bind the outermost Fe while the innermost Fe is bound by Cys72 and Cys74. The solvent accessible His87 is located at the end of the prominent alpha helix in the Cluster Binding domain (FIG. 4). FIG. 6B represents the cluster cradle rotated 90° clockwise from the view presented in FIG. 6A. Two additional residues, Arg73 and His58, form an unusual His-Arg interprotomer hydrogen bond within the interior of the protein dimer. The distances between the nitrogen of His58 and the guanidinium nitrogen atoms of Arg73 are indicated. The two symmetry related Arg form the positive end of the internal macro-dipole (FIGS. 5E and 5F).

The sequences Lys42-Lys55 and Cys72-Asn97 on each protomer comprise the cluster binding domain (FIGS. 4A and 4C). Within the cluster-binding domain, the polypeptide backbone chain from Cys72-Gly85 folds into a coil that contains the three coordinating Cys ligands—Cys72, Cys74, Cys83—and cradles the 2Fe-2S cluster (FIGS. 6A and 6B). The fourth ligand for the 2Fe-2S cluster (His87) lies at the N-terminus of the a-helix within cluster-binding domain (Ala86-Thr94). mitoNEET shares this unusual 3Cys cluster coordination with the structurally unrelated cluster scaffold protein IscU (Li, K, Tong, W H, Hughes, R M, & Rouault, T A (2006) J Biol Chem 281, 12344-12351; Ramelot, T A, Cort, J R, Goldsmith-Fischman, S, Komhaber, G J, Xiao, R, Shastry, R, Acton, T B, Honig, B, Montelione, G T, & Kennedy, M A (2004) J Mol Biol 344, 567-583). The 3Cys-1His coordination seen here is in agreement with the conclusions of previous solution studies of mitoNEET (Wiley, S E, Paddock, M L, Abresch, E C, Gross, L, van der Geer, P, Nechushtai, R, Murphy, A N, Jennings, P A, & Dixon, J E (2007) J. Biol. Chem., 282 (33): 23745-9). Cys83 and His87 are solvent accessible and coordinate to the outermost Fe while Cys72 and Cys74 coordinate the innermost Fe of the 2Fe-2S cluster (FIGS. 6A and 6B). The binding coils, one from each protomer, protrude away from the core of the dimer and the non-crystallographic dyad axis (FIG. 2). The cluster binding domain, and specifically the C-terminus of each a-helix is predicted to be situated near the OMM in vivo.

Pioglitazone Stabilizes the 2Fe-2S Cluster

Figure 7A:
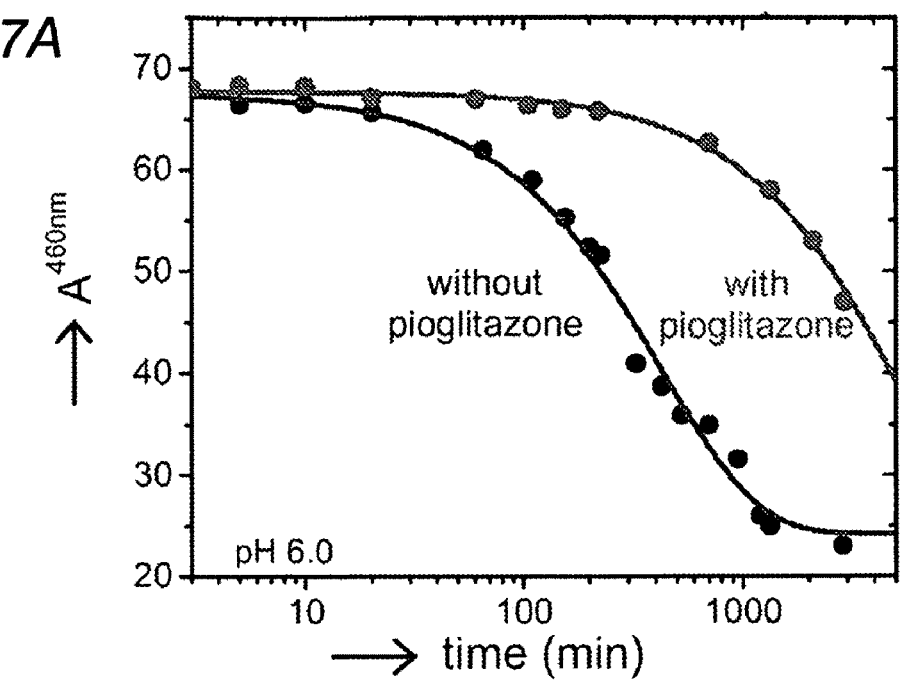
FIG. 7A shows a graph of the absorbance of mitoNEET at 460 nm over time in the presence and absence of pioglitazone.
Figure 7B:
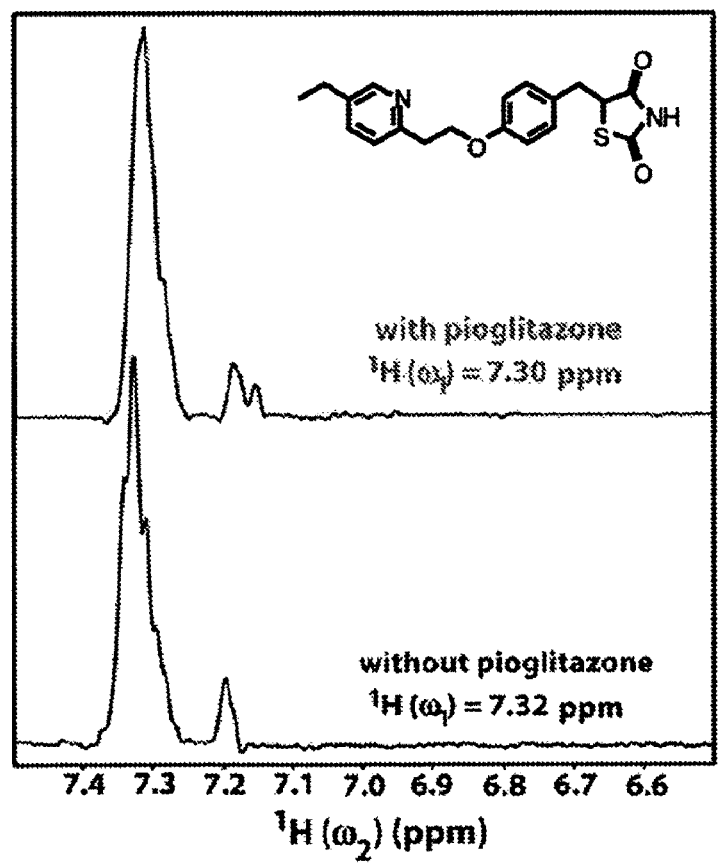
FIG. 7B shows a graph of 1D vectors derived from 2D homonuclear $^1$H NOESY spectra of mitoNEET, with and without pioglitazone, $D_2O$, pH 7.8, 35° C.

Pioglitazone, a member of the TZD class of insulin-sensitizer drugs, binds to mitoNEET in vitro as demonstrated by photoaffinity labeling (Colca, J R (2006) Biochem Pharmacol 72, 125-131; Colca, J R & Kletzien, R F (2006) Expert Opin Investig Drugs 15, 205-210; 18-Hofmann, C A & Colca, J R (1992) Diabetes Care 15, 1075-1078; Colca, J R, McDonald, W G, Waldon, D J, Leone, J W, Lull, J M, Bannow, C A, Lund, E T, & Mathews, W R (2004) Am J Physiol Endocrinol Metab 286, E252-260). To observe the effects of pioglitazone binding on the protein stability of mitoNEET, the characteristic absorbance of the 2Fe-2S cluster at 460 nm was measured as a function of time at pH 6.0 under conditions known to lead to cluster release (Wiley, S E, Paddock, M L, Abresch, E C, Gross, L, van der Geer, P, Nechushtai, R, Murphy, A N, Jennings, P A, & Dixon, J E (2007) J Biol. Chem., 282 (33): 23745-9). FIGS. 7A and 7B illustrate that the binding of pioglitazone to mitoNEET stabilizes the Fe—S cluster. As FIG. 7A shows, the stability of the 2Fe-2S cluster of mitoNEET was increased in the presence of pioglitazone. Here, the change in the signature absorbance spectrum (460 nm) of the 2Fe-2S cluster was monitored as a function of time at pH 6.0 in the absence and presence of stoichiometric pioglitazone (15 µM). The binding of the insulin sensitizing drug pioglitazone increased the observed half life by 10-fold. Accordingly, the presence of pioglitazone (stoichiometric to the total 2Fe-2S cluster concentration) increased the stability by ~10-fold compared to the control sample lacking pioglitazone (FIG. 5A).

FIG. 7B shows 1-D vectors derived from 2-D homonuclear NOESY spectra of mitoNEET, with and without pioglitazone, $D_2O$, pH 7.8, 35° C. The 1-D vectors are along $\omega_1$ at the $w_2$ chemical shift typical of the aromatic ring protons of Trp and/or Phe residues. Accordingly, these two-dimensional homonuclear NMR methods demonstrated that while the overall structure of the protein remains intact upon drug binding, chemical shift changes are observed in the aromatic and aliphatic resonances (Wuthrich, K (1986) NMR of proteins and nucleic acids (Wiley, New York). NMR resonance(s) of the ring protons of aromatic residues shift and exhibit new through-space couplings upon addition of pioglitazone (FIG. 7B). In addition, the amide and ring nitrogen protons of the Tyr71 and Trp75 residues are stabilized leading to slower hydrogen/deuterium exchange rates.

Figures 8A, 8B:
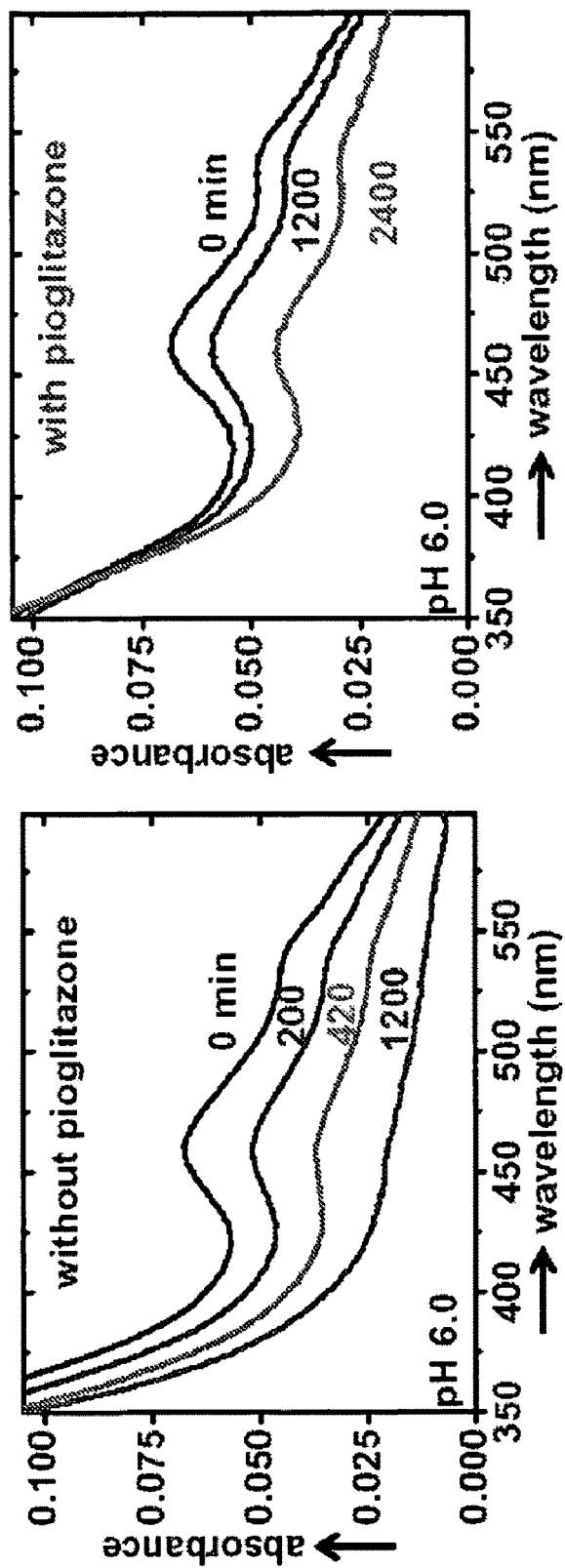
FIGS. 8A and 8B show optical spectra of mitoNEET at pH 6.0 in the absence and presence of pioglitazone after various lengths of time.

FIGS. 8A and 8B show optical spectra of mitoNEET with (~15 µM) and without pioglitazone at different times following dilution into 200 mM Citrate pH 6.0 (~15 µM protein). The rate of decay was ~10-fold slower in the sample with addition of stoichiometric pioglitazone, an insulin sensitizing drug.

Putative Functions of mitoNEET

Figure 9:
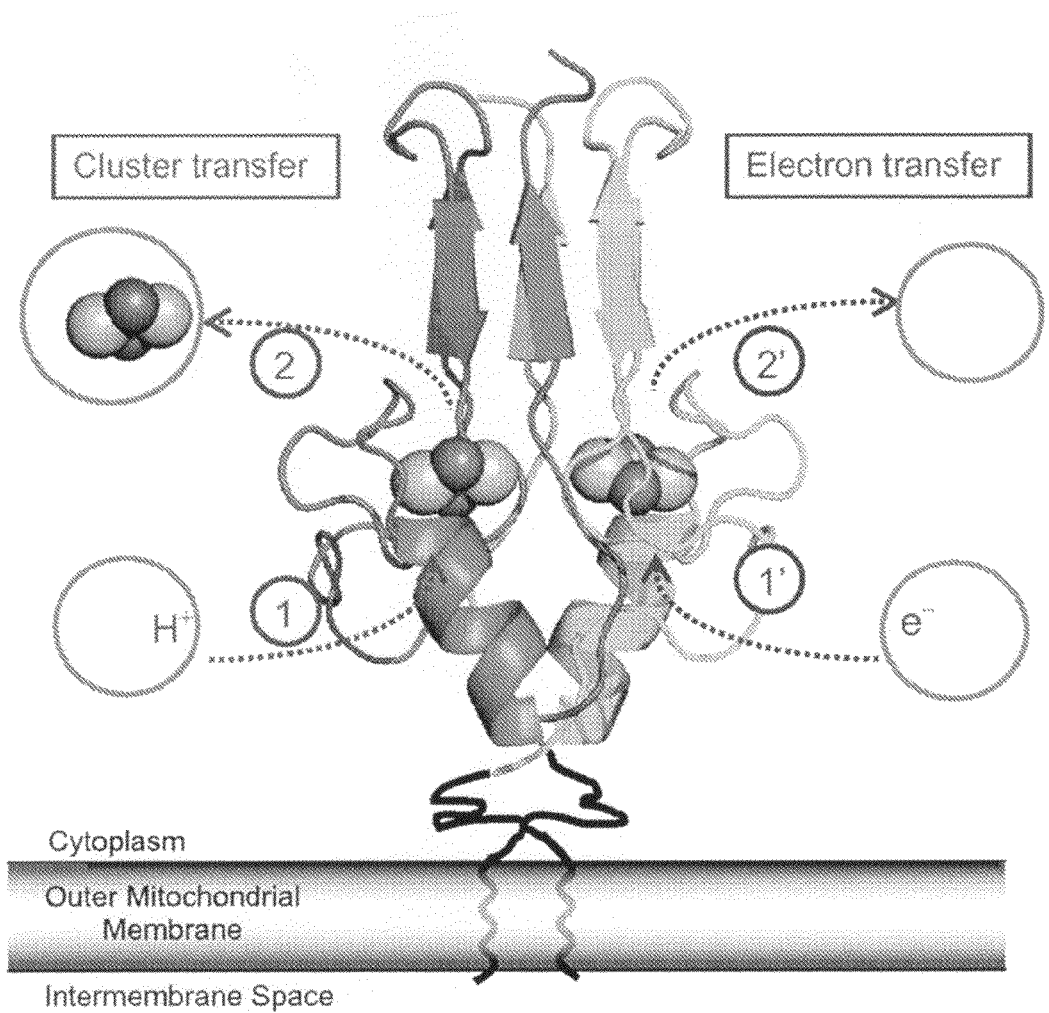
FIG. 9 summarizes putative in vivo functions of mitoNEET.

Although more than 650 structures of Fe—S containing proteins are currently available, the structure of mitoNEET presented here is unique among all known structures (over 44,200 structures currently). FIG. 9 illustrates putative functions for MitoNEET in vivo. MitoNEET is shown linked to the outer mitochondrial membrane (OMM) (not to scale). Without wishing to be bound to any one theory, two possible functions of mitoNEET can be suggested: (1) cluster transfer; and (2) and electron transfer.

With respect to electron transfer, the 2Fe-2S cluster can be reduced (1') and reoxidized (2') (Wiley, S E, Paddock, M L, Abresch, E C, Gross, L, van der Geer, P, Nechushtai, R, Murphy, A N, Jennings, P A, & Dixon, J E (2007) J Biol. Chem., 282 (33): 23745-9). The 2Fe-2S cluster of recombinant mitoNEET is reversibly reduced/oxidized at pH 8.0 (FIG. 9), consistent with a function for mitoNEET that involves electron transfer. Such functions could include redox reactions with metabolic intermediates, cofactors and/or proteins localized at the OMM. As mitoNEET regulates maximal respiratory capacity in mouse heart mitochondria, it is possible that the protein acts as a sensor, adjusting oxidative capacity through participation in a redox-sensitive signaling pathway (Wiley, S E, Murphy, A N, Ross, S A, van der Geer, P, & Dixon, J E (2007) PNAS 104, 5318-5323).

With respect to cluster transfer, the 2Fe-2S cluster dissociates from the protein upon protonation of His87. Accordingly, changes in the interaction of His87 with the cluster are likely related to its function. In vivo this unique fold of mitoNEET stabilized by pioglitazone interaction may be broken by docking of another protein thereby providing a convenient trigger for cluster release. Binding of pioglitazone to mitoNEET (FIGS. 7A and 7B) increases the stability of the 2Fe-2S cluster thereby inhibiting release of the cluster.

His87 may not serve as a stabilizing ligand for the 2Fe-2S when protonated because His87 resides at the N-terminus of the helical sequence AHTKHNEET (SEQ ID No: 2) that is predicted to have only marginal helical content in solution but is likely stabilized by cluster binding (Mufioz, V & Serrano, L (1997) Biopolymers 41, 495-509). However, protonation of the His87 may destabilize the helix facilitating cluster release/transfer. A second histidine (His58) that forms an unusual interprotomer hydrogen bond with Arg73 (FIG. 6B) is also located near the cluster. Disruption of this hydrogen bond would weaken the interprotomer interaction. Since Arg73 is located sequentially between the Cys ligands of the innermost Fe of the cluster (FIG. 6B), perturbation of its interaction with His58 will likely lead to reorientation of the inner sphere Cys ligands potentially providing additional conformational control of binding. Below pH 8 in vitro, the 2Fe-2S cluster is labile; the 2Fe-2S cluster is less stable at physiological pH than other 2Fe-2S proteins (Wiley, S E, Paddock, M L, Abresch, E C, Gross, L, van der Geer, P, Nechushtai, R, Murphy, A N, Jennings, P A, & Dixon, J E (2007) J. Biol. Chem., 282 (33): 23745-9). Modulation of the destabilization/stabilization of cluster binding in vivo could be achieved under physiological conditions upon docking of another protein. This would provide a convenient trigger for controlling cluster release.

Modulation of the destabilization/stabilization of cluster binding in vivo suggests that mitoNEET participates in Fe—S cluster assembly, potentially facilitating cluster shuttling between proteins in the mitochondria and cytoplasm. Proteins that act as scaffolds for Fe—S cluster assembly are within the mitochondrial matrix and cytoplasm of yeast and mammalian cells, although matrix synthesis is believed to predominate (Li, K, Tong, W H, Hughes, R M, & Rouault, T A (2006) J Biol Chem 281, 12344-12351; Netz, D J, Pierik, A J, Stumpfig, M, Muhlenhoff, U, & Lill, R (2007) Nat Chem Biol 3, 278-286). Although several proteins involved in the export of clusters synthesized in the mitochondrial matrix have been identified in yeast (Lill, R & Muhlenhoff, U (2006) Annu Rev Cell Dev Biol 22, 457-486, Lill, R, Dutkiewicz, R, Elsasser, H P, Hausmann, A, Netz, D J, Pierik, A J, Stehling, 0, Urzica, E, & Muhlenhoff, U (2006) Biochim Biophys Acta 1763, 652-667), the mechanism by which clusters are transported across the OMM and shuttled to cytosolic apoproteins in yeast and in higher organisms is unknown. MitoNEET is uniquely positioned to possibly receive and then transfer a cluster that has crossed the outer membrane, or alternately may serve as a Fe—S cluster reservoir or storage protein (FIG. 9).

Pioglitazone is a highly hydrophobic molecule that is largely bound to serum albumin after patient ingestion and prior to cellular uptake and binding to its intracellular targets (Takeda Pharmaceutical Company Limited, www.fda.gov/cder/foi/label/2005/021842lbl.pdf). In addition to hydrophobic interactions, binding of pioglitazone increases stability of the 2Fe-2S cluster and of hydrogen bonding interactions within the protein. Taken together with the unique distribution of hydrophobic residues in the dimer (FIGS. 5C and 5D), the structural results described herein have important implications for both mechanisms of drug action and optimization of TZDs. Although these compounds may activate peroxisome proliferator-activating receptors, data has accumulated suggesting alternative modes of action involving mitochondria (Feinstein, D L, Spagnolo, A, Akar, C, Weinberg, G, Murphy, P, Gavrilyuk, V, & Dello Russo, C (2005) Biochem Pharmacol 70, 177-188). In view of the foregoing, mitoNEET is a desirable target for designing drugs.

Example 2

Resonance Raman Studies of the (His)(Cys)$_3$ Ligand Environment of the 2Fe-2S Cluster of mitoNEET The visible resonance Raman spectra were obtained for native mitoNEET, a H87C mitoNEET mutant, and TZD-bound mitoNEET. Measurements were made at several pH levels. Identities of vibrational modes were assigned by comparison with previous ferredoxin and Rieske protein studies. The resonance Raman spectra presented here are the first of their kind for a naturally occurring Fe$_2$S$_2$(His)(Cys)$_3$ cluster binding system.

A key pH-dependent mode influenced by the Fe—N bond character was identified, supporting observations in which increased cluster stability was observed at high pH values (Wiley, S. E.; Paddock, M. L.; Abresch, E. C.; Gross, L.; van der Geer, P.; Nechushtai, R.; Murphy, A. N.; Jennings, P. A.; Dixon, J. E.; *J. Biol. Chem.* 2007, 282, 23745-23749). pH-dependence studies as well as measurements of the H87C mutant enabled the identification of key bands with significant contributions from Fe—N motions. These assignments support one hypothesis that the observed pH-dependence of the rate of metal cluster loss is due to $N_\delta$ protonation of the H87 residue. In the presence of pioglitazone, the Raman spectra exhibit similar characteristics to those observed at high pH, lending molecular support to the increased cluster stability observed through optical kinetics studies under similar conditions (Paddock, M. L.; Wiley, S. E.; Axelrod, H. L.; Cohen, A. E.; Roy, M.; Abresch, E. C.; Capraro, D.; Murphy, A. N.; Nechushtai, R.; Dixon, J. E.; Jennings, P. A.; *Proc. Natl. Acad. Sci. U.S.A.* 2007, 104, 14342-14347).

Preparation of Native and Mutant mitoNEET

Cytoplasmic domains of native and H87C mutant mitoNEET were constructed, expressed and purified as described herein, and in Paddock, M. L.; Wiley, S. E.; Axelrod, H. L.; Cohen, A. E.; Roy, M.; Abresch, E. C.; Capraro, D.; Murphy, A. N.; Nechushtai, R.; Dixon, J. E.; Jennings, P. A.; *Proc. Natl. Acad. Sci. U.S.A.* 2007, 104, 14342-14347; and Wiley, S. E.; Paddock, M. L.; Abresch, E. C.; Gross, L.; van der Geer, P.; Nechushtai, R.; Murphy, A. N.; Jennings, P. A.; Dixon, J. E.; *J. Biol. Chem.* 2007, 282, 23745-23749, hereby incorporated by reference in their entireties. The single histidine ligand H87 of the 2Fe-2S cluster was replaced by cysteine in the H87C mutant creating a 2Fe-2S cluster bound by four cysteines. This mutation retains the 2Fe-2S cluster and is less labile as described herein. The optical ratio $A_{280}/A_{458}$ was near 2.3 and crystals were grown from the H87C mutant, indicating of a high level of purity. Stock protein solutions were stored at >1 mM concentration and diluted to between 100 and 200 µM in 100 mM phosphate buffer at the indicated pH for resonance Raman measurements. All samples were measured in the oxidized state as isolated. *Mastigocladus laminosus* ferredoxin (mFd) was expressed and purified as previously described (Fish, A.; Lebendiker, M.; Nechushtai, R.; Livnah, O.; Acta Crystallogr., Sect. D 2003, 59, 734-736). Pioglitazone was purchased from Bosche Scientific (New Brunswick, N.J.) and solubilized in 0.1N HCl to ~3 mM.

Stability of the 2Fe-2S Cluster

The 2Fe-2S cluster of native mitoNEET is labile and the rate of cluster loss is inversely related to the pH, namely, $k=k_0 10^{-pH}$ (Wiley, S. E. et al. J. Biol. Chem. 2007, 282, 23745-23749). Since the 2Fe-2S center has strong visible absorption bands, the cluster loss was assayed by disappearance of the visible absorbance peak near 460 nm. The majority of the decay (>80% of the signal loss) could be adequately fit to a single exponential. Due to the change in buffer from tris to phosphate, the rates of decay in the current study are slower than other reports, but are still inversely related to the pH (Wiley, S. E.; Paddock, M. L.; Abresch, E. C.; Gross, L.; van der Geer, P.; Nechushtai, R.; Murphy, A. N.; Jennings, P. A.; Dixon, J. E.; *J. Biol. Chem.* 2007, 282, 23745-23749).

Resonance Raman Spectroscopy on mitoNEET

Laser excitation was provided by the 514.5 nm line of a mixed-gas Kr—Ar laser (Spectra-Physics Stabilite). The 50-75 watt beam was focused (spot size ~10 µm diameter) into a 1.5-1.8 mm OD capillary that contained protein sample. Experiment durations ranged from 20 to 30 minutes, depending on the applied power. For low pH experiments, the capillary was translated horizontally across the laser focus during data acquisition. Room temperature Raman spectra of buffered protein solutions and buffer-only solutions were acquired. Scattered photons were collected in a right-angle geometry by a camera lens and focused onto the 170 µm entrance slit of an F/6.9 spectrograph (Spex Industries 1700). Rayleigh scattering was rejected by a 514.5 nm long-pass edge filter (Semrock RazorEdge) whose angle was tuned by optimizing the intensity of the 460 cm$^{-1}$ CCl$_4$ signal. The spectrometer was equipped with a 1200 groove/mm diffraction grating (Horiba JobinYvon) blazed at 500 nm. Dispersed light was imaged onto a peltier-cooled CCD camera (Princeton Instruments Pixis 256). Wavelength calibration was performed with a neon lamp. Reported energies are accurate to ±2 cm$^{-1}$ and the entrance slit bandpass was 7 cm$^{-1}$.

Data Analysis

Data collection periods were divided into one-minute segments to monitor photodamage and manage interference from cosmic rays. Although sequential minute long spectra exhibited a gradual decrease in baseline intensity (as much as 40%), no peak shifts, relative intensity changes, or new peaks were observed during the entire course of a 20-30 minute experiment. Individual one minute spectra were summed over the total acquisition time to obtain a single spectrum. Appropriate buffer-only spectra were subtracted from sample spectra to remove signal from the buffer and isolate scattering contributions due to the protein. Differences in the Raman spectra of protein and buffer-only solutions as a function of pH were evident; systematic changes in the buffer-only spectra provided a convenient measurement of the pH of the <40 μL solution in the capillary. The residual fluorescence and scattering background in each spectrum was removed by baseline interpolation. Raman features were modeled as sums of Gaussian peaks and decompositions were performed using a least-square fitting technique. All data analysis was performed using WaveMetrics Igor Pro 5.01.

Resonance Raman Spectra of Oxidized mFd and mitoNEET

Figure 10:
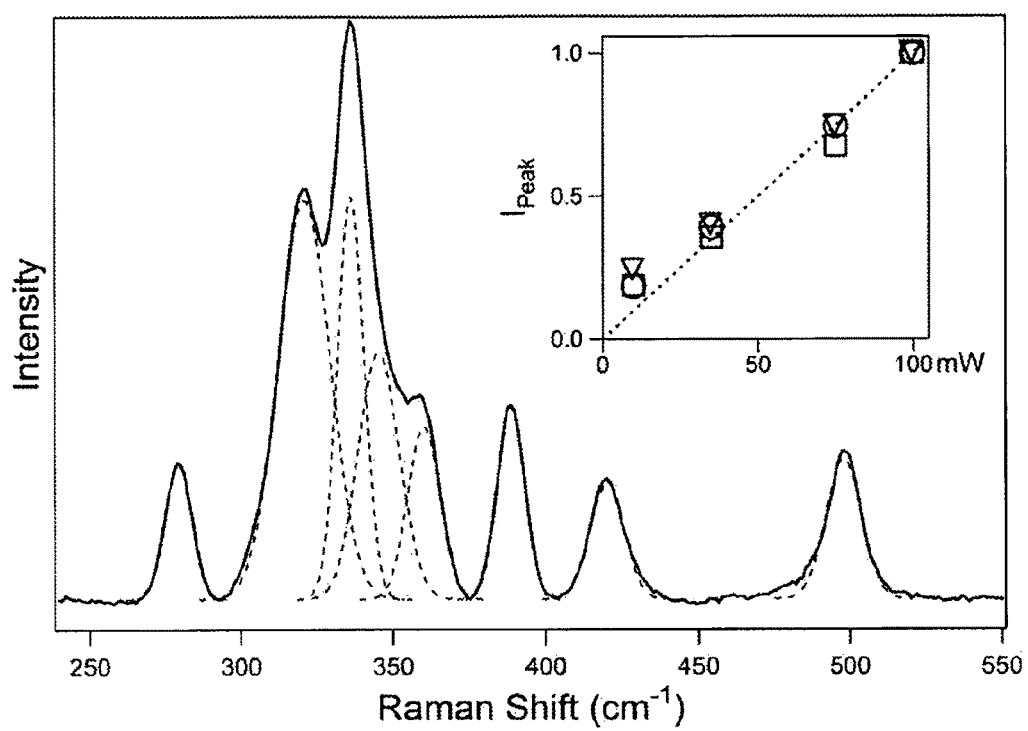
FIG. 10 shows a resonance Raman spectrum for oxidized *Mastigocladus laminosus* ferredoxin at pH 7.5. The solid curve is the measured data of intensity versus the Raman shift, and the dashed lines indicate components of the Gaussian decomposition. The inset shows power dependence data where the ordinate is the ratio of peak intensity at a given power to peak intensity at 100 mW, circles represent the peak found at 279 $cm^{-1}$, squares represent the peak found at 389 $cm^{-1}$, and triangles represent the peak found at 420 $cm^{-1}$. An idealized linear power-signal relationship is represented by the dotted line.

Published ferredoxin spectra exhibit wide variety of spectral shapes and peak positions (Yachandra, V. K.; Hare, J.; Gewirth, A.; Czernuszewicz, R. S.; Kimura, T.; Holm, R. H., Spiro, T. G.; J. Am Chem. Soc. 1983, 105, 6462-6468; Rotsaert, F. A. J.; Pikus, J. D.; Fox, B. G.; Markley, J. L.; Sanders-Loehr, J.; J. Biol. Inorg. Chem. 2003, 8, 318-326; Han, S.; Czernuszewicz, R. S.; Kimura, T.; Adams, M. W. W.; Spiro, T. G.; J. Am. Chem. Soc. 1989, 111, 3505-3511). FIG. 10 shows resonance Raman spectrum of oxidized mFd at pH 7.5.

At pH 7.5 the spectrum of mFd (FIG. 10) was resolved into 7 peaks in the region between 250 and 450 cm$^{-1}$, summarized in Table 3. Table 3 shows mFd resonance Raman peak assignments (in cm$^{-1}$) by comparison with bovine adrenodoxin (Ado) and *Porphyra umbilicalis* (red algae) ferredoxin (Fd) (Han, S.; Czernuszewicz, R. S.; Kimura, T.; Adams, M. W. W.; Spiro, T. G.; J. Am. Chem. Soc. 1989, 111, 3505-3511). Mode symmetry in idealized D$_{2h}$ point group for Fe$_2$S$^b_2$S$^t_4$, where S$^t$ is a terminal sulfur from a cysteine residue and S$^b$ is a bridging sulfur member of the cluster. The coordinate system is defined by an x-axis collinear with Fe atoms, a y-axis collinear with bridging S atoms, and a z-axis perpendicular to Fe—S$^b$ plane, with the origin at the center of inversion.

TABLE 3 mFd resonance Raman peak assignments

| Assignment | mFd | Ado | Fd |
|---|---|---|---|
| $B_{2u}^b$ | 420 | 421 | 426 |
| $A_g^b$ | 389 | 393 | 395 |
| $B_{3u}^b$ | 360 | 349 | 367 |
| $B_{1u}^t$, $B_{2g}^t$ | 345 | 341 | 357 |
| $A_g^t$ | 336 | 329 | 339 |
| $B_{1g}^b$ | 320 | 317 | 329 |
| $B_{3u}^t$ | 279 | 291 | 282 |

The assignments of mFd were based on similarity to those previously assigned in ferredoxin from *Porphyra umbilicalis* (red algae) and bovine adrenodoxin (Kuila, D.; Schoonover, J. R.; Dyer, R. B.; Batie, C. J.; Ballou, D. P.; Fee, J. A.; Woodruff, W. H.; *Biochim. Biophys. Acta* 1992, 1140, 175-183). Power dependence experiments in the range 10-100 mW were performed. No power-dependent changes in peak position, width and relative intensities were observed across this region (FIG. 10, inset), indicating that 50-75 mW does not cause measurable photodamage. There is noticeable deviation from the idealized power-signal relationship at low power (10 mW), but error is expected to be increased at low power due to decreased signal/noise ratio.

Figure 11:
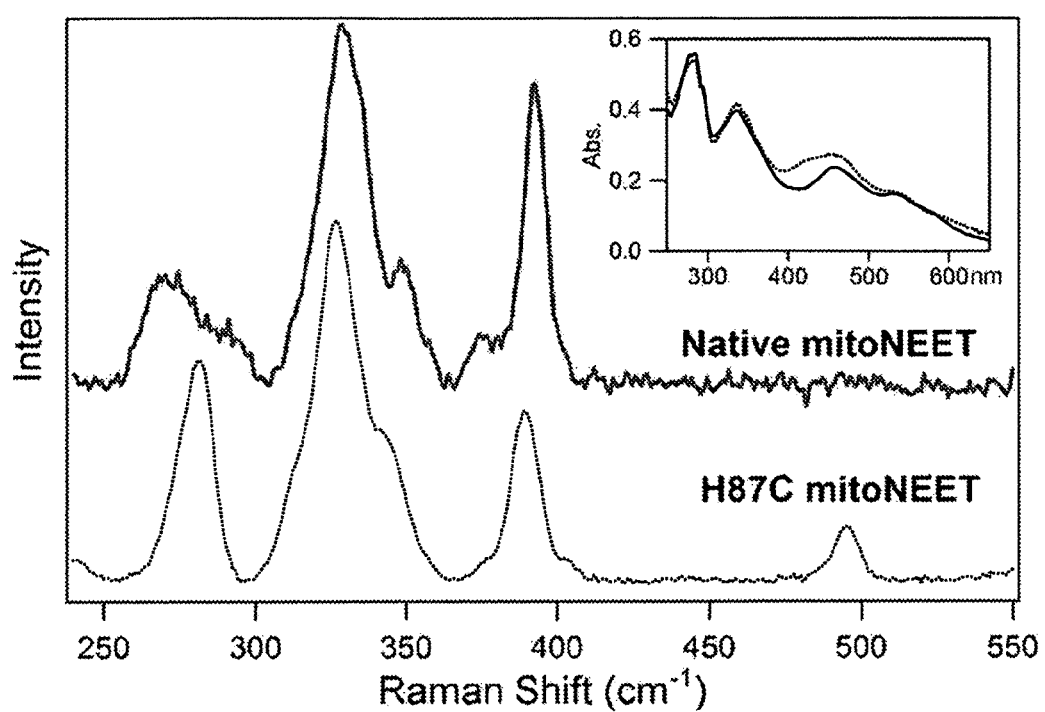
FIG. 11 shows resonance Raman spectra for native mitoNEET (solid line) and a mutant H87C mitoNEET (dotted line) at pH 7.5. The inset shows the absorption spectra of both native and mutant H87C mitoNEET.

Resonance Raman spectra of native and H87C mitoNEET were compared to help identify normal modes with large contribution from the Fe—N moiety. Spectra measured at pH 7.5 are shown in FIG. 11 along with the absorption spectra of the two forms of mitoNEET (FIG. 11, inset). The Raman spectra were normalized to the amplitude of the observed peak near 330 cm$^{-1}$. The most prominent differences between native and H87C mitoNEET were the disappearance of bands at ~485 and 405 cm$^{-1}$ and the change in band compositions in the 250-300 cm$^{-1}$ and 360-420 cm$^{-1}$ regions. The Fe—N vibrations of interest are likely to be found Bands in the 250-300 cm$^{-1}$ region (Kuila, D.; Fee, J. A.; Schoonover, J. R.; Woodruff, W. H.; Batie, C. J.; Ballou, D. P.; J. Am Chem. Soc. 1987, 109, 1559-1561).

Effects of pH on the Resonance Raman Spectra of mitoNEET

Figure 12:
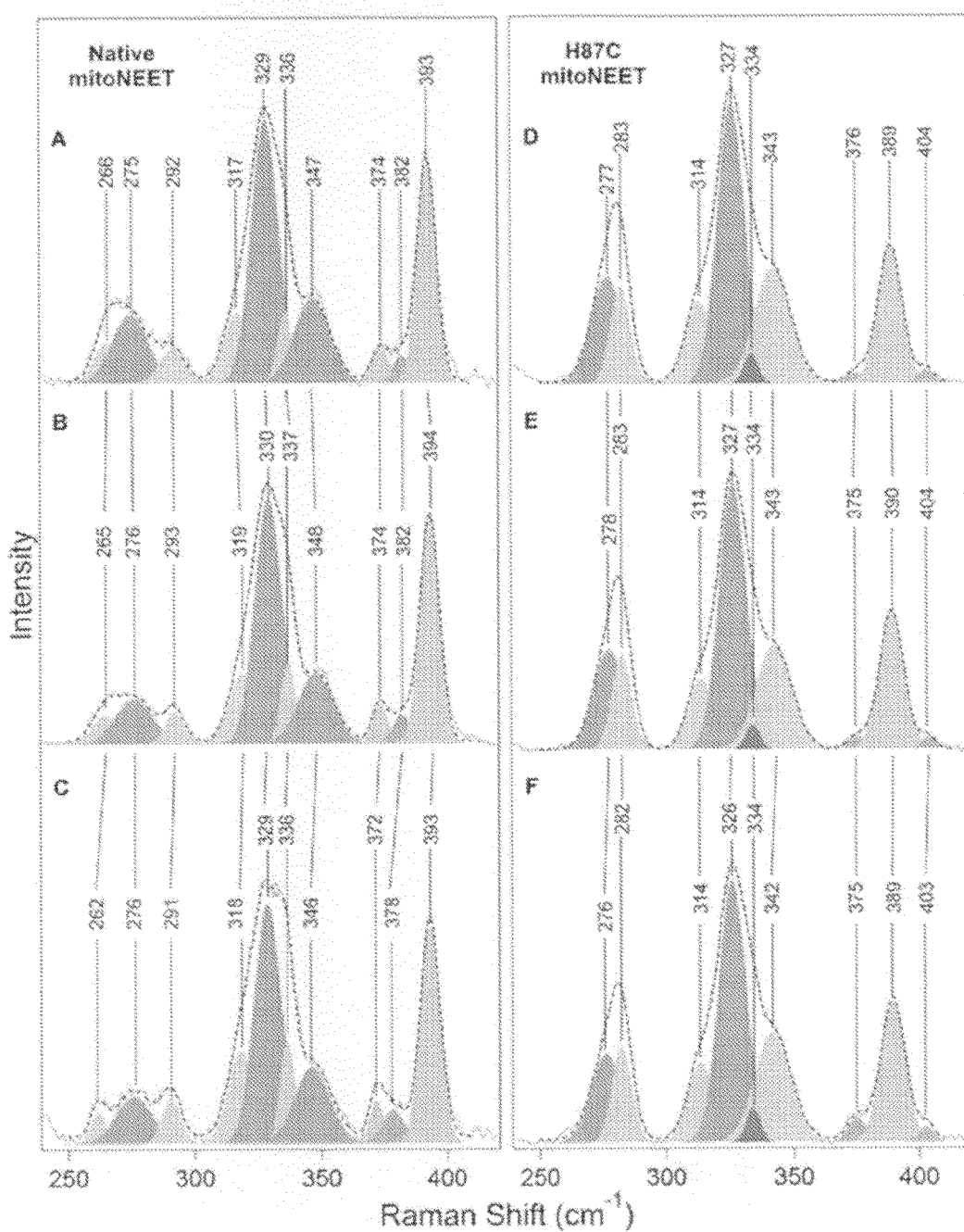
FIG. 12 shows resonance Raman spectra for native mitoNEET and mutant H87C mitoNEET.

Resonance Raman spectra of native and H87C mitoNEET were obtained at pH values 7.5, 7.0, and 6.2. The spectra, shown in FIG. 12, can be divided into three regions for consideration: region I (250-300 cm$^{-1}$); region II (300-360 cm$^{-1}$); and region III (360-420 cm$^{-1}$). The most significant spectral changes as a function of pH were observed in region I. FIG. 12(A-C) shows decomposition of region I of native mitoNEET into three Gaussian bands. Upon decreasing the pH from 7.5 to 6.2, a peak shifted from 266 to 262 cm$^{-1}$, but the energies of the other two bands remained relatively constant at ~276 and 292 cm$^{-1}$. The relative intensities of the 275 cm$^{-1}$ to the 266 and 292 cm$^{-1}$ bands also showed a pH dependence. Upon decreasing the pH from 7.5 to 7.0 and then to 6.2, the $I_{275}/I_{266}$ ratio decreased from 1.69 to 1.58 and then to 1.51. Over the same intervals, the $I_{275}/I_{292}$ ratio decreased considerably from 2.04 to 1.40 and to 1.07. Finally, the ratio of the 292 cm$^{-1}$ to 266 cm$^{-1}$ band shifted from 0.83 (pH 7.5) to 1.34 (pH 6.2).

Regions II and III showed subtle changes. Region II was decomposed into four bands; no systematic shifts were observed and the peak positions remained unchanged as a function of pH. However, some relative intensity variations were observed. For example, the intensity ratio of the middle two peaks changed with pH. This shift in relative intensities was evident in the raw spectra in the form of a sharp peak (~329 cm$^{-1}$) in pH 7.5 that evolved to a plateau at pH 6.2. Region III was decomposed into three bands; the two bands at 374 and 382 cm$^{-1}$ (pH 7.5) shifted to lower energy (372 and 378 cm$^{-1}$, respectively) at pH 6.2 while the band at 393 cm$^{-1}$ remained constant. The relative intensities in this region were unchanged.

FIG. 12(D-F) shows the complete Gaussian decomposition of H87C at three different pH values. Compared to the native protein, the H87C displayed only minimal changes with pH. Region I required two Gaussian bands because of the asymmetry of the observed band. The peak positions and intensity ratios showed minimal variability as the pH was decreased from 7.5 7 to 6.2; the intensity ratio $I_{283}/I_{277}$ changes from 0.9 to 1.1. The feature found in region II decomposed successfully into four bands, and the locations and intensities did not vary as a function of pH. Region III was likewise invariant; this region decomposed into three bands whose positions and relative intensities were essentially pH-independent.

Effects of Bound Pioglitazone on the Resonance Raman Spectra of mitoNEET

Figure 13:
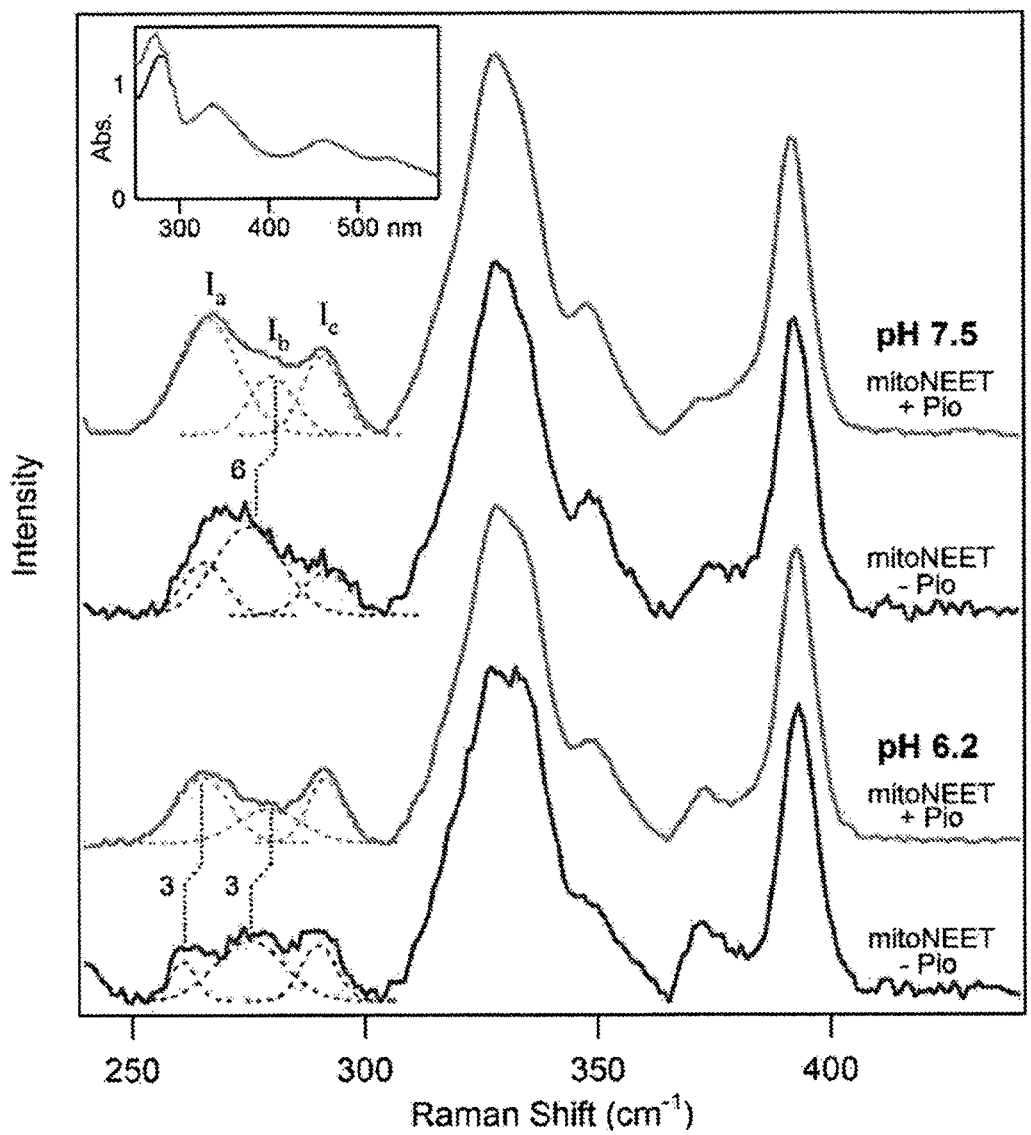
FIG. 13 shows resonance Ramen spectra for mitoNEET at pH 7.5 and pH 6.2 in the presence and absence of pioglitazone. Dashed lines represent Gaussian decompositions. All peak shifts on drug addition in region 1 greater than 1 $cm^{-1}$ are shown. Roman numerals identify peaks $I_a$, $I_b$ and $I_c$. The inset shows the absorption spectrum of 100 μM mitoNEET in the presence (gray line) and absence (black line) of pioglitazone. The increase in absorbance is due to pioglitazone.

Resonance Raman spectra of mitoNEET at pH 7.5 and pH 6.2 were obtained in the presence and absence of pioglitazone (FIG. 13). At pH 7.5, two of the bands (267 and 292 cm$^{-1}$) in region I were found at energies similar to those observed in the absence of the drug (266 and 292 cm$^{-1}$). The center band, at 275 cm$^{-1}$, shifted to a higher energy and appeared at 281 cm$^{-1}$ in the presence of the drug. In addition to this shift in peak position, major differences were observed in the relative intensities (summarized in Table 4). Table 4 shows the intensity ratio changes of native mitoNEET at pH 7.5 and 6.2 in the absence (−) and presence (+) of pioglitazone (Pio). Peaks $I_a$, $I_b$, and $I_c$ are as noted on FIG. 13.

TABLE 4

| Intensity Ratio | pH 7.5 | | pH 6.2 | |
| --- | --- | --- | --- | --- |
|  | −Pio | +Pio | −Pio | +Pio |
| $I_a/I_b$ | 1.7 | 0.5 | 1.5 | 0.5 |
| $I_a/I_c$ | 2.0 | 0.8 | 1.1 | 0.5 |

While the center band (275 cm$^{-1}$) had the greatest intensity without pioglitazone, its relative intensity diminished greatly upon addition of the drug. In the absence of drug, the relative intensities $I_{275}/I_{267}$ and $I_{275}/I_{292}$ were 1.7 and 2.0, respectively. Binding of the drug altered these ratios to 0.5 and 0.8, respectively. Region II remained largely unchanged upon drug-binding; band positions fluctuated less than 1 cm$^{-1}$ and relative intensities varied less than 7%. Region III also displayed only minimal alterations in band positions upon binding of the drug. However, changes in relative intensities were observed upon addition of drug; specifically, the ratio $I_{374}/I_{382}$ cm$^{-1}$ shifted from 1.3 to 0.7 in the presence of drug.

At pH 6.2, region I exhibited similar changes to those observed at pH 7.5. The band at 276 cm$^{-1}$ shifted to higher energy and was observed at 279 cm$^{-1}$. The peak at 262 cm$^{-1}$ also shifted to 265 cm$^{-1}$. Although a shift in the location of this peak was not observed at pH 7.5, in the absence of the drug, the peak was observed at lower energy at pH 6.2 compared to pH 8 7.5. Modifications in intensity ratios were similar to those seen at pH 7.5. While the relative intensity ratios $I_{276}/I_{262}$ and $I_{276}/I_{291}$ were 1.5 and 1.1 in the absence of pioglitazone, addition of the drug decreased both of these ratios to 0.5. The spectra of mitoNEET with and without pioglitazone in region II were essentially equivalent. The one notable change in region III was the shift of the peak at 378 cm$^{-1}$ to 382 cm$^{-1}$ upon addition of pioglitazone. In addition, $I_{372}/I_{378}$ decreased, as was observed at pH 7.5.

The naturally occurring $Fe_2S_2(His)(Cys)_3$ motif in mitoNEET is unique. While several related and engineered ferredoxin-like and Rieske-like molecules have been studied by a variety of spectroscopic techniques, including resonance Raman, X-ray absorption, and circular dichroism, the current example is the first resonance Raman study of a naturally occurring (His)(Cys)$_3$ binding motif in 2Fe-2S cluster binding proteins (Kounosu, A. et al. J. Biol. Chem 2004, 279, 19-12528; Yachandra, V. K. et al. J. Am Chem. Soc. 1983, 105, 6462-6468; Kuila, D. et al. Biochim. Biophys. Acta 1992, 1140, 175-183; Kuila, D. et al. J. Am. Chem. Soc. 1987, 109, 1559-1561; Spiro, T. G. et al. In Biological Applications of Raman Spectroscopy; Spiro, T. G., Ed. 1988, Vol. 3, p. 523-553; Rose, K. et al. J. Am Chem. Soc. 1999, 121, 2353-2363; Cosper, N. J. et al. Prot. Sci. 2002, 11, 2969-2973; Iwasaki, T. et al J. Biol. Chem. 1996, 271, 27659-27663, Fu, W. G. et al. J. Biol. Chem. 1992, 267, 15502-15510). The visible absorption bands of Rieske proteins, ferredoxins, and presumably mitoNEET arise from a ligand-to-metal charge transfer, and Fe—S and Fe—N normal modes are observed in resonance Raman spectroscopy (Yachandra, V. K. et al. J. Am Chem. Soc. 1983, 105, 6462-6468; Rotsaert, F. A. J. et al. J. Biol. Inorg. Chem. 2003, 8, 318-326; Han, S. et al. J. Am. Chem. Soc. 1989, 111, 3505-3511; Kuila, D. et al. Biochim. Biophys. Acta 1992, 1140, 175-183; Fu, W. G. et al. J. Biol. Chem. 1992, 267, 15502-15510; Tang, S. P. W. et al. Biochem. Biophys. Res. Comm 1973, 53, 869-874). The absorption spectra of native and H87C mutant mitoNEET are similar at wavelengths above 500 nm (FIG. 11, inset). In addition, the absorption spectra of native mitoNEET with and without pioglitazone are identical in the visible region (FIG. 13, inset). Because of the similarity in absorption cross-sections at the excitation wavelength of 514 nm, we do not anticipate major alterations in Raman scattering intensities due to changes in enhancement factors.

Primary Modes of Interest with Fe—N Vibrations

Figure 14:
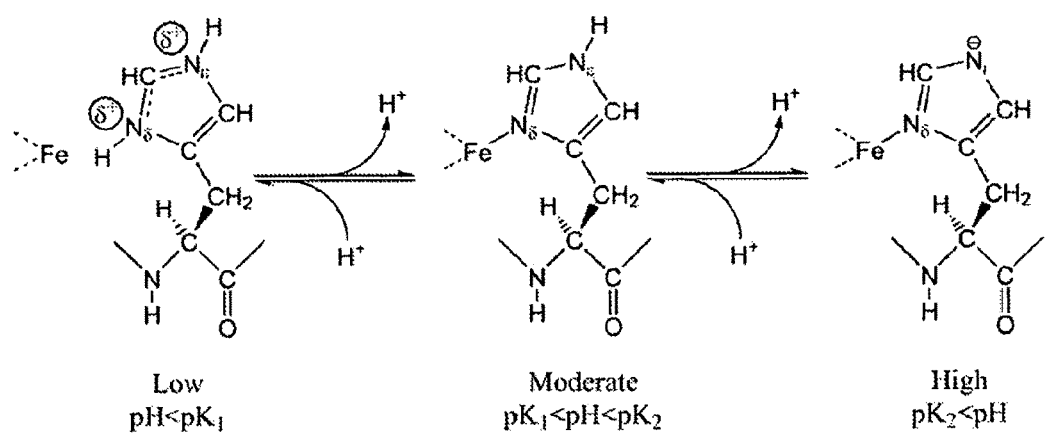
FIG. 14 shows a scheme for the pH mediated effects of on histidine protonation states. $pK_1$ and $pK_2$ are the $N_\delta$ and $N_\epsilon$ $pK_a$ values, respectively. $pK_1$ is generally ~6 in solution and $pK_2$ can be 7.5-11.5 in Rieske centers.

Primary modes of interest are those with contributions from Fe—N vibrations and are expected to be found in the 200-300 cm$^{-1}$ region, and other work on Rieske proteins have made Fe—N mode assignments in the 266-300 cm$^{-1}$ region (Kuila, D.; Fee, J. A.; Schoonover, J. R.; Woodruff, W. H.; Batie, C. J.; Ballou, D. P.; J. Am. Chem. Soc. 1987, 109, 1559-1561; Kuila, D.; Schoonover, J. R.; Dyer, R. B.; Batie, C. J.; Ballou, D. P.; Fee, J. A.; Woodruff, W. H.; Biochim. Biophys. Acta 1992, 1140, 175-183; Iwasaki, T.; Imai, T.; Urushiyama, A.; Oshima, T.; J. Biol. Chem. 1996, 271, 27659-27663). Specifically, the peak near 266 cm$^{-1}$ is attributed to having contributions from the neutral ligating histidine, shown as the "moderate pH" species in FIG. 14. Other studies have also suggested the presence of Fe—S peaks in this region (Rotsaert, F. A. J.; Pikus, J. D.; Fox, B. G.; Markley, J. L.; Sanders-Loehr, J.; J. Biol. Inorg. Chem. 2003, 8, 318-326; Kounosu, A.; Li, Z. R.; Cosper, N. J.; Shokes, J. E.; Scott, R. A.; Imai, T.; Urushiyama, A.; Iwasaki, T.; J. Biol. Chem 2004, 279, 19-12528). These other studies, coupled to the disappearance of the band near 265 cm$^{-1}$ in the H87C mutant, make it feasible to tentatively assign 265 cm$^{-1}$ as a mode with significant Fe—N contribution. With a $pK_a$ value of 6.0-6.5 when not bound to a metal, the population of doubly protonated histidine residues should increase as pH decreases, shown in FIG. 14 (Yue, K. T.; Lee, M. H.; Zheng, J.; Callender, R.; Biochim. Biophys. Acta 1991, 1078, 296-302). The current observation that the relative intensity of the 265 cm$^{-1}$ peak decreases with a drop in pH is consistent with this prediction and further supports the claim that the 265 cm$^{-1}$ is heavily influenced by Fe—N motion.

The intensity of the 275 cm$^{-1}$ mode also decreases as a function of pH. Therefore, it is likely that this mode is sensitive to the protonation state of the ligating histidine group. However, its persistence in the H87C mutant spectra implies that its nature is more complicated than a pure Fe—N mode. Neutral and high-pH resonance Raman studies of Rieske-type proteins have reported pH-dependent changes in the spectra that were attributed to a change in protonation state of the ligating histidine $N_\epsilon$ atom (FIG. 14) (Kuila, D.; Schoonover, J. R.; Dyer, R. B.; Batie, C. J.; Ballou, D. P.; Fee, J. A.; Woodruff, W. H.; Biochim. Biophys. Acta 1992, 1140, 175-183; Kuila, D.; Fee, J. A.; Schoonover, J. R.; Woodruff, W. H.; Batie, C. J.; Ballou, D. P.; J. Am. Chem. Soc. 1987, 109, 1559-1561; Iwasaki, T.; Imai, T.; Urushiyama, A.; Oshima, T.; J. Biol. Chem. 1996, 271, 27659-27663). Kuila et al. suggested that the binding of Fe to the $N_\delta$ atom of histidine in Rieske proteins lowers the $pK_a$ of $N_\epsilon$ to ~9, thereby rationalizing the assignment of the peak near ~274 $cm^{-1}$ to the Fe—N stretch of a deprotonated, ligating histidine residue (Kuila, D.; Schoonover, J. R.; Dyer, R. B.; Batie, C. J.; Ballou, D. P.; Fee, J. A.; Woodruff, W. H.; Biochim. Biophys. Acta 1992, 1140, 175-183). Other studies, based on both experiment and calculation, have determined histidine $N_\epsilon$ $pK_a$ values for Rieske proteins ranging from 7.5-11.5 (Lin, I. J.; Chen, Y.; Fee, J. A.; Song, J. K.; Westler, W. M.; Markley, J. L.; J. Am. Chem. Soc. 2006, 128, 10672-10673; Klingen, A. R.; Ullmann, G. M.; Biochemistry 2004, 43, 12383-12389). Another report contradicted the assignment of 274 $cm^{-1}$ to Fe—N(deprotonated) and instead attributed it to backbone deformations (Iwasaki, T.; Kounosu, A.; Kolling, D. R. J.; Crofts, A. R.; Dikanov, S. A.; Jin, A.; Imai, T.; Urushiyama, A.; J. Am Chem Soc. 2004, 126, 4788-4789). Since the conditions of the experiments here reported are unlikely to result in deprotonatation of the ligating histidine residue, the possibility that the 275 $cm^{-1}$ peak arises from an anionic histidine ligand is excluded. Therefore, is it noted that there are at least two possible interpretations of the 275 $cm^{-1}$ peak. First, this peak may reflect a mode that is primarily composed of Fe—S vibration and is highly sensitive to the protonation state of the ligating histidine residue; its persistence in H87C is consistent with this interpretation. Alternatively, the 275 $cm^{-1}$ mode may primarily reflect the Fe—N (neutral histidine) moiety that disappears in H87C; a new Fe—S peak then appears in the same region in the H87C spectrum.

The final peak in region I of native mitoNEET is located near 292 $cm^{-1}$. Based on other assignments of Fe—S modes and the observed invariance of this peak position or intensity as a function of pH, the 292 $cm^{-1}$ peak is tentatively assigned to an Fe—S mode (Yachandra, V. K.; Hare, J.; Gewirth, A.; Czernuszewicz, R. S.; Kimura, T.; Holm, R. H., Spiro, T. G.; J. Am Chem. Soc. 1983, 105, 6462-6468; Rotsaert, F. A. J.; Pikus, J. D.; Fox, B. G.; Markley, J. L.; Sanders-Loehr, J.; J. Biol. Inorg. Chem. 2003, 8, 318-326; Han, S.; Czernuszewicz, R. S.; Kimura, T.; Adams, M. W. W.; Spiro, T. G.; J. Am. Chem. Soc. 1989, 111, 3505-3511, Fu, W. G.; Drozdzewski, P. M.; Davies, M. D.; Sligar, S. G.; Johnson, M. K.; J. Biol. Chem. 1992, 267, 15502-15510; Tang, S. P. W.; Spiro, T. G.; Mukai, K.; Kimura, T.; Biochem. Biophys. Res. Comm 1973, 53, 869-874). The absence of a 292 $cm^{-1}$ mode in the H87C mutant may be explained by (1) the 292 $cm^{-1}$ mode shifts to 283 $cm^{-1}$ upon the H87 C mutation; or (2) the change in symmetry of the metal cluster results in different sets of Raman-active modes. Peaks in this ~290 $cm^{-1}$ area have been observed in ferredoxins and ferredoxin model complexes and therefore support our tentative assignment of the 292 $cm^{-1}$ mode to the Fe—S group (Yachandra, V. K.; Hare, J.; Gewirth, A.; Czernuszewicz, R. S.; Kimura, T.; Holm, R. H., Spiro, T. G.; J. Am Chem. Soc. 1983, 105, 6462-6468).

The relative intensity variations of the Fe—N peaks in region I suggest that the changes to the nature of the Fe—N bond that occur with decreasing pH compose an integral step of the process that leads to the loss of the active cluster, a process evidenced by the disappearance of visible absorption. There are three additional histidine residues in each monomer unit of mitoNEET: H90 is located within 10 Å of the 2Fe-2S cluster while the H48 and H58 side chains are located >10 Å from the metal cluster. Based on the fact that the H87C mutant, which still contains these 3 peripheral His residues, showed no major spectral changes as a function of pH, it is unlikely that global protein conformational changes arising from protonation of one of the non-ligating histidine residues is independently responsible for the loss in metal cluster or observed changes in native mitoNEET resonance Raman spectra.

Energetic considerations and previous work with ferredoxins and Rieske-type proteins, suggest that regions II and III are expected to be composed primarily of Fe—S modes (Yachandra, V. K.; Hare, J.; Gewirth, A.; Czernuszewicz, R. S.; Kimura, T.; Holm, R. H., Spiro, T. G.; J. Am Chem. Soc. 1983, 105, 6462-6468; Rotsaert, F. A. J.; Pikus, J. D.; Fox, B. G.; Markley, J. L.; Sanders-Loehr, J.; J. Biol. Inorg. Chem. 2003, 8, 318-326; Han, S.; Czernuszewicz, R. S.; Kimura, T.; Adams, M. W. W.; Spiro, T. G.; J. Am. Chem. Soc. 1989, 111, 3505-3511; Kuila, D.; Schoonover, J. R.; Dyer, R. B.; Batie, C. J.; Ballou, D. P.; Fee, J. A.; Woodruff, W. H.; Biochim. Biophys. Acta 1992, 1140, 175-183; Kuila, D.; Fee, J. A.; Schoonover, J. R.; Woodruff, W. H.; Batie, C. J.; Ballou, D. P.; J. Am. Chem. Soc. 1987, 109, 1559-1561; Han, S.; Czernuszewicz, R. S.; Spiro, T. G.; J. Am. Chem. Soc. 1989, 111, 3496-3504). The observed invariance in peak positions and relative intensities at all pH values between the native and H87C forms of mitoNEET supports these assignments for mitoNEET. Disappearance of the peak near 382 $cm^{-1}$ and appearance of a new peak near 404 $cm^{-1}$ upon replacement of the ligating His87 to Cys in mitoNEET may be explained in terms of a peak shift from 382 to 404 $cm^{-1}$. The 382 and 404 $cm^{-1}$ peaks are beyond the expected energy range for Fe—N modes, and therefore likely reflect Fe—S vibrations. These and other observed alterations of Fe—S modes upon ligand replacement are likely due to changes in cluster geometry.

Resonance Raman changes were observed upon addition of pioglitazone (FIG. 13). At both pH 7.5 and 6.2, addition of pioglitazone altered region I. Specifically, the relative intensity of the Fe—N peak near 265 $cm^{-1}$ increased while the peak near 275 $cm^{-1}$ decreased. Additionally, the intensity of the peak near 292 $cm^{-1}$ increased. As demonstrated herein, the addition of pioglitazone enhances the stability of the cluster, suggesting that the drug inhibits the rate of cluster release. The observed rise in the 265 $cm^{-1}$ band intensity upon drug-binding supports this idea; it may decrease the $pK_a$ of the $N_\delta$ histidine thereby increasing the steady state population of stable mitoNEET species. Crystal structure data indicate that the H87 side chain is approximately 35% surface exposed, making direct interaction between the side chain and TZDs a distinct possibility. Alternatively, drug binding may directly alter the metal cluster structure such that scattering cross-sections are modified or binding may occur allosterically and indirectly alter geometry of the metal cluster via global protein conformational changes. However, since no changes in the optical spectra of mitoNEET+pioglitazone were observed at wavelengths above 300 nm, these two mechanisms are considered to be less likely than the first proposed. Other minor shifts in peak positions and intensities are observed in regions II and III.

Example 3

MitoNEET Protein in the Livers of Diabetic Rats Treated with Rosiglitazone

MitoNEET levels in the livers of diabetic rats correlates with the measured blood glucose in control and rosiglitazone-treated rats, further establishing the involvement of mitoNEET in diabetes. The mitoNEET protein level were examined in liver tissues obtained from diabetic ZDF rats treated or not treated (control) with rosiglitazone.

Animal Study

Sixteen male ZDF rats were housed in filter cages, 2 or 3 animals per cage. Weight and blood glucose levels were measured every week. The blood glucose was measured at the fed state (07:30 am) and after 6 hours fast (1:30 μm). The Animals were divided into two groups: a control group, and a rosiglitazone-treated group. Animals were treated daily for 3 weeks once a day, 5 times a week, with rosiglitazone, 10 mg/kg by gavage (0.7 ml) for the rosi-treated rats; or 0.7 ml saline for the control rats. After three weeks, liver, muscle and epididymal fat were collected and immediately frozen.

Summary of the Glucose Blood Levels

Figure 15:
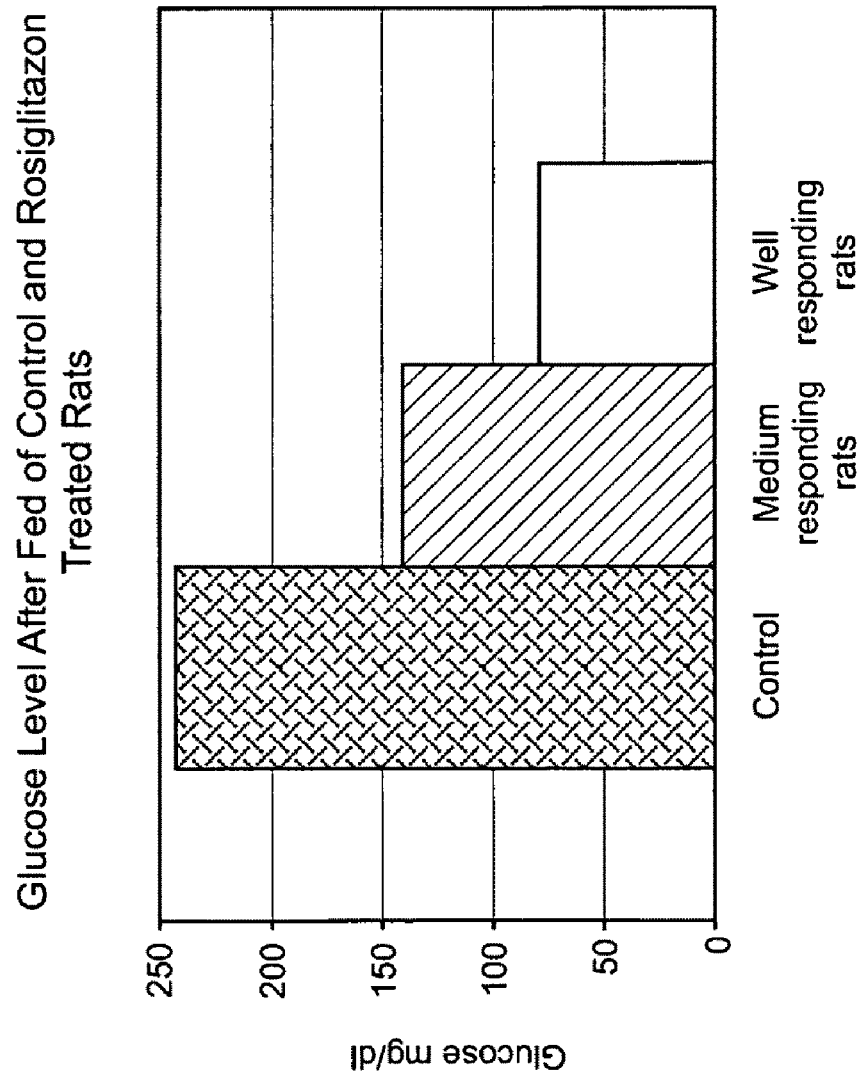
FIG. 15 shows a graph of the glucose levels in rosiglitazone-treated and untreated diabetic rats.

The average glucose blood level after fed of the control group was >240 mg/dl; in the rosiglitazone-treated rats some responded in a medium manner to the treatment; after three weeks of rosiglitazone treatment their glucose blood levels after fed was ~120-140 mg/dl and some rats responded very well to rosiglitazone treatment and after three weeks their glucose blood levels after fed was ~80 mg/dl. The average levels of blood glucose in these three groups are shown in FIG. 15.

Extraction of Total Proteins from Livers of Control and Rosiglitazone-Treated Rats From each rat liver, a piece about 100 mg of tissue was homogenized in liquid nitrogen to microscopic pieces (like sand) and resuspended in ~800 μl of STN buffer (0.4 M Sucrose; 10 mM Tricin-NaOH, pH 8.0; 10 mM NaCl that contained 1 mM of PMSF Amino Caproic Acid and Benzamidine). Homogenized samples were stored in liquid nitrogen till their sonication. Sonication was for 5 cycles of 30 seconds each, on ice. The protein concentration of each sample was determined by the Bradford Protein Assay and samples at equal protein concentration were taken. To ~100 μl sample, SDS and BME were added, to a final concentration of 2%. Samples were incubated for 1 hour at 37° C. SDS-PAGE dissociation buffer was added and the samples were further incubated for 1 hour at 50° C.

Western Blots Analysis with Anti-mitoNEET Antibody

Figure 16:
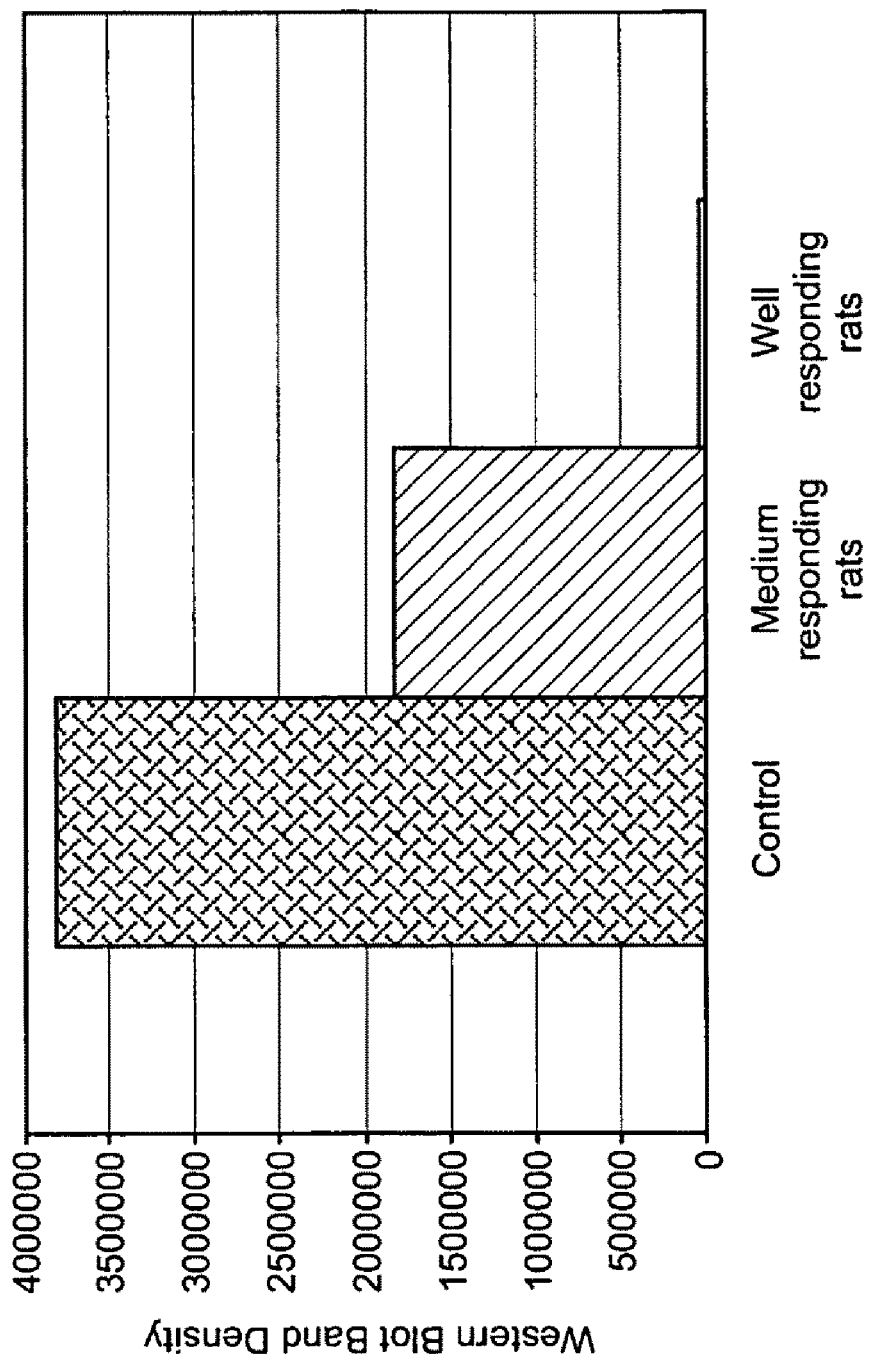
FIG. 16 shows a graph of a Western blot analysis of mitoNEET levels in rosiglitazone-treated and untreated diabetic rats.

A 12% SDS-PAGE gel was loaded with samples, molecular weight markers, and pure mitoNEET controls. The total protein applied to each lane varied from 50 μg to 150 μg. Each gel was run in duplicate; one gel was stained be Commassie blue and the other gel was electro transferred. Electro-transfer was in a semi-dry cell for 30-45 minutes transfer at 15 V and 2 mA. The latter was incubated (1 hour) with blocking buffer, followed by 2 hours incubation with anti-mitoNEET at 1:125 dilution followed by incubation with Goat anti-rabbit second antibody. ECL reagent was used to detect the antibody-antigen reaction in the Image reader of Fuji. The density at each detected band was evaluated by the specific software. FIG. 16 indicates the density of representatives of the anti-mitoNEET-mitoNEET interacting bands in the three rats groups; control; medium; well responding rats to rosiglitazone-treatment.

All the analyzed results exhibited the same pattern: control diabetic rats that were not treated with rosiglitazone maintained high blood glucose and showed high mitoNEET levels; rats that responded in a medium manner to the rosiglitazone-treatment with respect to their blood glucose levels, showed medium mitoNEET levels; and rat that responded well to the rosiglitazone-treatment with respect to their blood glucose levels, showed very low mitoNEET levels. Accordingly, mitoNEET levels in the livers of diabetic rats correlates with the measured blood glucose in control and rosiglitazone-treated rats, further establishing the involvement of mitoNEET in diabetes.

The above description discloses subject matter including several embodiments for methods and compositions. This subject matter is susceptible to modification, and such modifications will become apparent to those skilled in the art from a consideration of this description and/or practice of the embodiments disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, literature references and web-sites, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

TABLE 2

| HEADER | | XX-XXX-XX xxxx | |
|---|---|---|---|
| COMPND | | | |
| REMARK | 3 | | |
| REMARK | 3 | REFINEMENT. | |
| REMARK | 3 | PROGRAM: | REFMAC 5.2.0005 |
| REMARK | 3 | AUTHORS: | MURSHUDOV, VAGIN, DODSON |
| REMARK | 3 | | |
| REMARK | 3 | REFINEMENT TARGET: | MAXIMUM LIKELIHOOD |
| REMARK | 3 | | |
| REMARK | 3 | DATA USED IN REFINEMENT. | |
| REMARK | 3 | RESOLUTION RANGE HIGH (ANGSTROMS): | 1.50 |
| REMARK | 3 | RESOLUTION RANGE LOW (ANGSTROMS): | 59.03 |
| REMARK | 3 | DATA CUTOFF (SIGMA(F)): | NONE |
| REMARK | 3 | COMPLETENESS FOR RANGE (%): | 95.25 |
| REMARK | 3 | NUMBER OF REFLECTIONS: | 20398 |
| REMARK | 3 | | |
| REMARK | 3 | FIT TO DATA USED IN REFINEMENT. | |
| REMARK | 3 | CROSS-VALIDATION METHOD: | THROUGHOUT |
| REMARK | 3 | FREE R VALUE TEST SET SELECTION: | RANDOM |
| REMARK | 3 | R VALUE (WORKING + TEST SET): | 0.18417 |
| REMARK | 3 | R VALUE (WORKING SET): | 0.18213 |
| REMARK | 3 | FREE R VALUE: | 0.22228 |
| REMARK | 3 | FREE R VALUE TEST SET SIZE (%): | 5.0 |
| REMARK | 3 | FREE R VALUE TEST SET COUNT: | 1081 |
| REMARK | 3 | | |
| REMARK | 3 | FIT IN THE HIGHEST RESOLUTION BIN. | |
| REMARK | 3 | TOTAL NUMBER OF BINS USED: | 20 |
| REMARK | 3 | BIN RESOLUTION RANGE HIGH : | 1.503 |
| REMARK | 3 | BIN RESOLUTION RANGE LOW: | 1.542 |
| REMARK | 3 | REFLECTION IN BIN (WORKING SET): | 1121 |
| REMARK | 3 | BIN COMPLETENESS (WORKING + TEST) (%): | 71.28 |
| REMARK | 3 | BIN R VALUE (WORKING SET) : | 0.369 |
| REMARK | 3 | BIN FREE R VALUE SET COUNT: | 48 |
| REMARK | 3 | BIN FREE R VALUE: | 0.430 |
| REMARK | 3 | | |
| REMARK | 3 | NUMBER OF NON-HYDROGEN ATOMS USED IN REFINEMENT. | |
| REMARK | 3 | ALL ATOMS. | 1206 |
| REMARK | 3 | | |
| REMARK | 3 | B VALUES. | |
| REMARK | 3 | FROM WILSON PLOT ($A^{**}2$) : | NULL |
| REMARK | 3 | MEAN B VALUE (OVERALL, $A^{**}2$) : | 33.147 |
| REMARK | 3 | OVERALL ANISOTROPIC B VALUE. | |
| REMARK | 3 | B11 ($A^{**}2$): | 1.37 |
| REMARK | 3 | B22 ($A^{**}2$): | 1.52 |
| REMARK | 3 | B33 ($A^{**}2$): | -2.89 |
| REMARK | 3 | B12 ($A^{**}2$): | 0.00 |
| REMARK | 3 | B13 ($A^{**}2$): | 0.00 |
| REMARK | 3 | B23 ($A^{**}2$): | 0.00 |
| REMARK | 3 | | |
| REMARK | 3 | ESTIMATED OVERALL COORDINATE ERROR. | |
| REMARK | 3 | ESU BASED ON R VALUE (A): | 0.079 |

TABLE 2-continued

| | | | | | | |
|---|---|---|---|---|---|---|
| REMARK | 3 | ESU BASED ON FREE R VALUE | (A): | | | 0.084 |
| REMARK | 3 | ESU BASED ON MAXIMUM LIKELIHOOD | (A): | | | 0.079 |
| REMARK | 3 | ESU FOR B VALUES BASED ON MAXIMUM LIKELIHOOD | (A**2): | | | 4.667 |
| REMARK | 3 | | | | | |
| REMARK | 3 | CORRELATION COEFFICIENTS. | | | | |
| REMARK | 3 | CORRELATION COEFFICIENT FO-FC : | | | | 0.972 |
| REMARK | 3 | CORRELATION COEFFICIENT FO-FC FREE : | | | | 0.955 |
| REMARK | 3 | | | COUNT | RMS | WEIGHT |
| REMARK | 3 | RMS DEVIATIONS FROM IDEAL VALUES | | | | |
| REMARK | 3 | BOND LENGTHS REFINED ATOMS | (A): | 1101; | 0.012 | 0.021 |
| REMARK | 3 | BOND LENGTHS OTHERS | (A): | 958; | 0.001 | 0.020 |
| REMARK | 3 | BOND ANGLES REFINED ATOMS | (DEGREES): | 1485; | 1.704 | 1.936 |
| REMARK | 3 | BOND ANGLES OTHERS | (DEGREES): | 2254; | 0.830 | 3.000 |
| REMARK | 3 | TORSION ANGLES, PERIOD 1 | (DEGREES): | 139; | 6.431 | 5.000 |
| REMARK | 3 | TORSION ANGLES, PERIOD 2 | (DEGREES): | 54; | 21.135; | 25.000 |
| REMARK | 3 | TORSION ANGLES, PERIOD 3 | (DEGREES): | 198; | 12.224; | 15.000 |
| REMARK | 3 | TORSION ANGLES, PERIOD 4 | (DEGREES): | 4; | 6.117; | 15.000 |
| REMARK | 3 | CHIRAL-CENTER RESTRAINTS | (A**3): | 153; | 0.080; | 0.200 |
| REMARK | 3 | GENERAL PLANES REFINED ATOMS | (A): | 1227; | 0.006; | 0.020 |
| REMARK | 3 | GENERAL PLANES OTHERS | (A): | 211; | 0.001; | 0.020 |
| REMARK | 3 | NON-BONDED CONTACTS REFINED ATOMS | (A): | 186; | 0.187; | 0.200 |
| REMARK | 3 | NON-BONDED CONTACTS OTHERS | (A): | 930; | 0.187; | 0.200 |
| REMARK | 3 | NON-BONDED TORSION REFINED ATOMS | (A): | 511; | 0.169; | 0.200 |
| REMARK | 3 | NON-BONDED TORSION OTHERS | (A): | 578; | 0.084; | 0.200 |
| REMARK | 3 | H-BOND (X...Y) REFINED ATOMS | (A): | 97; | 0.151; | 0.200 |
| REMARK | 3 | SYMMETRY VDW REFINED ATOMS | (A): | 6; | 0.150; | 0.200 |
| REMARK | 3 | SYMMETRY VDW OTHERS | (A): | 21; | 0.229; | 0.200 |
| REMARK | 3 | SYMMETRY H-BOND REFINED ATOMS | (A): | 5; | 0.101; | 0.200 |
| REMARK | 3 | | | COUNT | EMS | WEIGHT |
| REMARK | 3 | ISOTROPIC THERMAL FACTOR RESTRAINTS. | | | | |
| REMARK | 3 | MAIN-CHAIN BOND REFINED ATOMS | (A**2): | 720; | 1.370; | 2.000 |
| REMARK | 3 | MAIN-CHAIN BOND OTHER ATOMS | (A**2): | 275; | 0.289; | 2.000 |
| REMARK | 3 | MAIN-CHAIN ANGLE REFINED ATOMS | (A**2): | 1076; | 1.946; | 4.000 |
| REMARK | 3 | SIDE-CHAIN BOND REFINED ATOMS | (A**2): | 476; | 3.014; | 6.000 |
| REMARK | 3 | SIDE-CHAIN ANGLE REFINED ATOMS | (A**2): | 401; | 3.793; | 8.000 |
| REMARK | 3 | | | | | |
| REMARK | 3 | NCS RESTRAINTS STATISTICS | | | | |
| REMARK | 3 | NUMBER OF NCS GROUPS : NULL | | | | |
| REMARK | 3 | | | | | |
| REMARK | 3 | TLS DETAILS | | | | |
| REMARK | 3 | NUMBER OF TLS GROUPS : | 2 | | | |
| REMARK | 3 | ATOM RECORD CONTAINS RESIDUAL B FACTORS ONLY | | | | |
| REMARK | 3 | | | | | |
| REMARK | 3 | TLS GROUP : | 1 | | | |
| REMARK | 3 | NUMBER OF COMPONENTS GROUP : | 1 | | | |
| REMARK | 3 | COMPONENTS | C | | | |
| REMARK | 3 | RESIDUE RANGE : | A | SSSEQI | TO | C A SSSEQI |
| REMARK | 3 | | | 11 | | 500 |
| REMARK | 3 | ORIGIN FOR THE GROUP (A): | | 11.9410 | 45.1180 | 7.8980 |
| REMARK | 3 | T TENSOR | | | | |
| REMARK | 3 | T11: | −0.1619 | T22: | −0.2019 | |
| REMARK | 3 | T33: | −0.0925 | T12: | 0.0267 | |

TABLE 2-continued

| REMARK | 3 | T13: | 0.0149 | T23: | 0.0208 | | | |
|---|---|---|---|---|---|---|---|---|
| REMARK | 3 | L TENSOR | | | | | | |
| REMARK | 3 | L11: | 2.0124 | L22: | 1.4178 | | | |
| REMARK | 3 | L33: | 5.4379 | L12: | -0.0542 | | | |
| REMARK | 3 | L13: | -1.2794 | L23: | -0.1810 | | | |
| REMARK | 3 | S TENSOR | | | | | | |
| REMARK | 3 | S11: | -0.1523 | S12: | 0.0083 | S13: | | |
| REMARK | 3 | S21: | -0.0309 | S22: | -0.0947 | S23: | | |
| REMARK | 3 | S31: | 0.4323 | S32: | 0.2102 | S33: | | |
| REMARK | 3 | TLS GROUP: | | | 2 | | | |
| REMARK | 3 | NUMBER OF COMPONENTS GROUP: | | | 1 | | | |
| REMARK | 3 | COMPONENTS | | | C | | SSSEQI | | SSSEQI |
| REMARK | 3 | RESIDUE RANGE: | | | B | | 11 | TO | 500 |
| REMARK | 3 | ORIGIN FOR THE GROUP (A): | | | | | 10.8060 | 54.5660 | 5.6070 |
| REMARK | 3 | T TENSOR | | | | | | | |
| REMARK | 3 | T11: | -0.2002 | T22: | -0.2409 | | | |
| REMARK | 3 | T33: | -0.0798 | T12: | 0.0510 | | | |
| REMARK | 3 | T13: | -0.0160 | T23: | 0.0335 | | | |
| REMARK | 3 | L TENSOR | | | | | | | |
| REMARK | 3 | L11: | 3.0499 | L22: | 1.4775 | | | |
| REMARK | 3 | L33: | 6.7538 | L12: | 0.5740 | | | |
| REMARK | 3 | L13: | -1.7590 | L23: | 0.3674 | | | |
| REMARK | 3 | S TENSOR | | | | | | | |
| REMARK | 3 | S11: | -0.0123 | S12: | 0.0576 | S13: | | 0.1009 |
| REMARK | 3 | S21: | -0.0225 | S22: | -0.0892 | S23: | | -0.0749 |
| REMARK | 3 | S31: | -0.4072 | S32: | 0.1423 | S33: | | 0.1015 |
| REMARK | 3 | BULK SOLVENT MODELLING. | | | | | | | |
| REMARK | 3 | METHOD USED: | BABINET MODEL WITH MASK | | | | | | |
| REMARK | 3 | PARAMETERS FOR MASK CALCULATION | | | | | | | |
| REMARK | 3 | VDW PROBE RADIUS: | 1.20 | | | | | | |
| REMARK | 3 | ION PROBE RADIUS: | 0.80 | | | | | | |
| REMARK | 3 | SHRINKAGE RADIUS: | 0.80 | | | | | | |
| REMARK | 3 | | | | | | | | |
| REMARK | 3 | OTHER REFINEMENT REMARKS: | | | | | | | |
| REMARK | 3 | HYDROGENS HAVE BEEN ADDED IN THE RIDING POSITIONS | | | | | | | |
| REMARK | 42 | | | | | | | | |
| REMARK | 42 | MOLPROBITY STRUCTURE VALIDATION | | | | | | | |
| REMARK | 42 | PROGRAMS: | MOLPROBITY (KING, REDUCE, AND PROBE) | | | | | | |
| REMARK | 42 | AUTHORS: | I. W. DAVIS, J. M. WORD | | | | | | |
| REMARK | 42 | URL: | HTTP://KINEMAGE.BIOCHEM.DUKE.EDU/MOL PROBITY/ | | | | | | |
| REMARK | 42 | AUTHORS: | J. S. RICHARDSON, W. B. ARENDALL, D. C. RICHARDSON | | | | | | |
| REMARK | 42 | REFERENCE: | NEW TOOLS AND DATA FOR IMPROVING | | | | | | |
| REMARK | 42 | | STRUCTURES, USING ALL-ATOM CONTACTS | | | | | | |
| REMARK | 42 | | METHODS IN ENZYMOLOGY. 2003;374:385-412. | | | | | | |
| REMARK | 42 | | | | | | | | |
| REMARK | 42 | MOL PROBITY OUTPUT SCORES: | | | | | | | |
| REMARK | 42 | ALL-ATOM CLASHSCORE: | 9.87 | (12.18 B < 40) | | | | | |
| REMARK | 42 | BAD ROTAMERS: | 0.0% | 0/107 | (TARGET 0-1%) | | | | |
| REMARK | 42 | RAMACHANDRAN OUTLIERS: | 0.0% | 0/126 | (TARGET 0.2%) | | | | |
| REMARK | 42 | RAMACHANDRAN FAVORED: | 96.8% | 122/126 | (TARGET 98.0%) | | | | |

TABLE 2-continued

| | | | | | | | | | | | |
|---|---|---|---|---|---|---|---|---|---|---|---|
| REMARK | 300 | BIOMOLECULE: 1 | | | | | | | | | |
| REMARK | 300 | THIS ENTRY CONTAINS THE CRYSTALLOGRAPHIC ASYMMETRIC UNIT | | | | | | | | | |
| REMARK | 300 | WHICH CONSISTS OF 2 CHAIN(S). SEE REMARK 350 FOR | | | | | | | | | |
| REMARK | 300 | INFORMATION ON GENERATING THE BIOLOGICAL MOLECULE(S). | | | | | | | | | |
| REMARK | 350 | | | | | | | | | | |
| REMARK | 350 | GENERATING THE BIOMOLECULE | | | | | | | | | |
| REMARK | 350 | COORDINATES FOR A COMPLETE MULTIMER REPRESENTING THE KNOWN | | | | | | | | | |
| REMARK | 350 | BIOLOGICALLY SIGNIFICANT OLIGOMERIZATION STATE OF THE | | | | | | | | | |
| REMARK | 350 | MOLECULE CAN BE GENERATED BY APPLYING BIOMT TRANSFORMATIONS | | | | | | | | | |
| REMARK | 350 | GIVEN BELOW. BOTH NON-CRYSTALLOGRAPHIC AND | | | | | | | | | |
| REMARK | 350 | CRYSTALLOGRAPHIC OPERATIONS ARE GIVEN. | | | | | | | | | |
| REMARK | 350 | | | | | | | | | | |
| REMARK | 350 | APPLY THE FOLLOWING TO CHAINS: A, B | | | | | | | | | |
| REMARK | 350 | BIOMT1 | | | 1 | 1.000000 | 0.000000 | 0.000000 | | 0.000000 | |
| REMARK | 350 | BIOMT2 | | | 1 | 0.000000 | 1.000000 | 0.000000 | | 0.000000 | |
| REMARK | 350 | BIOMT3 | | | 1 | 0.000000 | 0.000000 | 1.000000 | | 0.000000 | |
| CISPEP | 1 | PHE A | | | 49 | PRO A | | 50 | | | |
| CISPEP | 2 | PHE B | | | 49 | PRO B | | 50 | | | |
| CRYST1 | 46.806 | | 49.621 | | 59.006 | 90.00 | 90.00 | 90.00 | | | |
| SCALE1 | | | 0.021365 | | | 0.000000 | 0.000000 | | 0.000000 | | |
| SCALE2 | | | 0.000000 | | | 0.020153 | 0.000000 | | -0.000000 | | |
| SCALE3 | | | 0.000000 | | | 0.000000 | 0.016947 | | 1.000000 | | |
| ATOM | 1 | N | LYS | A | 1 | -6.743 | 53.624 | 8.839 | 1.00 | 47.95 | N |
| ATOM | 2 | CA | LYS | A | 1 | -7.380 | 52.907 | 9.978 | 1.00 | 47.81 | C |
| ATOM | 9 | C | LYS | A | 1 | -6.621 | 51.647 | 10.377 | 1.00 | 46.88 | C |
| ATOM | 10 | O | LYS | A | 1 | -6.488 | 51.348 | 11.564 | 1.00 | 47.70 | O |
| ATOM | 14 | N | ALA | A | 12 | -6.126 | 50.919 | 9.380 | 1.00 | 45.50 | N |
| ATOM | 15 | CA | ALA | A | 12 | -5.502 | 49.618 | 9.601 | 1.00 | 43.72 | C |
| ATOM | 17 | CB | ALA | A | 12 | -5.569 | 48.792 | 8.331 | 1.00 | 44.48 | C |
| ATOM | 21 | C | ALA | A | 12 | -4.056 | 49.724 | 10.079 | 1.00 | 41.89 | C |
| ATOM | 22 | O | ALA | A | 12 | -3.251 | 50.498 | 9.541 | 1.00 | 40.93 | O |
| ATOM | 24 | N | MET | A | 13 | -3.727 | 48.912 | 11.078 | 1.00 | 40.60 | N |
| ATOM | 25 | CA | MET | A | 13 | -2.350 | 48.780 | 11.500 | 1.00 | 40.06 | C |
| ATOM | 27 | CB | MET | A | 13 | -2.217 | 47.946 | 12.776 | 1.00 | 40.70 | C |
| ATOM | 30 | CG | MET | A | 13 | -2.811 | 48.576 | 14.003 | 1.00 | 41.27 | C |
| ATOM | 33 | SD | MET | A | 13 | -2.193 | 47.776 | 15.493 | 1.00 | 41.27 | S |
| ATOM | 34 | CE | MET | A | 13 | -2.528 | 46.057 | 15.196 | 1.00 | 39.90 | C |
| ATOM | 38 | C | MET | A | 13 | -1.531 | 48.124 | 10.396 | 1.00 | 39.17 | C |
| ATOM | 39 | O | MET | A | 13 | -2.027 | 47.300 | 9.648 | 1.00 | 39.72 | O |
| ATOM | 41 | N | ILE | A | 14 | -0.270 | 48.519 | 10.329 | 1.00 | 35.55 | N |
| ATOM | 42 | CA | ILE | A | 14 | 0.742 | 47.939 | 9.458 | 1.00 | 37.08 | C |
| ATOM | 44 | CB | ILE | A | 14 | 1.786 | 49.027 | 9.124 | 1.00 | 36.72 | C |
| ATOM | 46 | CG1 | ILE | A | 14 | 1.160 | 50.075 | 8.188 | 1.00 | 36.76 | C |
| ATOM | 49 | CD1 | ILE | A | 14 | 2.060 | 51.306 | 8.027 | 1.00 | 38.74 | C |
| ATOM | 53 | CG2 | ILE | A | 14 | 3.093 | 48.487 | 8.544 | 1.00 | 40.88 | C |
| ATOM | 57 | C | ILE | A | 14 | 1.393 | 46.715 | 10.114 | 1.00 | 36.25 | C |
| ATOM | 58 | O | ILE | A | 14 | 1.469 | 45.647 | 9.501 | 1.00 | 35.95 | O |
| ATOM | 60 | N | ASN | A | 15 | 1.846 | 46.866 | 11.355 | 1.00 | 35.24 | N |
| ATOM | 61 | CA | ASN | A | 15 | 2.407 | 45.758 | 12.131 | 1.00 | 35.18 | C |
| ATOM | 63 | CB | ASN | A | 15 | 3.443 | 46.278 | 13.119 | 1.00 | 35.28 | C |
| ATOM | 66 | CG | ASN | A | 15 | 4.031 | 45.180 | 14.010 | 1.00 | 34.36 | C |

TABLE 2-continued

| ATOM | 67 | OD1 | ASN | A | 15 | 4.172 | 44.032 | 13.592 | 1.00 | 32.38 | O |
|---|---|---|---|---|---|---|---|---|---|---|---|
| ATOM | 68 | ND2 | ASN | A | 15 | 4.408 | 45.545 | 15.230 | 1.00 | 34.79 | N |
| ATOM | 71 | C | ASN | A | 15 | 1.302 | 45.052 | 12.875 | 1.00 | 34.93 | C |
| ATOM | 72 | O | ASN | A | 15 | 0.628 | 45.656 | 13.698 | 1.00 | 34.35 | O |
| ATOM | 74 | N | LEU | A | 16 | 1.112 | 43.771 | 12.571 | 1.00 | 36.05 | N |
| ATOM | 75 | CA | LEU | A | 16 | 0.117 | 42.969 | 13.249 | 1.00 | 36.93 | C |
| ATOM | 77 | CB | LEU | A | 16 | -0.390 | 41.877 | 12.317 | 1.00 | 36.97 | C |
| ATOM | 80 | CG | LEU | A | 16 | -0.808 | 42.301 | 10.897 | 1.00 | 41.44 | C |
| ATOM | 82 | CD1 | LEU | A | 16 | -1.323 | 41.128 | 10.091 | 1.00 | 43.39 | C |
| ATOM | 86 | CD2 | LEU | A | 16 | -1.857 | 43.394 | 10.964 | 1.00 | 45.54 | C |
| ATOM | 90 | C | LEU | A | 16 | 0.625 | 42.335 | 14.554 | 1.00 | 35.25 | C |
| ATOM | 91 | O | LEU | A | 16 | -0.094 | 42.348 | 15.528 | 1.00 | 35.83 | O |
| ATOM | 93 | N | HIS | A | 17 | 1.851 | 41.805 | 14.568 | 1.00 | 36.20 | N |
| ATOM | 94 | CA | HIS | A | 17 | 2.296 | 40.841 | 15.613 | 1.00 | 36.64 | C |
| ATOM | 96 | CB | HIS | A | 17 | 2.374 | 39.424 | 15.028 | 1.00 | 36.49 | C |
| ATOM | 99 | CG | HIS | A | 17 | 1.099 | 38.973 | 14.423 | 1.00 | 31.12 | C |
| ATOM | 100 | ND1 | HIS | A | 17 | 1.015 | 38.417 | 13.168 | 1.00 | 32.44 | N |
| ATOM | 102 | CE1 | HIS | A | 17 | -0.248 | 38.123 | 12.917 | 1.00 | 38.49 | C |
| ATOM | 104 | NE2 | HIS | A | 17 | -0.978 | 38.486 | 13.952 | 1.00 | 36.77 | N |
| ATOM | 106 | CD2 | HIS | A | 17 | -0.159 | 39.009 | 14.913 | 1.00 | 36.54 | C |
| ATOM | 108 | C | HIS | A | 17 | 3.644 | 41.084 | 16.250 | 1.00 | 35.17 | C |
| ATOM | 109 | O | HIS | A | 17 | 3.978 | 40.403 | 17.216 | 1.00 | 34.84 | O |
| ATOM | 111 | N | ILE | A | 18 | 4.439 | 41.996 | 15.723 | 1.00 | 35.43 | N |
| ATOM | 112 | CA | ILE | A | 18 | 5.829 | 42.086 | 16.162 | 1.00 | 35.81 | C |
| ATOM | 114 | CB | ILE | A | 18 | 6.743 | 42.559 | 15.051 | 1.00 | 36.21 | C |
| ATOM | 116 | CG1 | ILE | A | 18 | 6.760 | 41.510 | 13.925 | 1.00 | 37.53 | C |
| ATOM | 119 | CD1 | ILE | A | 18 | 7.326 | 42.020 | 12.672 | 1.00 | 36.04 | C |
| ATOM | 123 | CG2 | ILE | A | 18 | 8.159 | 42.807 | 15.601 | 1.00 | 36.56 | C |
| ATOM | 127 | C | ILE | A | 18 | 5.942 | 42.974 | 17.409 | 1.00 | 34.37 | C |
| ATOM | 128 | O | ILE | A | 18 | 5.404 | 44.063 | 17.421 | 1.00 | 35.54 | O |
| ATOM | 130 | N | GLN | A | 19 | 6.548 | 42.411 | 18.455 | 1.00 | 35.41 | N |
| ATOM | 131 | CA | AGLN | A | 19 | 6.844 | 43.097 | 19.721 | 0.50 | 34.96 | C |
| ATOM | 132 | CA | BGLN | A | 19 | 6.855 | 43.108 | 19.698 | 0.50 | 34.80 | C |
| ATOM | 135 | CB | AGLN | A | 19 | 8.264 | 43.697 | 19.718 | 0.50 | 35.61 | C |
| ATOM | 136 | CB | BGLN | A | 19 | 8.249 | 43.722 | 19.568 | 0.50 | 35.23 | C |
| ATOM | 141 | CG | AGLN | A | 19 | 8.871 | 43.751 | 21.130 | 0.50 | 37.48 | C |
| ATOM | 142 | CG | BGLN | A | 19 | 9.347 | 42.659 | 19.450 | 0.50 | 36.70 | C |
| ATOM | 147 | CD | AGLN | A | 19 | 10.104 | 44.659 | 21.284 | 0.50 | 37.00 | C |
| ATOM | 148 | CD | BGLN | A | 19 | 10.569 | 43.123 | 18.696 | 0.50 | 36.74 | C |
| ATOM | 149 | OE1 | AGLN | A | 19 | 10.600 | 45.255 | 20.330 | 0.50 | 39.57 | O |
| ATOM | 150 | OE1 | BGLN | A | 19 | 10.822 | 44.322 | 18.549 | 0.50 | 47.19 | O |
| ATOM | 151 | NE2 | AGLN | A | 19 | 10.583 | 44.769 | 22.514 | 0.50 | 41.68 | N |
| ATOM | 152 | NE2 | BGLN | A | 19 | 11.346 | 42.162 | 18.200 | 0.50 | 44.47 | N |
| ATOM | 157 | C | GLN | A | 19 | 5.813 | 44.150 | 20.109 | 1.00 | 34.89 | C |
| ATOM | 158 | O | GLN | A | 19 | 6.118 | 45.324 | 20.291 | 1.00 | 33.05 | O |
| ATOM | 160 | N | LYS | A | 20 | 4.583 | 43.707 | 20.297 | 1.00 | 33.55 | N |
| ATOM | 161 | CA | LYS | A | 20 | 3.482 | 44.610 | 20.584 | 1.00 | 34.69 | C |
| ATOM | 163 | CB | LYS | A | 20 | 2.139 | 43.937 | 20.279 | 1.00 | 36.04 | C |
| ATOM | 166 | CG | LYS | A | 20 | 1.817 | 43.857 | 18.773 | 1.00 | 33.88 | C |
| ATOM | 169 | CD | LYS | A | 20 | 1.621 | 45.239 | 18.183 | 1.00 | 32.00 | C |
| ATOM | 172 | CE | LYS | A | 20 | 1.237 | 45.217 | 16.739 | 1.00 | 32.96 | C |
| ATOM | 175 | NZ | LYS | A | 20 | 1.115 | 46.616 | 16.171 | 1.00 | 33.71 | N |
| ATOM | 179 | C | LYS | A | 20 | 3.524 | 45.235 | 22.000 | 1.00 | 34.80 | C |

TABLE 2-continued

| ATOM | 180 | O | LYS | A | 2.797 | 46.193 | 22.283 | 1.00 | 35.65 | O |
|------|-----|-----|------|---|--------|--------|--------|------|-------|---|
| ATOM | 182 | N | ASP | A | 4.412 | 44.715 | 22.851 | 1.00 | 34.39 | N |
| ATOM | 183 | CA | AASP | A | 4.699 | 45.300 | 24.168 | 0.50 | 34.07 | C |
| ATOM | 184 | CA | BASP | A | 4.694 | 45.304 | 24.170 | 0.50 | 34.57 | C |
| ATOM | 187 | CB | AASP | A | 5.280 | 44.243 | 25.119 | 0.50 | 33.67 | C |
| ATOM | 188 | CB | BASP | A | 5.286 | 44.249 | 25.111 | 0.50 | 34.71 | C |
| ATOM | 193 | CG | AASP | A | 6.507 | 44.554 | 25.353 | 0.50 | 32.48 | C |
| ATOM | 194 | CG | BASP | A | 4.340 | 43.533 | 24.554 | 0.50 | 37.38 | C |
| ATOM | 195 | OD1 | AASP | A | 6.624 | 43.082 | 25.353 | 0.50 | 34.02 | O |
| ATOM | 196 | OD1 | BASP | A | 3.103 | 43.337 | 23.317 | 0.50 | 43.21 | O |
| ATOM | 197 | OD2 | AASP | A | 7.348 | 43.266 | 25.239 | 0.50 | 38.60 | O |
| ATOM | 198 | OD2 | BASP | A | 4.833 | 43.127 | 25.374 | 0.50 | 41.96 | O |
| ATOM | 199 | C | ASP | A | 5.629 | 41.979 | 25.674 | 1.00 | 34.26 | C |
| ATOM | 200 | O | ASP | A | 5.835 | 46.513 | 24.096 | 1.00 | 33.26 | O |
| ATOM | 202 | N | ASN | A | 6.192 | 47.198 | 25.084 | 1.00 | 32.72 | N |
| ATOM | 203 | CA | ASN | A | 6.980 | 46.758 | 22.918 | 1.00 | 34.68 | C |
| ATOM | 205 | CB | ASN | A | 8.149 | 47.947 | 22.641 | 1.00 | 34.90 | C |
| ATOM | 208 | CG | ASN | A | 9.095 | 47.536 | 21.743 | 1.00 | 33.24 | C |
| ATOM | 209 | OD1 | ASN | A | 8.829 | 48.656 | 21.432 | 1.00 | 32.55 | O |
| ATOM | 210 | ND2 | ASN | A | 10.239 | 49.825 | 21.697 | 1.00 | 35.24 | N |
| ATOM | 213 | C | ASN | A | 6.111 | 48.294 | 20.866 | 1.00 | 34.45 | C |
| ATOM | 214 | O | ASN | A | 5.653 | 48.992 | 21.947 | 1.00 | 34.89 | O |
| ATOM | 216 | N | PRO | A | 5.870 | 48.757 | 20.833 | 1.00 | 32.88 | N |
| ATOM | 217 | CA | PRO | A | 4.967 | 50.154 | 22.603 | 1.00 | 34.20 | C |
| ATOM | 219 | CB | PRO | A | 4.772 | 51.141 | 22.034 | 1.00 | 33.99 | C |
| ATOM | 222 | CG | PRO | A | 5.993 | 52.144 | 23.175 | 1.00 | 34.46 | C |
| ATOM | 225 | CD | PRO | A | 6.416 | 52.061 | 23.949 | 1.00 | 32.78 | C |
| ATOM | 228 | C | PRO | A | 5.443 | 50.627 | 23.892 | 1.00 | 33.65 | C |
| ATOM | 229 | O | PRO | A | 4.638 | 51.827 | 20.748 | 1.00 | 35.26 | O |
| ATOM | 230 | N | LYS | A | 6.724 | 52.435 | 20.074 | 1.00 | 35.11 | N |
| ATOM | 231 | CA | LYS | A | 7.236 | 51.751 | 20.419 | 1.00 | 35.75 | C |
| ATOM | 233 | CB | LYS | A | 7.455 | 52.240 | 19.153 | 1.00 | 35.95 | C |
| ATOM | 236 | CG | LYS | A | 8.036 | 53.745 | 19.165 | 1.00 | 38.03 | C |
| ATOM | 239 | CD | LYS | A | 7.974 | 54.268 | 17.839 | 1.00 | 40.90 | C |
| ATOM | 242 | CE | LYS | A | 9.123 | 55.783 | 17.739 | 1.00 | 48.61 | C |
| ATOM | 245 | NZ | LYS | A | 9.122 | 56.495 | 18.400 | 1.00 | 50.05 | N |
| ATOM | 249 | C | LYS | A | 8.539 | 57.921 | 17.923 | 1.00 | 33.36 | C |
| ATOM | 250 | O | LYS | A | 9.580 | 51.527 | 18.824 | 1.00 | 34.14 | O |
| ATOM | 252 | N | ILE | A | 8.468 | 51.766 | 19.474 | 1.00 | 34.61 | N |
| ATOM | 253 | CA | ILE | A | 9.572 | 50.681 | 17.804 | 1.00 | 34.51 | C |
| ATOM | 255 | CB | ILE | A | 9.108 | 49.850 | 17.402 | 1.00 | 33.90 | C |
| ATOM | 257 | CG1 | ILE | A | 8.230 | 48.532 | 16.761 | 1.00 | 35.23 | C |
| ATOM | 260 | CD1 | ILE | A | 7.483 | 47.738 | 17.740 | 1.00 | 34.85 | C |
| ATOM | 264 | CG2 | ILE | A | 10.360 | 46.631 | 17.097 | 1.00 | 33.13 | C |
| ATOM | 268 | C | ILE | A | 10.516 | 47.704 | 16.298 | 1.00 | 34.50 | C |
| ATOM | 269 | O | ILE | A | 10.183 | 50.615 | 16.479 | 1.00 | 34.69 | O |
| ATOM | 271 | N | VAL | A | 11.714 | 50.906 | 15.350 | 1.00 | 32.53 | N |
| ATOM | 272 | CA | VAL | A | 12.804 | 50.882 | 17.002 | 1.00 | 34.27 | C |
| ATOM | 274 | CB | VAL | A | 13.104 | 51.589 | 16.324 | 1.00 | 35.35 | C |
| ATOM | 276 | CG1 | VAL | A | 14.283 | 52.965 | 16.994 | 1.00 | 33.93 | C |
| ATOM | 280 | CG2 | VAL | A | 11.855 | 53.705 | 16.293 | 1.00 | 36.10 | C |
| ATOM | 284 | C | VAL | A | 14.035 | 53.855 | 17.076 | 1.00 | 35.41 | C |
| ATOM | 285 | O | VAL | A | 14.319 | 50.093 | 17.467 | 1.00 | 35.61 | O |

TABLE 2-continued

| ATOM | 287 | N | HIS | A | 27 | 14.791 | 50.641 | 15.336 | 1.00 | 34.88 | N |
|------|-----|-----|-----|---|----|--------|--------|--------|------|-------|---|
| ATOM | 288 | CA | HIS | A | 27 | 16.106 | 49.985 | 15.359 | 1.00 | 34.59 | C |
| ATOM | 290 | CB | HIS | A | 27 | 16.121 | 48.757 | 14.452 | 1.00 | 34.48 | C |
| ATOM | 293 | CG | HIS | A | 27 | 15.303 | 47.616 | 14.980 | 1.00 | 32.57 | C |
| ATOM | 294 | ND1 | HIS | A | 27 | 13.944 | 47.503 | 14.772 | 1.00 | 31.98 | N |
| ATOM | 296 | CE1 | HIS | A | 27 | 13.492 | 46.415 | 15.366 | 1.00 | 32.36 | C |
| ATOM | 298 | NE2 | HIS | A | 27 | 14.510 | 45.814 | 15.949 | 1.00 | 36.20 | N |
| ATOM | 300 | CD2 | HIS | A | 27 | 15.645 | 46.554 | 15.736 | 1.00 | 34.72 | C |
| ATOM | 302 | C | HIS | A | 27 | 17.191 | 50.939 | 14.948 | 1.00 | 35.90 | C |
| ATOM | 303 | O | HIS | A | 27 | 16.989 | 51.807 | 14.092 | 1.00 | 37.82 | O |
| ATOM | 305 | N | ALA | A | 28 | 18.340 | 50.787 | 15.595 | 1.00 | 34.12 | N |
| ATOM | 306 | CA | ALA | A | 28 | 19.497 | 51.603 | 15.309 | 1.00 | 34.40 | C |
| ATOM | 308 | CB | ALA | A | 28 | 19.668 | 52.693 | 16.354 | 1.00 | 35.23 | C |
| ATOM | 312 | C | ALA | A | 28 | 20.754 | 50.742 | 15.227 | 1.00 | 34.73 | C |
| ATOM | 313 | O | ALA | A | 28 | 21.087 | 50.004 | 16.167 | 1.00 | 37.66 | O |
| ATOM | 315 | N | PHE | A | 29 | 21.429 | 50.832 | 14.085 | 1.00 | 35.13 | N |
| ATOM | 316 | CA | PHE | A | 29 | 22.716 | 50.162 | 13.857 | 1.00 | 35.34 | C |
| ATOM | 318 | CB | PHE | A | 29 | 22.571 | 49.085 | 12.785 | 1.00 | 35.54 | C |
| ATOM | 321 | CG | PHE | A | 29 | 21.503 | 48.065 | 13.086 | 1.00 | 34.11 | C |
| ATOM | 322 | CD1 | PHE | A | 29 | 21.777 | 46.963 | 13.886 | 1.00 | 40.35 | C |
| ATOM | 324 | CE1 | PHE | A | 29 | 20.790 | 46.027 | 14.165 | 1.00 | 35.67 | C |
| ATOM | 326 | CZ | PHE | A | 29 | 19.520 | 46.182 | 13.643 | 1.00 | 35.53 | C |
| ATOM | 328 | CE2 | PHE | A | 29 | 19.234 | 47.259 | 12.853 | 1.00 | 36.90 | C |
| ATOM | 330 | CD2 | PHE | A | 29 | 20.221 | 48.204 | 12.574 | 1.00 | 36.72 | C |
| ATOM | 332 | C | PHE | A | 29 | 23.845 | 51.110 | 13.461 | 1.00 | 36.23 | C |
| ATOM | 333 | O | PHE | A | 29 | 23.627 | 52.088 | 12.742 | 1.00 | 33.04 | O |
| ATOM | 335 | N | ASP | A | 30 | 25.046 | 50.784 | 13.940 | 1.00 | 37.95 | N |
| ATOM | 336 | CA | ASP | A | 30 | 26.300 | 51.413 | 13.510 | 1.00 | 37.56 | C |
| ATOM | 338 | CB | ASP | A | 30 | 27.377 | 51.334 | 14.603 | 1.00 | 37.01 | C |
| ATOM | 341 | CG | ASP | A | 30 | 27.044 | 52.188 | 15.825 | 1.00 | 39.49 | C |
| ATOM | 342 | OD1 | ASP | A | 30 | 26.255 | 53.148 | 15.707 | 1.00 | 42.71 | O |
| ATOM | 343 | OD2 | ASP | A | 30 | 27.585 | 51.903 | 16.915 | 1.00 | 47.86 | O |
| ATOM | 344 | C | ASP | A | 30 | 26.786 | 50.722 | 12.238 | 1.00 | 38.40 | C |
| ATOM | 345 | O | ASP | A | 30 | 26.773 | 49.499 | 12.155 | 1.00 | 37.73 | O |
| ATOM | 347 | N | MET | A | 31 | 27.177 | 51.515 | 11.242 | 1.00 | 41.19 | N |
| ATOM | 348 | CA | MET | A | 31 | 27.684 | 51.006 | 9.957 | 1.00 | 43.91 | C |
| ATOM | 350 | CB | MET | A | 31 | 28.162 | 52.173 | 9.082 | 1.00 | 44.28 | C |
| ATOM | 353 | CG | MET | A | 31 | 27.055 | 53.000 | 8.465 | 1.00 | 45.49 | C |
| ATOM | 356 | SD | MET | A | 31 | 27.755 | 54.459 | 7.669 | 1.00 | 48.74 | S |
| ATOM | 357 | CE | MET | A | 31 | 26.391 | 55.609 | 7.877 | 1.00 | 47.83 | C |
| ATOM | 361 | C | MET | A | 31 | 28.856 | 50.039 | 10.101 | 1.00 | 43.70 | C |
| ATOM | 362 | O | MET | A | 31 | 29.032 | 49.127 | 9.299 | 1.00 | 43.39 | O |
| ATOM | 364 | N | GLU | A | 32 | 29.660 | 50.248 | 11.125 | 1.00 | 45.02 | N |
| ATOM | 365 | CA | GLU | A | 32 | 30.881 | 49.482 | 11.300 | 1.00 | 46.48 | C |
| ATOM | 367 | CB | GLU | A | 32 | 31.744 | 50.138 | 12.381 | 1.00 | 46.42 | C |
| ATOM | 370 | CG | GLU | A | 32 | 32.302 | 51.531 | 11.990 | 1.00 | 49.69 | C |
| ATOM | 373 | CD | GLU | A | 32 | 31.229 | 52.606 | 11.796 | 1.00 | 49.82 | C |
| ATOM | 374 | OE1 | GLU | A | 32 | 30.124 | 52.463 | 12.361 | 1.00 | 47.09 | O |
| ATOM | 375 | OE2 | GLU | A | 32 | 31.496 | 53.596 | 11.078 | 1.00 | 52.35 | O |
| ATOM | 376 | C | GLU | A | 32 | 30.591 | 48.009 | 11.635 | 1.00 | 46.94 | C |
| ATOM | 377 | O | GLU | A | 32 | 31.370 | 47.121 | 11.288 | 1.00 | 47.15 | O |
| ATOM | 379 | N | ASP | A | 33 | 29.460 | 47.754 | 12.281 | 1.00 | 47.07 | N |
| ATOM | 380 | CA | ASP | A | 33 | 29.065 | 46.392 | 12.649 | 1.00 | 47.78 | C |

TABLE 2-continued

| | | | | | | | | | | | |
|---|---|---|---|---|---|---|---|---|---|---|---|
| ATOM | 382 | CB | ASP | A | 33 | 28.209 | 46.420 | 13.923 | 1.00 | 48.50 | C |
| ATOM | 385 | CG | ASP | A | 33 | 28.889 | 47.134 | 15.084 | 1.00 | 49.82 | C |
| ATOM | 386 | OD1 | ASP | A | 33 | 30.141 | 47.112 | 15.171 | 1.00 | 50.21 | O |
| ATOM | 387 | OD2 | ASP | A | 33 | 28.149 | 47.715 | 15.914 | 1.00 | 54.83 | O |
| ATOM | 388 | C | ASP | A | 33 | 28.265 | 45.670 | 11.562 | 1.00 | 47.66 | C |
| ATOM | 389 | O | ASP | A | 33 | 27.890 | 44.509 | 11.742 | 1.00 | 48.56 | O |
| ATOM | 391 | N | ALEU | A | 34 | 27.934 | 46.397 | 10.497 | 0.50 | 47.20 | N |
| ATOM | 392 | N | BLEU | A | 34 | 28.075 | 46.299 | 10.400 | 0.50 | 47.37 | N |
| ATOM | 393 | CA | ALEU | A | 34 | 27.291 | 45.810 | 9.337 | 0.50 | 46.51 | C |
| ATOM | 394 | CA | BLEU | A | 34 | 27.014 | 45.886 | 9.463 | 0.50 | 46.74 | C |
| ATOM | 397 | CB | ALEU | A | 34 | 26.557 | 46.870 | 8.503 | 0.50 | 46.22 | C |
| ATOM | 398 | CB | BLEU | A | 34 | 26.492 | 47.111 | 8.697 | 0.50 | 46.33 | C |
| ATOM | 403 | CG | ALEU | A | 34 | 25.092 | 47.138 | 8.849 | 0.50 | 47.15 | C |
| ATOM | 404 | CG | BLEU | A | 34 | 24.976 | 47.272 | 8.674 | 0.50 | 47.09 | C |
| ATOM | 407 | CD1 | ALEU | A | 34 | 24.830 | 47.137 | 10.347 | 0.50 | 48.21 | C |
| ATOM | 408 | CD1 | BLEU | A | 34 | 24.459 | 47.664 | 10.052 | 0.50 | 46.24 | C |
| ATOM | 415 | CD2 | ALEU | A | 34 | 24.649 | 48.455 | 8.222 | 0.50 | 46.33 | C |
| ATOM | 416 | CD2 | BLEU | A | 34 | 24.583 | 48.307 | 7.642 | 0.50 | 46.32 | C |
| ATOM | 423 | C | ALEU | A | 34 | 28.361 | 45.133 | 8.511 | 0.50 | 46.18 | C |
| ATOM | 424 | C | BLEU | A | 34 | 27.357 | 44.768 | 8.458 | 0.50 | 46.82 | C |
| ATOM | 425 | O | ALEU | A | 34 | 29.452 | 45.671 | 8.308 | 0.50 | 45.87 | O |
| ATOM | 426 | O | BLEU | A | 34 | 26.447 | 44.136 | 7.917 | 0.50 | 47.43 | O |
| ATOM | 429 | N | AGLY | A | 35 | 28.050 | 43.931 | 8.058 | 0.50 | 45.89 | N |
| ATOM | 430 | N | BGLY | A | 35 | 28.640 | 44.524 | 8.196 | 0.50 | 46.36 | N |
| ATOM | 431 | CA | AGLY | A | 35 | 28.920 | 43.256 | 7.138 | 0.50 | 46.13 | C |
| ATOM | 432 | CA | BGLY | A | 35 | 29.028 | 43.531 | 7.184 | 0.50 | 46.43 | C |
| ATOM | 437 | C | AGLY | A | 35 | 28.873 | 43.983 | 5.815 | 0.50 | 46.11 | C |
| ATOM | 438 | C | BGLY | A | 35 | 28.695 | 44.003 | 5.777 | 0.50 | 46.20 | C |
| ATOM | 439 | O | AGLY | A | 35 | 28.704 | 45.201 | 5.759 | 0.50 | 47.01 | O |
| ATOM | 440 | O | BGLY | A | 35 | 28.086 | 45.064 | 5.616 | 0.50 | 46.67 | O |
| ATOM | 443 | N | ASP | A | 36 | 29.048 | 43.216 | 4.754 | 1.00 | 45.71 | N |
| ATOM | 444 | CA | ASP | A | 36 | 28.959 | 43.704 | 3.371 | 1.00 | 44.61 | C |
| ATOM | 446 | CB | ASP | A | 36 | 29.458 | 42.632 | 2.400 | 1.00 | 44.82 | C |
| ATOM | 449 | CG | ASP | A | 36 | 30.940 | 42.355 | 2.532 | 1.00 | 43.61 | C |
| ATOM | 450 | OD1 | ASP | A | 36 | 31.634 | 43.053 | 3.305 | 1.00 | 44.10 | O |
| ATOM | 451 | OD2 | ASP | A | 36 | 31.408 | 41.419 | 1.857 | 1.00 | 45.65 | O |
| ATOM | 452 | C | ASP | A | 36 | 27.561 | 44.134 | 2.938 | 1.00 | 43.22 | C |
| ATOM | 453 | O | ASP | A | 36 | 27.421 | 45.045 | 2.134 | 1.00 | 42.87 | O |
| ATOM | 455 | N | LYS | A | 37 | 26.534 | 43.470 | 3.462 | 1.00 | 42.40 | N |
| ATOM | 456 | CA | LYS | A | 37 | 25.155 | 43.745 | 3.080 | 1.00 | 41.41 | C |
| ATOM | 458 | CB | LYS | A | 37 | 24.790 | 42.933 | 1.839 | 1.00 | 40.60 | C |
| ATOM | 461 | CG | LYS | A | 37 | 23.368 | 43.091 | 1.345 | 1.00 | 42.83 | C |
| ATOM | 464 | CD | LYS | A | 37 | 23.206 | 42.367 | 0.018 | 1.00 | 43.55 | C |
| ATOM | 467 | CE | LYS | A | 37 | 21.774 | 42.427 | -0.482 | 1.00 | 46.47 | C |
| ATOM | 470 | NZ | LYS | A | 37 | 21.649 | 41.924 | -1.875 | 1.00 | 48.15 | N |
| ATOM | 474 | C | LYS | A | 37 | 24.214 | 43.400 | 4.223 | 1.00 | 40.47 | C |
| ATOM | 475 | O | LYS | A | 37 | 24.366 | 42.359 | 4.862 | 1.00 | 41.54 | O |
| ATOM | 477 | N | ALA | A | 38 | 23.281 | 44.310 | 4.500 | 1.00 | 42.40 | N |
| ATOM | 478 | CA | ALA | A | 38 | 22.152 | 44.067 | 5.408 | 1.00 | 38.26 | C |
| ATOM | 480 | CB | ALA | A | 38 | 22.291 | 44.909 | 6.652 | 1.00 | 37.33 | C |
| ATOM | 484 | C | ALA | A | 38 | 20.856 | 44.389 | 4.675 | 1.00 | 38.29 | C |
| ATOM | 485 | O | ALA | A | 38 | 20.761 | 45.378 | 3.951 | 1.00 | 36.17 | O |
| ATOM | 487 | N | VAL | A | 39 | 19.846 | 43.552 | 4.886 | 1.00 | 35.30 | N |

TABLE 2-continued

| | | | | | | | | | |
|---|---|---|---|---|---|---|---|---|---|
| ATOM | 488 | CA | VAL | A | 39 | 18.608 | 43.664 | 4.175 | 1.00 | 35.23 | C |
| ATOM | 490 | CB | VAL | A | 39 | 18.368 | 42.433 | 3.273 | 1.00 | 32.94 | C |
| ATOM | 492 | CG1 | VAL | A | 39 | 17.091 | 42.640 | 2.437 | 1.00 | 33.74 | C |
| ATOM | 496 | CG2 | VAL | A | 39 | 19.514 | 42.246 | 2.366 | 1.00 | 37.59 | C |
| ATOM | 500 | C | VAL | A | 39 | 17.527 | 43.773 | 5.219 | 1.00 | 34.62 | C |
| ATOM | 501 | O | VAL | A | 39 | 17.257 | 42.813 | 5.925 | 1.00 | 36.58 | O |
| ATOM | 503 | N | TYR | A | 40 | 16.879 | 44.942 | 5.290 | 1.00 | 35.87 | N |
| ATOM | 504 | CA | TYR | A | 40 | 15.998 | 45.263 | 6.399 | 1.00 | 35.00 | C |
| ATOM | 506 | CB | TYR | A | 40 | 16.327 | 46.644 | 6.931 | 1.00 | 36.71 | C |
| ATOM | 509 | CG | TYR | A | 40 | 17.700 | 46.744 | 7.547 | 1.00 | 36.48 | C |
| ATOM | 510 | CD1 | TYR | A | 40 | 17.966 | 46.173 | 8.787 | 1.00 | 36.88 | C |
| ATOM | 512 | CE1 | TYR | A | 40 | 19.202 | 46.272 | 9.364 | 1.00 | 39.82 | C |
| ATOM | 514 | CZ | TYR | A | 40 | 20.210 | 46.960 | 8.710 | 1.00 | 37.22 | C |
| ATOM | 515 | OH | TYR | A | 40 | 21.438 | 47.070 | 9.277 | 1.00 | 41.39 | O |
| ATOM | 517 | CE2 | TYR | A | 40 | 19.978 | 47.559 | 7.486 | 1.00 | 35.96 | C |
| ATOM | 519 | CD2 | TYR | A | 40 | 18.728 | 47.445 | 6.910 | 1.00 | 37.96 | C |
| ATOM | 521 | C | TYR | A | 40 | 14.559 | 45.214 | 5.951 | 1.00 | 34.28 | C |
| ATOM | 522 | O | TYR | A | 40 | 14.215 | 45.680 | 4.878 | 1.00 | 36.27 | O |
| ATOM | 524 | N | CYS | A | 41 | 13.713 | 44.661 | 6.799 | 1.00 | 34.83 | N |
| ATOM | 525 | CA | CYS | A | 41 | 12.320 | 44.500 | 6.488 | 1.00 | 34.66 | C |
| ATOM | 527 | CB | CYS | A | 41 | 11.762 | 43.417 | 7.419 | 1.00 | 35.35 | C |
| ATOM | 530 | SG | CYS | A | 41 | 9.984 | 43.192 | 7.286 | 1.00 | 34.48 | S |
| ATOM | 532 | C | CYS | A | 41 | 11.510 | 45.817 | 6.614 | 1.00 | 36.06 | C |
| ATOM | 533 | O | CYS | A | 41 | 11.616 | 46.548 | 7.603 | 1.00 | 35.73 | O |
| ATOM | 535 | N | ARG | A | 42 | 10.687 | 46.127 | 5.620 | 1.00 | 35.46 | N |
| ATOM | 536 | CA | ARG | A | 42 | 9.819 | 47.306 | 5.700 | 1.00 | 35.31 | C |
| ATOM | 538 | CB | ARG | A | 42 | 10.169 | 48.348 | 4.617 | 1.00 | 35.03 | C |
| ATOM | 541 | CG | ARG | A | 42 | 11.574 | 48.871 | 4.728 | 1.00 | 36.55 | C |
| ATOM | 544 | CD | ARG | A | 42 | 11.804 | 50.025 | 3.779 | 1.00 | 34.14 | C |
| ATOM | 547 | NE | ARG | A | 42 | 11.712 | 49.668 | 2.359 | 1.00 | 32.41 | N |
| ATOM | 549 | CZ | ARG | A | 42 | 12.049 | 50.478 | 1.345 | 1.00 | 35.15 | C |
| ATOM | 550 | NH1 | ARG | A | 42 | 12.534 | 51.700 | 1.552 | 1.00 | 35.36 | N |
| ATOM | 553 | NH2 | ARG | A | 42 | 11.942 | 50.053 | 0.087 | 1.00 | 33.30 | N |
| ATOM | 556 | C | ARG | A | 42 | 8.345 | 46.939 | 5.644 | 1.00 | 35.13 | C |
| ATOM | 557 | O | ARG | A | 42 | 7.461 | 47.741 | 5.474 | 1.00 | 36.64 | O |
| ATOM | 559 | N | CYS | A | 43 | 8.070 | 45.652 | 5.778 | 1.00 | 32.18 | N |
| ATOM | 560 | CA | CYS | A | 43 | 6.708 | 45.153 | 5.706 | 1.00 | 34.67 | C |
| ATOM | 562 | CB | CYS | A | 43 | 6.589 | 44.019 | 4.662 | 1.00 | 35.05 | C |
| ATOM | 565 | SG | CYS | A | 43 | 7.402 | 42.411 | 5.071 | 1.00 | 32.36 | S |
| ATOM | 567 | C | CYS | A | 43 | 6.170 | 44.652 | 7.034 | 1.00 | 35.81 | C |
| ATOM | 568 | O | CYS | A | 43 | 4.999 | 44.321 | 7.111 | 1.00 | 34.20 | O |
| ATOM | 570 | N | TRP | A | 44 | 7.003 | 44.505 | 8.056 | 1.00 | 36.58 | N |
| ATOM | 571 | CA | TRP | A | 44 | 6.526 | 43.977 | 9.363 | 1.00 | 35.83 | C |
| ATOM | 573 | CB | TRP | A | 44 | 5.595 | 45.004 | 10.039 | 1.00 | 34.90 | C |
| ATOM | 576 | CG | TRP | A | 44 | 6.257 | 46.312 | 10.148 | 1.00 | 33.83 | C |
| ATOM | 577 | CD1 | TRP | A | 44 | 6.319 | 47.268 | 9.185 | 1.00 | 35.38 | C |
| ATOM | 579 | NE1 | TRP | A | 44 | 7.063 | 48.323 | 9.610 | 1.00 | 34.34 | N |
| ATOM | 581 | CE2 | TRP | A | 44 | 7.460 | 48.095 | 10.891 | 1.00 | 31.37 | C |
| ATOM | 582 | CD2 | TRP | A | 44 | 6.981 | 46.827 | 11.266 | 1.00 | 35.48 | C |
| ATOM | 583 | CE3 | TRP | A | 44 | 7.248 | 46.352 | 12.561 | 1.00 | 34.67 | C |
| ATOM | 585 | CZ3 | TRP | A | 44 | 7.992 | 47.141 | 13.406 | 1.00 | 33.85 | C |
| ATOM | 587 | CH2 | TRP | A | 44 | 8.452 | 48.392 | 13.009 | 1.00 | 35.34 | C |
| ATOM | 589 | CZ2 | TRP | A | 44 | 8.214 | 48.883 | 11.739 | 1.00 | 32.92 | C |

TABLE 2-continued

| ATOM | 591 | C | TRP | A | 44 | 5.909 | 42.573 | 9.305 | 1.00 | 36.50 | C |
|---|---|---|---|---|---|---|---|---|---|---|---|
| ATOM | 592 | O | TRP | A | 44 | 5.057 | 42.238 | 10.101 | 1.00 | 37.50 | O |
| ATOM | 594 | N | ARG | A | 45 | 6.403 | 41.733 | 8.394 | 1.00 | 34.96 | N |
| ATOM | 595 | CA | ARG | A | 45 | 5.963 | 40.348 | 8.301 | 1.00 | 35.12 | C |
| ATOM | 597 | CB | ARG | A | 45 | 5.235 | 40.076 | 6.974 | 1.00 | 36.08 | C |
| ATOM | 600 | CG | ARG | A | 45 | 3.966 | 40.923 | 6.722 | 1.00 | 37.84 | C |
| ATOM | 603 | CD | ARG | A | 45 | 2.841 | 40.629 | 7.684 | 1.00 | 40.45 | C |
| ATOM | 606 | NE | ARG | A | 45 | 1.681 | 41.473 | 7.398 | 1.00 | 37.30 | N |
| ATOM | 608 | CZ | ARG | A | 45 | 1.484 | 42.679 | 7.927 | 1.00 | 38.29 | C |
| ATOM | 609 | NH1 | ARG | A | 45 | 2.316 | 43.156 | 8.835 | 1.00 | 39.81 | N |
| ATOM | 612 | NH2 | ARG | A | 45 | 0.405 | 43.379 | 7.599 | 1.00 | 39.60 | N |
| ATOM | 615 | C | ARG | A | 45 | 7.098 | 39.361 | 8.451 | 1.00 | 35.11 | C |
| ATOM | 616 | O | ARG | A | 45 | 6.841 | 38.155 | 8.529 | 1.00 | 35.05 | O |
| ATOM | 618 | N | SER | A | 46 | 8.342 | 39.829 | 8.497 | 1.00 | 35.48 | N |
| ATOM | 619 | CA | SER | A | 46 | 9.476 | 38.918 | 8.573 | 1.00 | 35.65 | C |
| ATOM | 621 | CB | SER | A | 46 | 10.772 | 39.662 | 8.356 | 1.00 | 35.04 | C |
| ATOM | 624 | OG | SER | A | 46 | 11.878 | 38.769 | 8.446 | 1.00 | 36.05 | O |
| ATOM | 626 | C | SER | A | 46 | 9.560 | 38.247 | 9.929 | 1.00 | 37.81 | C |
| ATOM | 627 | O | SER | A | 46 | 9.312 | 38.871 | 10.942 | 1.00 | 39.88 | O |
| ATOM | 629 | N | LYS | A | 47 | 9.961 | 36.983 | 9.939 | 1.00 | 38.55 | N |
| ATOM | 630 | CA | LYS | A | 47 | 10.216 | 36.271 | 11.181 | 1.00 | 40.42 | C |
| ATOM | 632 | CB | LYS | A | 47 | 10.092 | 34.774 | 10.981 | 1.00 | 41.17 | C |
| ATOM | 635 | CG | LYS | A | 47 | 8.812 | 34.303 | 10.319 | 1.00 | 45.31 | C |
| ATOM | 638 | CD | LYS | A | 47 | 7.580 | 34.744 | 11.070 | 1.00 | 52.31 | C |
| ATOM | 641 | CE | LYS | A | 47 | 6.506 | 33.679 | 11.011 | 1.00 | 54.03 | C |
| ATOM | 644 | NZ | LYS | A | 47 | 6.221 | 33.236 | 9.622 | 1.00 | 59.10 | N |
| ATOM | 648 | C | LYS | A | 47 | 11.603 | 36.560 | 11.743 | 1.00 | 41.47 | C |
| ATOM | 649 | O | LYS | A | 47 | 11.904 | 36.156 | 12.861 | 1.00 | 42.49 | O |
| ATOM | 651 | N | LYS | A | 48 | 12.446 | 37.219 | 10.955 | 1.00 | 41.00 | N |
| ATOM | 652 | CA | LYS | A | 48 | 13.749 | 37.684 | 11.408 | 1.00 | 40.18 | C |
| ATOM | 654 | CB | LYS | A | 48 | 14.846 | 37.343 | 10.379 | 1.00 | 39.77 | C |
| ATOM | 657 | CG | LYS | A | 48 | 14.877 | 35.961 | 9.844 | 1.00 | 45.55 | C |
| ATOM | 660 | CD | LYS | A | 48 | 15.986 | 35.867 | 8.813 | 1.00 | 42.47 | C |
| ATOM | 665 | C | LYS | A | 48 | 13.738 | 39.206 | 11.623 | 1.00 | 37.85 | C |
| ATOM | 666 | O | LYS | A | 48 | 14.807 | 39.821 | 11.684 | 1.00 | 37.26 | O |
| ATOM | 668 | N | PHE | A | 49 | 12.562 | 39.825 | 11.759 | 1.00 | 37.48 | N |
| ATOM | 669 | CA | PHE | A | 49 | 12.499 | 41.282 | 11.939 | 1.00 | 37.11 | C |
| ATOM | 671 | CB | PHE | A | 49 | 11.074 | 41.750 | 12.286 | 1.00 | 37.44 | C |
| ATOM | 674 | CG | PHE | A | 49 | 10.857 | 43.238 | 12.085 | 1.00 | 33.96 | C |
| ATOM | 675 | CD1 | PHE | A | 49 | 11.144 | 44.141 | 13.098 | 1.00 | 35.91 | C |
| ATOM | 677 | CE1 | PHE | A | 49 | 10.997 | 45.500 | 12.888 | 1.00 | 37.52 | C |
| ATOM | 679 | CZ | PHE | A | 49 | 10.556 | 45.992 | 11.657 | 1.00 | 33.77 | C |
| ATOM | 681 | CE2 | PHE | A | 49 | 10.247 | 45.131 | 10.658 | 1.00 | 34.82 | C |
| ATOM | 683 | CD2 | PHE | A | 49 | 10.435 | 43.761 | 10.848 | 1.00 | 33.51 | C |
| ATOM | 685 | C | PHE | A | 49 | 13.536 | 41.744 | 13.000 | 1.00 | 36.81 | C |
| ATOM | 686 | O | PHE | A | 49 | 13.664 | 41.127 | 14.052 | 1.00 | 36.70 | O |
| ATOM | 688 | N | PRO | A | 50 | 14.296 | 42.824 | 12.729 | 1.00 | 33.27 | N |
| ATOM | 689 | CA | PRO | A | 50 | 14.246 | 43.848 | 11.685 | 1.00 | 32.94 | C |
| ATOM | 691 | CB | PRO | A | 50 | 15.136 | 44.918 | 12.283 | 1.00 | 31.28 | C |
| ATOM | 694 | CG | PRO | A | 50 | 16.201 | 44.084 | 12.965 | 1.00 | 28.61 | C |
| ATOM | 697 | CD | PRO | A | 50 | 15.392 | 43.099 | 13.671 | 1.00 | 35.70 | C |
| ATOM | 700 | C | PRO | A | 50 | 14.793 | 43.431 | 10.298 | 1.00 | 34.14 | C |
| ATOM | 701 | O | PRO | A | 50 | 14.749 | 44.239 | 9.362 | 1.00 | 37.04 | O |

TABLE 2-continued

| | | | | | | | | |
|---|---|---|---|---|---|---|---|---|
| ATOM | 702 | N | PHE | A | 51 | 15.312 | 42.221 | 10.166 | 1.00 | 36.74 | N |
| ATOM | 703 | CA | PHE | A | 51 | 15.829 | 41.760 | 8.887 | 1.00 | 37.75 | C |
| ATOM | 705 | CB | PHE | A | 51 | 17.013 | 40.818 | 9.100 | 1.00 | 37.23 | C |
| ATOM | 708 | CG | PHE | A | 51 | 18.106 | 41.444 | 9.905 | 1.00 | 40.75 | C |
| ATOM | 709 | CD1 | PHE | A | 51 | 18.947 | 42.392 | 9.338 | 1.00 | 42.00 | C |
| ATOM | 711 | CE1 | PHE | A | 51 | 19.923 | 43.020 | 10.094 | 1.00 | 42.82 | C |
| ATOM | 713 | CZ | PHE | A | 51 | 20.057 | 42.708 | 11.438 | 1.00 | 40.78 | C |
| ATOM | 715 | CE2 | PHE | A | 51 | 19.224 | 41.770 | 12.017 | 1.00 | 39.46 | C |
| ATOM | 717 | CD2 | PHE | A | 51 | 18.241 | 41.150 | 11.253 | 1.00 | 40.01 | C |
| ATOM | 719 | C | PHE | A | 51 | 14.761 | 41.143 | 8.003 | 1.00 | 37.07 | C |
| ATOM | 720 | O | PHE | A | 51 | 13.829 | 40.486 | 8.477 | 1.00 | 38.66 | O |
| ATOM | 722 | N | CYS | A | 52 | 14.918 | 41.373 | 6.706 | 1.00 | 37.25 | N |
| ATOM | 723 | CA | CYS | A | 52 | 14.051 | 40.806 | 5.669 | 1.00 | 36.10 | C |
| ATOM | 725 | CB | CYS | A | 52 | 14.277 | 41.583 | 4.370 | 1.00 | 36.39 | C |
| ATOM | 728 | SG | CYS | A | 52 | 13.404 | 40.992 | 2.908 | 1.00 | 36.61 | S |
| ATOM | 730 | C | CYS | A | 52 | 14.305 | 39.303 | 5.433 | 1.00 | 36.63 | C |
| ATOM | 731 | O | CYS | A | 52 | 15.449 | 38.839 | 5.316 | 1.00 | 37.89 | O |
| ATOM | 733 | N | ASP | A | 53 | 13.221 | 38.544 | 5.389 | 1.00 | 36.35 | N |
| ATOM | 734 | CA | ASP | A | 53 | 13.281 | 37.104 | 5.118 | 1.00 | 35.46 | C |
| ATOM | 736 | CB | ASP | A | 53 | 12.892 | 36.266 | 6.362 | 1.00 | 35.84 | C |
| ATOM | 739 | CG | ASP | A | 53 | 11.375 | 36.303 | 6.683 | 1.00 | 35.22 | C |
| ATOM | 740 | OD1 | ASP | A | 53 | 10.615 | 37.060 | 6.015 | 1.00 | 36.99 | O |
| ATOM | 741 | OD2 | ASP | A | 53 | 10.960 | 35.604 | 7.630 | 1.00 | 38.50 | O |
| ATOM | 742 | C | ASP | A | 53 | 12.424 | 37.704 | 5.193 | 1.00 | 36.08 | C |
| ATOM | 743 | O | ASP | A | 53 | 12.141 | 36.697 | 3.912 | 1.00 | 36.69 | O |
| ATOM | 745 | N | GLY | A | 54 | 12.006 | 35.502 | 3.728 | 1.00 | 37.36 | N |
| ATOM | 746 | CA | GLY | A | 54 | 11.244 | 37.693 | 3.120 | 1.00 | 36.61 | C |
| ATOM | 749 | C | GLY | A | 54 | 9.749 | 37.449 | 1.899 | 1.00 | 36.32 | C |
| ATOM | 750 | O | GLY | A | 54 | 8.999 | 37.360 | 2.118 | 1.00 | 36.32 | O |
| ATOM | 752 | N | ALA | A | 55 | 9.310 | 37.131 | 1.177 | 1.00 | 35.99 | N |
| ATOM | 753 | CA | ALA | A | 55 | 7.877 | 37.580 | 3.352 | 1.00 | 34.94 | C |
| ATOM | 755 | CB | ALA | A | 55 | 7.682 | 37.580 | 3.680 | 1.00 | 34.04 | C |
| ATOM | 759 | C | ALA | A | 55 | 7.070 | 37.704 | 5.193 | 1.00 | 35.64 | C |
| ATOM | 760 | O | ALA | A | 55 | 5.858 | 38.659 | 2.926 | 1.00 | 36.86 | O |
| ATOM | 762 | N | HIS | A | 56 | 7.739 | 38.516 | 2.730 | 1.00 | 36.39 | N |
| ATOM | 763 | CA | HIS | A | 56 | 7.082 | 39.717 | 2.483 | 1.00 | 36.67 | C |
| ATOM | 765 | CB | HIS | A | 56 | 8.055 | 40.736 | 1.671 | 1.00 | 35.06 | C |
| ATOM | 768 | CG | HIS | A | 56 | 9.254 | 41.867 | 1.298 | 1.00 | 36.52 | C |
| ATOM | 769 | ND1 | HIS | A | 56 | 10.462 | 41.422 | 0.519 | 1.00 | 34.28 | N |
| ATOM | 771 | CE1 | HIS | A | 56 | 11.322 | 41.111 | 1.111 | 1.00 | 36.99 | C |
| ATOM | 773 | NE2 | HIS | A | 56 | 10.724 | 40.736 | 0.181 | 1.00 | 36.11 | N |
| ATOM | 775 | CD2 | HIS | A | 56 | 9.431 | 40.811 | -0.993 | 1.00 | 39.32 | C |
| ATOM | 777 | C | HIS | A | 56 | 6.405 | 41.229 | -0.810 | 1.00 | 37.72 | C |
| ATOM | 778 | O | HIS | A | 56 | 5.361 | 40.206 | 0.414 | 1.00 | 36.64 | O |
| ATOM | 780 | N | THR | A | 57 | 6.992 | 40.706 | 0.010 | 1.00 | 37.59 | N |
| ATOM | 781 | CA | THR | A | 57 | 6.475 | 39.188 | -0.200 | 1.00 | 38.85 | C |
| ATOM | 783 | CB | THR | A | 57 | 7.415 | 38.653 | -1.461 | 1.00 | 38.29 | C |
| ATOM | 785 | OG1 | THR | A | 57 | 7.582 | 37.587 | -2.101 | 1.00 | 43.81 | O |
| ATOM | 787 | CG2 | THR | A | 57 | 8.770 | 36.484 | -1.220 | 1.00 | 37.53 | C |
| ATOM | 791 | C | THR | A | 57 | 5.068 | 38.145 | -2.380 | 1.00 | 39.20 | C |
| ATOM | 792 | O | THR | A | 57 | 4.162 | 38.096 | -1.244 | 1.00 | 38.27 | O |
| ATOM | 794 | N | LYS | A | 58 | 4.881 | 38.390 | -2.009 | 1.00 | 40.72 | N |
| ATOM | 795 | CA | LYS | A | 58 | 3.561 | 36.803 | -0.173 | 1.00 | 41.57 | C |

TABLE 2-continued

| | | | | | | | | | |
|---|---|---|---|---|---|---|---|---|---|
| ATOM | 797 | CB | LYS | A | 58 | 3.672 | 35.829 | 1.374 | 1.00 | 42.03 | C |
| ATOM | 800 | CG | LYS | A | 58 | 2.363 | 35.210 | 1.820 | 1.00 | 41.79 | C |
| ATOM | 803 | CD | LYS | A | 58 | 2.554 | 34.300 | 3.034 | 1.00 | 43.27 | C |
| ATOM | 808 | C | LYS | A | 58 | 2.591 | 37.926 | 0.529 | 1.00 | 40.69 | C |
| ATOM | 809 | O | LYS | A | 58 | 1.440 | 37.917 | 0.098 | 1.00 | 41.22 | O |
| ATOM | 811 | N | HIS | A | 59 | 3.051 | 38.893 | 1.314 | 1.00 | 40.28 | N |
| ATOM | 812 | CA | HIS | A | 59 | 2.178 | 40.009 | 1.654 | 1.00 | 39.50 | C |
| ATOM | 814 | CB | HIS | A | 59 | 2.895 | 41.015 | 2.546 | 1.00 | 38.66 | C |
| ATOM | 817 | CG | HIS | A | 59 | 2.233 | 42.347 | 2.570 | 1.00 | 39.42 | C |
| ATOM | 818 | ND1 | HIS | A | 59 | 1.113 | 42.607 | 3.326 | 1.00 | 35.66 | N |
| ATOM | 820 | CE1 | HIS | A | 59 | 0.726 | 43.853 | 3.116 | 1.00 | 40.37 | C |
| ATOM | 822 | NE2 | HIS | A | 59 | 1.551 | 44.404 | 2.242 | 1.00 | 38.31 | N |
| ATOM | 824 | CD2 | HIS | A | 59 | 2.482 | 43.470 | 1.864 | 1.00 | 38.67 | C |
| ATOM | 826 | C | HIS | A | 59 | 1.656 | 40.697 | 0.381 | 1.00 | 38.15 | C |
| ATOM | 827 | O | HIS | A | 59 | 0.454 | 40.948 | 0.246 | 1.00 | 36.11 | O |
| ATOM | 829 | N | ASN | A | 60 | 2.585 | 41.015 | -0.525 | 1.00 | 36.82 | N |
| ATOM | 830 | CA | ASN | A | 60 | 2.252 | 41.660 | -1.791 | 1.00 | 36.61 | C |
| ATOM | 832 | CB | ASN | A | 60 | 3.519 | 41.942 | -2.604 | 1.00 | 35.69 | C |
| ATOM | 835 | CG | ASN | A | 60 | 4.356 | 43.079 | -2.039 | 1.00 | 31.55 | C |
| ATOM | 836 | OD1 | ASN | A | 60 | 3.913 | 43.853 | -1.167 | 1.00 | 35.97 | O |
| ATOM | 837 | ND2 | ASN | A | 60 | 5.596 | 43.196 | -2.536 | 1.00 | 34.23 | N |
| ATOM | 840 | C | ASN | A | 60 | 1.306 | 40.817 | -2.633 | 1.00 | 37.82 | C |
| ATOM | 841 | O | ASN | A | 60 | 0.394 | 41.339 | -3.264 | 1.00 | 37.28 | O |
| ATOM | 843 | N | GLU | A | 61 | 1.528 | 39.510 | -2.663 | 1.00 | 39.95 | N |
| ATOM | 844 | CA | GLU | A | 61 | 0.664 | 38.630 | -3.424 | 1.00 | 41.50 | C |
| ATOM | 846 | CB | GLU | A | 61 | 1.255 | 37.220 | -3.506 | 1.00 | 41.85 | C |
| ATOM | 849 | CG | GLU | A | 61 | 0.494 | 36.255 | -4.408 | 1.00 | 47.15 | C |
| ATOM | 852 | CD | GLU | A | 61 | 0.505 | 36.648 | -5.893 | 1.00 | 52.13 | C |
| ATOM | 853 | OE1 | GLU | A | 61 | 1.535 | 37.179 | -6.379 | 1.00 | 54.08 | O |
| ATOM | 854 | OE2 | GLU | A | 61 | -0.519 | 36.396 | -6.580 | 1.00 | 54.75 | O |
| ATOM | 855 | C | GLU | A | 61 | -0.730 | 38.599 | -2.808 | 1.00 | 41.78 | C |
| ATOM | 856 | O | GLU | A | 61 | -1.725 | 38.648 | -3.536 | 1.00 | 42.61 | O |
| ATOM | 858 | N | GLU | A | 62 | -0.789 | 38.538 | -1.477 | 1.00 | 41.24 | N |
| ATOM | 859 | CA | GLU | A | 62 | -2.054 | 38.432 | -0.740 | 1.00 | 42.59 | C |
| ATOM | 861 | CB | GLU | A | 62 | -1.793 | 38.063 | 0.741 | 1.00 | 42.75 | C |
| ATOM | 864 | CG | GLU | A | 62 | -1.538 | 36.552 | 0.993 | 1.00 | 46.31 | C |
| ATOM | 867 | CD | GLU | A | 62 | -1.051 | 36.218 | 2.419 | 1.00 | 45.09 | C |
| ATOM | 868 | OE1 | GLU | A | 62 | -0.728 | 37.141 | 3.193 | 1.00 | 51.04 | O |
| ATOM | 869 | OE2 | GLU | A | 62 | -0.982 | 35.017 | 2.763 | 1.00 | 54.23 | O |
| ATOM | 870 | C | GLU | A | 62 | -2.916 | 39.698 | -0.812 | 1.00 | 41.43 | C |
| ATOM | 871 | O | GLU | A | 62 | -4.143 | 39.605 | -0.808 | 1.00 | 41.36 | O |
| ATOM | 873 | N | THR | A | 63 | -2.273 | 40.865 | -0.867 | 1.00 | 41.46 | N |
| ATOM | 874 | CA | THR | A | 63 | -2.956 | 42.163 | -0.725 | 1.00 | 39.50 | C |
| ATOM | 876 | CB | THR | A | 63 | -2.345 | 42.991 | 0.435 | 1.00 | 39.55 | C |
| ATOM | 878 | OG1 | THR | A | 63 | -0.960 | 43.289 | 0.178 | 1.00 | 38.99 | O |
| ATOM | 880 | CG2 | THR | A | 63 | -2.464 | 42.220 | 1.739 | 1.00 | 40.68 | C |
| ATOM | 884 | C | THR | A | 63 | -2.929 | 43.035 | -1.972 | 1.00 | 38.82 | C |
| ATOM | 885 | O | THR | A | 63 | -3.650 | 44.021 | -2.035 | 1.00 | 39.22 | O |
| ATOM | 887 | N | GLY | A | 64 | -2.089 | 42.699 | -2.946 | 1.00 | 38.08 | N |
| ATOM | 888 | CA | GLY | A | 64 | -1.892 | 43.556 | -4.110 | 1.00 | 37.43 | C |
| ATOM | 891 | C | GLY | A | 64 | -0.972 | 44.738 | -3.850 | 1.00 | 36.37 | C |
| ATOM | 892 | O | GLY | A | 64 | -0.922 | 45.676 | -4.646 | 1.00 | 35.54 | O |
| ATOM | 894 | N | ASP | A | 65 | -0.216 | 44.668 | -2.752 | 1.00 | 35.88 | N |

TABLE 2-continued

| | | | | | | | | |
|---|---|---|---|---|---|---|---|---|
| ATOM | 895 | CA | ASP | A | 65 | 0.716 | 45.708 | -2.366 | 1.00 | 34.61 | C |
| ATOM | 897 | CB | ASP | A | 65 | 0.945 | 45.652 | -0.847 | 1.00 | 34.40 | C |
| ATOM | 900 | CG | ASP | A | 65 | 1.299 | 47.006 | -0.216 | 1.00 | 33.66 | C |
| ATOM | 901 | OD1 | ASP | A | 65 | 1.533 | 48.013 | -0.923 | 1.00 | 33.72 | O |
| ATOM | 902 | OD2 | ASP | A | 65 | 1.392 | 47.055 | 1.026 | 1.00 | 36.10 | O |
| ATOM | 903 | C | ASP | A | 65 | 2.025 | 45.546 | -3.155 | 1.00 | 34.18 | C |
| ATOM | 904 | O | ASP | A | 65 | 2.195 | 44.591 | -3.935 | 1.00 | 33.96 | O |
| ATOM | 906 | N | ASN | A | 66 | 2.930 | 46.504 | -2.947 | 1.00 | 34.32 | N |
| ATOM | 907 | CA | ASN | A | 66 | 4.181 | 46.641 | -3.692 | 1.00 | 32.71 | C |
| ATOM | 909 | CB | ASN | A | 66 | 3.996 | 47.644 | -4.837 | 1.00 | 33.00 | C |
| ATOM | 912 | CG | ASN | A | 66 | 3.866 | 49.094 | -4.366 | 1.00 | 33.98 | C |
| ATOM | 913 | OD1 | ASN | A | 66 | 3.457 | 49.373 | -3.238 | 1.00 | 34.61 | O |
| ATOM | 914 | ND2 | ASN | A | 66 | 4.236 | 50.028 | -5.238 | 1.00 | 33.60 | N |
| ATOM | 917 | C | ASN | A | 66 | 5.352 | 47.051 | -2.788 | 1.00 | 34.31 | C |
| ATOM | 918 | O | ASN | A | 66 | 6.221 | 47.817 | -3.191 | 1.00 | 33.98 | O |
| ATOM | 920 | N | VAL | A | 67 | 5.360 | 46.549 | -1.560 | 1.00 | 35.34 | N |
| ATOM | 921 | CA | VAL | A | 67 | 6.388 | 46.899 | -0.612 | 1.00 | 34.64 | C |
| ATOM | 923 | CB | VAL | A | 67 | 5.854 | 46.915 | 0.858 | 1.00 | 35.36 | C |
| ATOM | 925 | CG1 | VAL | A | 67 | 4.844 | 48.070 | 1.032 | 1.00 | 37.21 | C |
| ATOM | 929 | CG2 | VAL | A | 67 | 5.273 | 45.549 | 1.273 | 1.00 | 34.88 | C |
| ATOM | 933 | C | VAL | A | 67 | 7.578 | 45.958 | -0.732 | 1.00 | 35.31 | C |
| ATOM | 934 | O | VAL | A | 67 | 7.444 | 44.837 | -1.178 | 1.00 | 34.76 | O |
| ATOM | 936 | N | GLY | A | 68 | 8.737 | 46.426 | -0.313 | 1.00 | 35.69 | N |
| ATOM | 937 | CA | GLY | A | 68 | 9.929 | 45.595 | -0.271 | 1.00 | 35.36 | C |
| ATOM | 940 | C | GLY | A | 68 | 10.949 | 46.184 | 0.683 | 1.00 | 34.21 | C |
| ATOM | 941 | O | GLY | A | 68 | 10.682 | 47.229 | 1.286 | 1.00 | 35.18 | O |
| ATOM | 943 | N | PRO | A | 69 | 12.097 | 45.534 | 0.842 | 1.00 | 35.51 | N |
| ATOM | 944 | CA | PRO | A | 69 | 13.105 | 45.935 | 1.829 | 1.00 | 35.08 | C |
| ATOM | 946 | CB | PRO | A | 69 | 13.959 | 44.660 | 1.969 | 1.00 | 35.63 | C |
| ATOM | 949 | CG | PRO | A | 69 | 13.900 | 44.049 | 0.607 | 1.00 | 36.47 | C |
| ATOM | 952 | CD | PRO | A | 69 | 12.485 | 44.289 | 0.144 | 1.00 | 34.26 | C |
| ATOM | 955 | C | PRO | A | 69 | 14.012 | 47.149 | 1.528 | 1.00 | 34.98 | C |
| ATOM | 956 | O | PRO | A | 69 | 14.027 | 47.707 | 0.427 | 1.00 | 32.18 | O |
| ATOM | 957 | N | LEU | A | 70 | 14.756 | 47.517 | 2.561 | 1.00 | 35.82 | N |
| ATOM | 958 | CA | LEU | A | 70 | 15.837 | 48.483 | 2.517 | 1.00 | 36.21 | C |
| ATOM | 960 | CB | LEU | A | 70 | 15.676 | 49.441 | 3.673 | 1.00 | 36.75 | C |
| ATOM | 963 | CG | LEU | A | 70 | 16.745 | 50.514 | 3.740 | 1.00 | 41.85 | C |
| ATOM | 965 | CD1 | LEU | A | 70 | 16.416 | 51.633 | 2.773 | 1.00 | 41.88 | C |
| ATOM | 969 | CD2 | LEU | A | 70 | 16.855 | 51.012 | 5.131 | 1.00 | 43.85 | C |
| ATOM | 973 | C | LEU | A | 70 | 17.170 | 47.753 | 2.661 | 1.00 | 35.60 | C |
| ATOM | 974 | O | LEU | A | 70 | 17.406 | 47.032 | 3.629 | 1.00 | 36.87 | O |
| ATOM | 976 | N | ILE | A | 71 | 18.037 | 47.970 | 1.681 | 1.00 | 33.62 | N |
| ATOM | 977 | CA | ILE | A | 71 | 19.349 | 47.351 | 1.636 | 1.00 | 33.24 | C |
| ATOM | 979 | CB | ILE | A | 71 | 19.602 | 46.709 | 0.257 | 1.00 | 33.05 | C |
| ATOM | 981 | CG2 | ILE | A | 71 | 18.550 | 45.633 | -0.036 | 1.00 | 36.10 | C |
| ATOM | 984 | CG1 | ILE | A | 71 | 18.537 | 45.173 | -1.469 | 1.00 | 36.33 | C |
| ATOM | 988 | CD1 | ILE | A | 71 | 21.016 | 46.156 | 0.141 | 1.00 | 32.67 | C |
| ATOM | 992 | C | ILE | A | 71 | 16.855 | 48.390 | 1.932 | 1.00 | 33.10 | C |
| ATOM | 993 | O | ILE | A | 71 | 20.407 | 49.455 | 1.334 | 1.00 | 33.68 | O |
| ATOM | 995 | N | ILE | A | 72 | 20.445 | 48.042 | 2.867 | 1.00 | 32.95 | N |
| ATOM | 996 | CA | ILE | A | 72 | 21.290 | 48.839 | 3.181 | 1.00 | 34.16 | C |
| ATOM | 998 | CB | ILE | A | 72 | 22.471 | 49.269 | 4.671 | 1.00 | 33.21 | C |
| ATOM | 1000 | CG1 | ILE | A | 72 | 21.245 | 50.091 | 5.016 | 1.00 | 39.87 | C |

TABLE 2-continued

| | | | | | | | | |
|---|---|---|---|---|---|---|---|---|
| ATOM | 1003 | CD1 | ILE | A | 72 | 21.078 | 51.376 | 4.233 | 1.00 | 37.06 | C |
| ATOM | 1007 | CG2 | ILE | A | 72 | 23.751 | 50.054 | 4.976 | 1.00 | 32.17 | C |
| ATOM | 1011 | C | ILE | A | 72 | 23.664 | 47.967 | 2.863 | 1.00 | 34.90 | C |
| ATOM | 1012 | O | ILE | A | 72 | 23.767 | 46.864 | 3.380 | 1.00 | 36.95 | O |
| ATOM | 1014 | N | LYS | A | 73 | 24.564 | 48.453 | 2.016 | 1.00 | 34.50 | N |
| ATOM | 1015 | CA | LYS | A | 73 | 25.635 | 47.622 | 1.498 | 1.00 | 35.69 | C |
| ATOM | 1017 | CB | LYS | A | 73 | 25.186 | 46.968 | 0.186 | 1.00 | 35.94 | C |
| ATOM | 1020 | CG | LYS | A | 73 | 25.194 | 47.930 | -0.971 | 1.00 | 36.54 | C |
| ATOM | 1023 | CD | LYS | A | 73 | 24.274 | 47.229 | -2.144 | 1.00 | 37.34 | C |
| ATOM | 1026 | CE | LYS | A | 73 | 24.193 | 48.123 | -3.379 | 1.00 | 38.41 | C |
| ATOM | 1029 | NZ | LYS | A | 73 | 25.521 | 48.419 | -3.991 | 1.00 | 39.30 | N |
| ATOM | 1033 | C | LYS | A | 73 | 26.923 | 48.385 | 1.304 | 1.00 | 35.65 | C |
| ATOM | 1034 | O | LYS | A | 73 | 26.962 | 49.600 | 1.349 | 1.00 | 34.71 | O |
| ATOM | 1036 | N | LYS | A | 74 | 27.994 | 47.633 | 1.117 | 1.00 | 36.83 | N |
| ATOM | 1037 | CA | LYS | A | 74 | 29.287 | 48.187 | 0.759 | 1.00 | 38.96 | C |
| ATOM | 1039 | CB | LYS | A | 74 | 30.400 | 47.245 | 1.200 | 1.00 | 39.48 | C |
| ATOM | 1042 | CG | LYS | A | 74 | 30.522 | 47.075 | 2.707 | 1.00 | 41.12 | C |
| ATOM | 1045 | CD | LYS | A | 74 | 31.495 | 48.076 | 3.326 | 1.00 | 43.36 | C |
| ATOM | 1048 | CE | LYS | A | 74 | 32.168 | 47.538 | 4.604 | 1.00 | 42.28 | C |
| ATOM | 1051 | NZ | LYS | A | 74 | 31.523 | 47.986 | 5.858 | 1.00 | 43.48 | N |
| ATOM | 1055 | C | LYS | A | 74 | 29.330 | 48.397 | -0.748 | 1.00 | 39.24 | C |
| ATOM | 1056 | O | LYS | A | 74 | 28.850 | 47.563 | -1.512 | 1.00 | 39.78 | O |
| ATOM | 1058 | N | LYS | A | 75 | 29.866 | 49.542 | -1.152 | 1.00 | 40.53 | N |
| ATOM | 1059 | CA | LYS | A | 75 | 30.108 | 49.858 | -2.555 | 1.00 | 41.85 | C |
| ATOM | 1061 | CB | LYS | A | 75 | 30.598 | 51.313 | -2.694 | 1.00 | 41.81 | C |
| ATOM | 1064 | CG | LYS | A | 75 | 30.605 | 51.853 | -4.121 | 1.00 | 43.15 | C |
| ATOM | 1067 | CD | LYS | A | 75 | 30.997 | 53.339 | -4.192 | 1.00 | 42.87 | C |
| ATOM | 1070 | CE | LYS | A | 75 | 29.887 | 54.262 | -3.712 | 1.00 | 45.05 | C |
| ATOM | 1074 | C | LYS | A | 75 | 31.148 | 48.895 | -3.127 | 1.00 | 42.66 | C |
| ATOM | 1075 | O | LYS | A | 75 | 30.890 | 48.211 | -4.119 | 1.00 | 43.78 | O |
| ATOM | 1077 | S2 | FES | A | 500 | 10.405 | 43.634 | 3.488 | 1.00 | 35.36 | S |
| ATOM | 1078 | FE2 | FES | A | 500 | 11.183 | 41.582 | 3.132 | 1.00 | 37.29 | FE |
| ATOM | 1079 | S1 | FES | A | 500 | 10.279 | 40.462 | 4.817 | 1.00 | 36.70 | S |
| ATOM | 1080 | FE1 | FES | A | 500 | 9.523 | 42.479 | 5.116 | 1.00 | 34.87 | FE |
| ATOM | 1081 | N | ALA | B | 12 | -5.546 | 44.225 | 3.700 | 1.00 | 42.96 | N |
| ATOM | 1082 | CA | ALA | B | 12 | -5.078 | 45.640 | 3.808 | 1.00 | 42.60 | C |
| ATOM | 1084 | CB | ALA | B | 12 | -5.148 | 46.127 | 5.249 | 1.00 | 43.65 | C |
| ATOM | 1088 | C | ALA | B | 12 | -3.656 | 45.790 | 3.281 | 1.00 | 41.86 | C |
| ATOM | 1089 | O | ALA | B | 12 | -2.751 | 45.064 | 3.690 | 1.00 | 42.41 | O |
| ATOM | 1093 | N | MET | B | 13 | -3.463 | 46.745 | 2.378 | 1.00 | 41.91 | N |
| ATOM | 1094 | CA | MET | B | 13 | -2.122 | 47.143 | 1.967 | 1.00 | 40.79 | C |
| ATOM | 1096 | CB | MET | B | 13 | -2.167 | 47.944 | 0.671 | 1.00 | 40.29 | C |
| ATOM | 1099 | CG | MET | B | 13 | -2.772 | 47.190 | -0.491 | 1.00 | 42.26 | C |
| ATOM | 1102 | SD | MET | B | 13 | -2.375 | 47.950 | -2.070 | 1.00 | 41.37 | S |
| ATOM | 1103 | CE | MET | B | 13 | -3.124 | 49.563 | -1.912 | 1.00 | 41.08 | C |
| ATOM | 1107 | C | MET | B | 13 | -1.450 | 47.982 | 3.046 | 1.00 | 40.51 | C |
| ATOM | 1108 | O | MET | B | 13 | -2.104 | 48.706 | 3.808 | 1.00 | 40.98 | O |
| ATOM | 1110 | N | ILE | B | 14 | -0.135 | 47.866 | 3.090 | 1.00 | 38.91 | N |
| ATOM | 1111 | CA | ILE | B | 14 | 0.702 | 48.676 | 3.956 | 1.00 | 39.12 | C |
| ATOM | 1113 | CB | ILE | B | 14 | 2.002 | 47.908 | 4.284 | 1.00 | 39.53 | C |
| ATOM | 1115 | CG2 | ILE | B | 14 | 1.669 | 46.700 | 5.169 | 1.00 | 39.21 | C |
| ATOM | 1118 | CD1 | ILE | B | 14 | 2.795 | 45.684 | 5.315 | 1.00 | 40.36 | C |
| ATOM | 1122 | CG2 | ILE | B | 14 | 3.021 | 48.799 | 4.952 | 1.00 | 42.41 | C |

TABLE 2-continued

| | | | | | | | | | |
|---|---|---|---|---|---|---|---|---|---|
| ATOM | 1126 | C | ILE | B | 14 | 0.979 | 50.023 | 3.285 | 1.00 | 37.32 | C |
| ATOM | 1127 | O | ILE | B | 14 | 0.716 | 51.082 | 3.856 | 1.00 | 37.10 | O |
| ATOM | 1129 | N | ASN | B | 15 | 1.476 | 49.979 | 2.055 | 1.00 | 36.96 | N |
| ATOM | 1130 | CA | ASN | B | 15 | 1.710 | 51.184 | 1.263 | 1.00 | 35.02 | C |
| ATOM | 1132 | CB | ASN | B | 15 | 2.908 | 50.995 | 0.317 | 1.00 | 34.62 | C |
| ATOM | 1135 | CG | ASN | B | 15 | 3.107 | 52.166 | −0.619 | 1.00 | 34.27 | C |
| ATOM | 1136 | OD1 | ASN | B | 15 | 2.814 | 53.323 | −0.272 | 1.00 | 34.93 | O |
| ATOM | 1137 | ND2 | ASN | B | 15 | 3.573 | 51.872 | −1.839 | 1.00 | 34.25 | N |
| ATOM | 1140 | C | ASN | B | 15 | 0.447 | 51.588 | 0.522 | 1.00 | 37.31 | C |
| ATOM | 1141 | O | ASN | B | 15 | −0.142 | 50.797 | −0.207 | 1.00 | 36.96 | O |
| ATOM | 1143 | N | LEU | B | 16 | 0.014 | 52.826 | 0.744 | 1.00 | 40.46 | N |
| ATOM | 1144 | CA | LEU | B | 16 | −1.181 | 53.331 | 0.107 | 1.00 | 40.10 | C |
| ATOM | 1146 | CB | LEU | B | 16 | −1.986 | 54.207 | 1.077 | 1.00 | 40.79 | C |
| ATOM | 1149 | CG | LEU | B | 16 | −2.314 | 53.614 | 2.445 | 1.00 | 39.70 | C |
| ATOM | 1151 | CD1 | LEU | B | 16 | −3.195 | 54.564 | 3.216 | 1.00 | 42.74 | C |
| ATOM | 1155 | CD2 | LEU | B | 16 | −2.980 | 52.263 | 2.270 | 1.00 | 42.18 | C |
| ATOM | 1159 | C | LEU | B | 16 | −0.925 | 54.123 | −1.171 | 1.00 | 39.13 | C |
| ATOM | 1160 | O | LEU | B | 16 | −1.721 | 54.015 | −2.097 | 1.00 | 39.60 | O |
| ATOM | 1162 | N | HIS | B | 17 | 0.162 | 54.898 | −1.219 | 1.00 | 37.63 | N |
| ATOM | 1163 | CA | AHIS | B | 17 | 0.337 | 55.922 | −2.256 | 1.00 | 38.82 | C |
| ATOM | 1164 | CA | BHIS | B | 17 | 0.339 | 55.935 | −2.241 | 0.50 | 37.80 | C |
| ATOM | 1167 | CB | AHIS | B | 17 | −0.017 | 57.313 | −1.688 | 0.50 | 39.62 | C |
| ATOM | 1168 | CB | BHIS | B | 17 | 0.056 | 57.315 | −1.622 | 0.50 | 37.26 | C |
| ATOM | 1173 | CG | ANIS | B | 17 | 1.127 | 58.025 | −1.027 | 0.50 | 42.59 | C |
| ATOM | 1174 | CG | BHIS | B | 17 | −1.316 | 57.446 | −1.031 | 0.50 | 36.25 | C |
| ATOM | 1175 | ND1 | AHIS | B | 17 | 1.184 | 58.236 | 0.332 | 0.50 | 47.49 | N |
| ATOM | 1176 | ND1 | BHIS | B | 17 | −1.537 | 57.962 | 0.227 | 0.50 | 38.74 | N |
| ATOM | 1179 | CE1 | AHIS | B | 17 | 2.293 | 58.889 | 0.632 | 0.50 | 47.78 | C |
| ATOM | 1180 | CE1 | BHIS | B | 17 | −2.828 | 57.937 | 0.493 | 0.50 | 31.21 | C |
| ATOM | 1183 | NE2 | AHIS | B | 17 | 2.953 | 59.122 | −0.488 | 0.50 | 46.15 | N |
| ATOM | 1184 | NE2 | BHIS | B | 17 | −3.454 | 57.409 | −0.543 | 0.50 | 32.84 | N |
| ATOM | 1187 | CD2 | AHIS | B | 17 | 2.245 | 58.593 | −1.539 | 0.50 | 46.78 | C |
| ATOM | 1188 | CD2 | BHIS | B | 17 | −2.530 | 57.089 | −1.508 | 0.50 | 32.63 | C |
| ATOM | 1191 | C | HIS | B | 17 | 1.704 | 55.980 | −2.942 | 1.00 | 37.70 | C |
| ATOM | 1192 | O | HIS | B | 17 | 1.829 | 56.582 | −3.988 | 1.00 | 37.72 | O |
| ATOM | 1194 | N | ILE | B | 18 | 2.724 | 55.356 | −2.380 | 1.00 | 38.18 | N |
| ATOM | 1195 | CA | ILE | B | 18 | 4.106 | 55.532 | −2.863 | 1.00 | 39.47 | C |
| ATOM | 1197 | CB | ILE | B | 18 | 5.125 | 55.292 | −1.729 | 1.00 | 39.88 | C |
| ATOM | 1199 | CG1 | ILE | B | 18 | 4.922 | 56.339 | −0.618 | 1.00 | 39.55 | C |
| ATOM | 1202 | CD1 | ILE | B | 18 | 5.511 | 55.918 | 0.694 | 1.00 | 40.71 | C |
| ATOM | 1206 | CG2 | ILE | B | 18 | 6.537 | 55.348 | −2.260 | 1.00 | 39.30 | C |
| ATOM | 1210 | C | ILE | B | 18 | 4.407 | 54.658 | −4.100 | 1.00 | 38.86 | C |
| ATOM | 1211 | O | ILE | B | 18 | 4.129 | 53.459 | −4.080 | 1.00 | 37.60 | O |
| ATOM | 1213 | N | GLN | B | 19 | 4.925 | 55.299 | −5.161 | 1.00 | 39.40 | N |
| ATOM | 1214 | CA | GLN | B | 19 | 5.347 | 54.656 | −6.416 | 1.00 | 38.53 | C |
| ATOM | 1216 | CB | GLN | B | 19 | 6.791 | 54.186 | −6.333 | 1.00 | 39.82 | C |
| ATOM | 1219 | CG | GLN | B | 19 | 7.906 | 55.162 | −6.045 | 1.00 | 45.34 | C |
| ATOM | 1222 | CD | GLN | B | 19 | 9.245 | 54.399 | −5.917 | 1.00 | 44.54 | C |
| ATOM | 1223 | OE1 | GLN | B | 19 | 9.659 | 53.660 | −6.846 | 1.00 | 52.09 | O |
| ATOM | 1224 | NE2 | GLN | B | 19 | 9.914 | 54.540 | −4.758 | 1.00 | 51.27 | N |
| ATOM | 1227 | C | GLN | B | 19 | 4.541 | 53.425 | −6.780 | 1.00 | 34.66 | C |
| ATOM | 1228 | O | GLN | B | 19 | 5.093 | 52.331 | −6.872 | 1.00 | 34.39 | O |
| ATOM | 1230 | N | LYS | B | 20 | 3.241 | 53.576 | −6.986 | 1.00 | 33.90 | N |

TABLE 2-continued

| | | | | | | | | |
|---|---|---|---|---|---|---|---|---|
| ATOM | 1231 | CA | LYS | B | 20 | 2.398 | 52.408 | −7.270 | 1.00 | 33.83 | C |
| ATOM | 1233 | CB | LYS | B | 20 | 0.929 | 52.714 | −7.016 | 1.00 | 33.80 | C |
| ATOM | 1236 | CG | LYS | B | 20 | 0.538 | 52.791 | −5.528 | 1.00 | 34.33 | C |
| ATOM | 1239 | CD | LYS | B | 20 | 0.899 | 51.510 | −4.766 | 1.00 | 31.89 | C |
| ATOM | 1242 | CE | LYS | B | 20 | 0.321 | 51.440 | −3.381 | 1.00 | 33.29 | C |
| ATOM | 1245 | NZ | LYS | B | 20 | 0.607 | 50.130 | −2.799 | 1.00 | 33.15 | N |
| ATOM | 1249 | C | LYS | B | 20 | 2.597 | 51.801 | −8.666 | 1.00 | 32.27 | C |
| ATOM | 1250 | O | LYS | B | 20 | 2.071 | 50.730 | −8.947 | 1.00 | 33.29 | O |
| ATOM | 1252 | N | ASP | B | 21 | 3.359 | 52.490 | −9.519 | 1.00 | 31.26 | N |
| ATOM | 1253 | CA | AASP | B | 21 | 3.770 | 51.967 | −10.824 | 0.50 | 30.57 | C |
| ATOM | 1254 | CA | BASP | B | 21 | 3.750 | 51.950 | −10.824 | 0.50 | 30.47 | C |
| ATOM | 1257 | CB | AASP | B | 21 | 4.100 | 53.110 | −11.790 | 0.50 | 30.52 | C |
| ATOM | 1258 | CB | BASP | B | 21 | 4.047 | 53.084 | −11.806 | 0.50 | 30.41 | C |
| ATOM | 1263 | CG | AASP | B | 21 | 5.129 | 54.096 | −11.236 | 0.50 | 32.56 | C |
| ATOM | 1264 | CG | BASP | B | 21 | 2.812 | 53.939 | −12.120 | 0.50 | 31.05 | C |
| ATOM | 1265 | OD1 | AASP | B | 21 | 5.236 | 54.280 | −9.999 | 0.50 | 36.56 | O |
| ATOM | 1266 | OD1 | BASP | B | 21 | 1.666 | 53.426 | −12.111 | 0.50 | 36.30 | O |
| ATOM | 1267 | OD2 | AASP | B | 21 | 5.814 | 54.721 | −12.065 | 0.50 | 34.46 | O |
| ATOM | 1268 | OD2 | BASP | B | 21 | 2.989 | 55.139 | −12.414 | 0.50 | 35.14 | O |
| ATOM | 1269 | C | ASP | B | 21 | 4.947 | 51.006 | −10.726 | 1.00 | 30.64 | C |
| ATOM | 1270 | O | ASP | B | 21 | 5.314 | 50.380 | −11.716 | 1.00 | 30.64 | O |
| ATOM | 1272 | N | ASN | B | 22 | 5.546 | 50.916 | −9.541 | 1.00 | 30.93 | N |
| ATOM | 1273 | CA | ASN | B | 22 | 6.666 | 50.023 | −9.253 | 1.00 | 31.24 | C |
| ATOM | 1275 | CB | ASN | B | 22 | 7.676 | 50.756 | −8.358 | 1.00 | 31.07 | C |
| ATOM | 1278 | CG | ASN | B | 22 | 8.868 | 49.911 | −7.999 | 1.00 | 30.94 | C |
| ATOM | 1279 | OD1 | ASN | B | 22 | 8.878 | 48.719 | −8.263 | 1.00 | 32.43 | O |
| ATOM | 1280 | ND2 | ASN | B | 22 | 9.883 | 50.524 | −7.405 | 1.00 | 33.72 | N |
| ATOM | 1283 | C | ASN | B | 22 | 6.064 | 48.800 | −8.548 | 1.00 | 32.14 | C |
| ATOM | 1284 | O | ASN | B | 22 | 5.467 | 48.951 | −7.483 | 1.00 | 31.12 | O |
| ATOM | 1286 | N | PRO | B | 23 | 6.201 | 47.597 | −9.137 | 1.00 | 31.88 | N |
| ATOM | 1287 | CA | PRO | B | 23 | 5.568 | 46.413 | −8.528 | 1.00 | 32.35 | C |
| ATOM | 1289 | CB | PRO | B | 23 | 5.712 | 45.347 | −9.611 | 1.00 | 33.37 | C |
| ATOM | 1292 | CG | PRO | B | 23 | 6.849 | 45.773 | −10.441 | 1.00 | 33.90 | C |
| ATOM | 1295 | CD | PRO | B | 23 | 6.938 | 47.263 | −10.369 | 1.00 | 31.65 | C |
| ATOM | 1298 | C | PRO | B | 23 | 6.183 | 45.929 | −7.198 | 1.00 | 32.61 | C |
| ATOM | 1299 | O | PRO | B | 23 | 5.551 | 45.166 | −6.476 | 1.00 | 33.52 | O |
| ATOM | 1300 | N | LYS | B | 24 | 7.385 | 46.366 | −6.868 | 1.00 | 34.90 | N |
| ATOM | 1301 | CA | LYS | B | 24 | 8.001 | 45.996 | −5.596 | 1.00 | 35.29 | C |
| ATOM | 1303 | CB | LYS | B | 24 | 8.617 | 44.601 | −5.623 | 1.00 | 36.40 | C |
| ATOM | 1306 | CG | LYS | B | 24 | 9.303 | 44.236 | −4.304 | 1.00 | 34.85 | C |
| ATOM | 1309 | CD | LYS | B | 24 | 9.934 | 42.876 | −4.313 | 1.00 | 38.48 | C |
| ATOM | 1312 | CE | LYS | B | 24 | 10.995 | 42.736 | −5.352 | 1.00 | 45.70 | C |
| ATOM | 1315 | NZ | LYS | B | 24 | 11.716 | 41.466 | −5.110 | 1.00 | 47.84 | N |
| ATOM | 1319 | C | LYS | B | 24 | 9.072 | 47.025 | −5.316 | 1.00 | 32.73 | C |
| ATOM | 1320 | O | LYS | B | 24 | 10.094 | 47.078 | −6.017 | 1.00 | 32.50 | O |
| ATOM | 1322 | N | ILE | B | 25 | 8.832 | 47.837 | −4.290 | 1.00 | 35.25 | N |
| ATOM | 1323 | CA | ILE | B | 25 | 9.666 | 48.965 | −3.964 | 1.00 | 34.84 | C |
| ATOM | 1325 | CB | ILE | B | 25 | 8.873 | 50.100 | −3.306 | 1.00 | 35.14 | C |
| ATOM | 1327 | CG1 | ILE | B | 25 | 7.823 | 50.654 | −4.281 | 1.00 | 35.33 | C |
| ATOM | 1330 | CG2 | ILE | B | 25 | 6.765 | 51.515 | −3.666 | 1.00 | 33.95 | C |
| ATOM | 1334 | CD1 | ILE | B | 25 | 9.806 | 51.244 | −2.887 | 1.00 | 34.59 | C |
| ATOM | 1338 | C | ILE | B | 25 | 10.816 | 48.547 | −3.053 | 1.00 | 35.30 | C |
| ATOM | 1339 | O | ILE | B | 25 | 10.594 | 48.188 | −1.900 | 1.00 | 36.21 | O |

TABLE 2-continued

| | | | | | | | | |
|---|---|---|---|---|---|---|---|---|
| ATOM | 1341 | N | VAL | B | 26 | 12.027 | 48.583 | -3.587 | 1.00 | 34.89 | N |
| ATOM | 1342 | CA | VAL | B | 26 | 13.243 | 48.235 | -2.862 | 1.00 | 35.85 | C |
| ATOM | 1344 | CB | VAL | B | 26 | 13.912 | 46.989 | -3.472 | 1.00 | 35.13 | C |
| ATOM | 1346 | CG1 | VAL | B | 26 | 15.234 | 46.558 | -2.723 | 1.00 | 34.88 | C |
| ATOM | 1350 | CG2 | VAL | B | 26 | 12.938 | 45.833 | -3.503 | 1.00 | 36.34 | C |
| ATOM | 1354 | C | VAL | B | 26 | 14.162 | 49.451 | -2.973 | 1.00 | 36.66 | C |
| ATOM | 1355 | O | VAL | B | 26 | 14.233 | 50.109 | -4.012 | 1.00 | 37.59 | O |
| ATOM | 1357 | N | HIS | B | 27 | 14.827 | 49.780 | -1.872 | 1.00 | 36.69 | N |
| ATOM | 1358 | CA | HIS | B | 27 | 15.879 | 50.811 | -1.892 | 1.00 | 35.48 | C |
| ATOM | 1360 | CB | HIS | B | 27 | 15.566 | 52.013 | -1.001 | 1.00 | 36.12 | C |
| ATOM | 1363 | CG | HIS | B | 27 | 14.493 | 52.877 | -1.544 | 1.00 | 34.60 | C |
| ATOM | 1364 | ND1 | HIS | B | 27 | 13.155 | 52.605 | -1.353 | 1.00 | 35.63 | N |
| ATOM | 1366 | CE1 | HIS | B | 27 | 12.432 | 53.506 | -1.985 | 1.00 | 35.96 | C |
| ATOM | 1368 | NE2 | HIS | B | 27 | 13.260 | 54.356 | -2.570 | 1.00 | 37.44 | N |
| ATOM | 1370 | CD2 | HIS | B | 27 | 14.546 | 53.966 | -2.333 | 1.00 | 36.38 | C |
| ATOM | 1372 | C | HIS | B | 27 | 17.174 | 50.191 | -1.466 | 1.00 | 34.61 | C |
| ATOM | 1373 | O | HIS | B | 27 | 17.215 | 49.384 | -0.527 | 1.00 | 35.73 | O |
| ATOM | 1375 | N | ALA | B | 28 | 18.222 | 50.532 | -2.176 | 1.00 | 32.21 | N |
| ATOM | 1376 | CA | ALA | B | 28 | 19.546 | 50.057 | -1.826 | 1.00 | 32.06 | C |
| ATOM | 1378 | CB | ALA | B | 28 | 19.970 | 48.896 | -2.711 | 1.00 | 34.42 | C |
| ATOM | 1382 | C | ALA | B | 28 | 20.576 | 51.147 | -1.839 | 1.00 | 34.27 | C |
| ATOM | 1383 | O | ALA | B | 28 | 20.795 | 51.813 | -2.853 | 1.00 | 36.56 | O |
| ATOM | 1385 | N | PHE | B | 29 | 21.224 | 51.309 | -0.695 | 1.00 | 32.52 | N |
| ATOM | 1386 | CA | PHE | B | 29 | 22.215 | 52.354 | -0.485 | 1.00 | 33.78 | C |
| ATOM | 1388 | CB | PHE | B | 29 | 21.734 | 53.313 | 0.606 | 1.00 | 35.40 | C |
| ATOM | 1391 | CG | PHE | B | 29 | 20.491 | 54.049 | 0.264 | 1.00 | 35.76 | C |
| ATOM | 1392 | CD1 | PHE | B | 29 | 20.539 | 55.120 | -0.613 | 1.00 | 30.53 | C |
| ATOM | 1394 | CE1 | PHE | B | 29 | 19.374 | 55.821 | -0.921 | 1.00 | 34.08 | C |
| ATOM | 1396 | CZ | PHE | B | 29 | 18.156 | 55.455 | -0.355 | 1.00 | 35.02 | C |
| ATOM | 1398 | CE2 | PHE | B | 29 | 18.095 | 54.394 | 0.541 | 1.00 | 36.03 | C |
| ATOM | 1400 | CD2 | PHE | B | 29 | 19.267 | 53.702 | 0.841 | 1.00 | 35.11 | C |
| ATOM | 1402 | C | PHE | B | 29 | 23.557 | 51.797 | -0.064 | 1.00 | 33.67 | C |
| ATOM | 1403 | O | PHE | B | 29 | 23.642 | 50.865 | 0.736 | 1.00 | 32.36 | O |
| ATOM | 1405 | N | ASP | B | 30 | 24.606 | 52.410 | -0.608 | 1.00 | 34.81 | N |
| ATOM | 1406 | CA | ASP | B | 30 | 26.002 | 52.142 | -0.246 | 1.00 | 35.60 | C |
| ATOM | 1408 | CB | ASP | B | 30 | 26.945 | 52.528 | -1.376 | 1.00 | 37.16 | C |
| ATOM | 1411 | CG | ASP | B | 30 | 26.771 | 51.661 | -2.601 | 1.00 | 40.67 | C |
| ATOM | 1412 | OD1 | ASP | B | 30 | 26.230 | 50.549 | -2.466 | 1.00 | 38.68 | O |
| ATOM | 1413 | OD2 | ASP | B | 30 | 27.189 | 52.085 | -3.701 | 1.00 | 39.29 | O |
| ATOM | 1414 | C | ASP | B | 30 | 26.352 | 52.944 | 0.997 | 1.00 | 36.65 | C |
| ATOM | 1415 | O | ASP | B | 30 | 26.123 | 54.147 | 1.032 | 1.00 | 34.21 | O |
| ATOM | 1417 | N | MET | B | 31 | 26.903 | 52.279 | 2.016 | 1.00 | 37.98 | N |
| ATOM | 1418 | CA | MET | B | 31 | 27.125 | 52.925 | 3.322 | 1.00 | 40.37 | C |
| ATOM | 1420 | CB | MET | B | 31 | 27.437 | 51.905 | 4.433 | 1.00 | 41.23 | C |
| ATOM | 1423 | CG | MET | B | 31 | 28.497 | 50.879 | 4.115 | 1.00 | 43.08 | C |
| ATOM | 1426 | SD | MET | B | 31 | 28.671 | 49.578 | 5.372 | 1.00 | 43.79 | S |
| ATOM | 1427 | CE | MET | B | 31 | 27.222 | 48.587 | 5.083 | 1.00 | 38.58 | C |
| ATOM | 1431 | C | MET | B | 31 | 28.187 | 54.012 | 3.243 | 1.00 | 40.37 | C |
| ATOM | 1432 | O | MET | B | 31 | 28.168 | 54.943 | 4.041 | 1.00 | 40.03 | O |
| ATOM | 1434 | N | GLU | B | 32 | 29.065 | 53.921 | 2.249 | 1.00 | 40.74 | N |
| ATOM | 1435 | CA | GLU | B | 32 | 30.061 | 54.956 | 1.994 | 1.00 | 42.65 | C |
| ATOM | 1437 | CB | GLU | B | 32 | 31.124 | 54.463 | 1.004 | 1.00 | 42.74 | C |
| ATOM | 1440 | CG | GLU | B | 32 | 31.923 | 53.240 | 1.481 | 1.00 | 46.15 | C |

TABLE 2-continued

| ATOM | 1443 | CD | GLU | B | 32 | 31.259 | 51.904 | 1.148 | 1.00 | 47.27 | C |
|------|------|-----|-----|---|----|--------|--------|--------|------|-------|---|
| ATOM | 1444 | OE1 | GLU | B | 32 | 30.074 | 51.897 | 0.762 | 1.00 | 40.21 | O |
| ATOM | 1445 | OE2 | GLU | B | 32 | 31.939 | 50.859 | 1.270 | 1.00 | 48.39 | O |
| ATOM | 1446 | C | GLU | B | 32 | 29.430 | 56.245 | 1.453 | 1.00 | 43.29 | C |
| ATOM | 1447 | O | GLU | B | 32 | 30.046 | 57.307 | 1.534 | 1.00 | 44.23 | O |
| ATOM | 1449 | N | ASP | B | 33 | 28.230 | 56.145 | 0.882 | 1.00 | 43.76 | N |
| ATOM | 1450 | CA | ASP | B | 33 | 27.483 | 57.310 | 0.419 | 1.00 | 43.37 | C |
| ATOM | 1452 | CB | ASP | B | 33 | 26.542 | 56.932 | −0.730 | 1.00 | 43.70 | C |
| ATOM | 1455 | CG | ASP | B | 33 | 27.272 | 56.473 | −1.986 | 1.00 | 42.35 | C |
| ATOM | 1456 | OD1 | ASP | B | 33 | 28.502 | 56.693 | −2.115 | 1.00 | 38.96 | O |
| ATOM | 1457 | OD2 | ASP | B | 33 | 26.580 | 55.905 | −2.874 | 1.00 | 38.76 | O |
| ATOM | 1458 | C | ASP | B | 33 | 26.644 | 57.929 | 1.536 | 1.00 | 43.76 | C |
| ATOM | 1459 | O | ASP | B | 33 | 25.996 | 58.947 | 1.314 | 1.00 | 44.17 | O |
| ATOM | 1461 | N | LEU | B | 34 | 26.624 | 57.313 | 2.720 | 1.00 | 43.54 | N |
| ATOM | 1462 | CA | LEU | B | 34 | 25.796 | 57.814 | 3.823 | 1.00 | 44.47 | C |
| ATOM | 1464 | CB | LEU | B | 34 | 25.304 | 56.679 | 4.742 | 1.00 | 44.00 | C |
| ATOM | 1467 | CG | LEU | B | 34 | 24.464 | 55.548 | 4.138 | 1.00 | 44.19 | C |
| ATOM | 1469 | CD1 | LEU | B | 34 | 23.872 | 54.649 | 5.222 | 1.00 | 44.88 | C |
| ATOM | 1473 | CD2 | LEU | B | 34 | 23.358 | 56.087 | 3.266 | 1.00 | 43.23 | C |
| ATOM | 1477 | C | LEU | B | 34 | 26.592 | 58.823 | 4.622 | 1.00 | 44.84 | C |
| ATOM | 1478 | O | LEU | B | 34 | 27.819 | 58.763 | 4.669 | 1.00 | 45.66 | O |
| ATOM | 1480 | N | GLY | B | 35 | 25.898 | 59.762 | 5.244 | 1.00 | 45.47 | N |
| ATOM | 1481 | CA | GLY | B | 35 | 26.562 | 60.737 | 6.091 | 1.00 | 46.52 | C |
| ATOM | 1484 | C | GLY | B | 35 | 26.904 | 60.132 | 7.439 | 1.00 | 46.86 | C |
| ATOM | 1485 | O | GLY | B | 35 | 27.306 | 58.965 | 7.530 | 1.00 | 48.05 | O |
| ATOM | 1487 | N | ASP | B | 36 | 26.744 | 60.934 | 8.487 | 1.00 | 45.64 | N |
| ATOM | 1488 | CA | ASP | B | 36 | 26.851 | 60.438 | 9.852 | 1.00 | 44.85 | C |
| ATOM | 1490 | CB | ASP | B | 36 | 26.924 | 61.609 | 10.831 | 1.00 | 44.93 | C |
| ATOM | 1496 | C | ASP | B | 36 | 25.621 | 59.570 | 10.205 | 1.00 | 44.24 | C |
| ATOM | 1497 | O | ASP | B | 36 | 25.751 | 58.582 | 10.923 | 1.00 | 43.59 | O |
| ATOM | 1499 | N | LYS | B | 37 | 24.448 | 59.952 | 9.703 | 1.00 | 43.10 | N |
| ATOM | 1500 | CA | LYS | B | 37 | 23.197 | 59.357 | 10.135 | 1.00 | 43.59 | C |
| ATOM | 1502 | CB | LYS | B | 37 | 22.686 | 60.101 | 11.371 | 1.00 | 43.52 | C |
| ATOM | 1505 | CG | LYS | B | 37 | 21.408 | 59.550 | 11.964 | 1.00 | 46.25 | C |
| ATOM | 1508 | CD | LYS | B | 37 | 21.130 | 60.169 | 13.330 | 1.00 | 46.05 | C |
| ATOM | 1511 | CE | LYS | B | 37 | 19.709 | 59.887 | 13.798 | 1.00 | 49.27 | C |
| ATOM | 1514 | NZ | LYS | B | 37 | 19.518 | 60.183 | 15.252 | 1.00 | 53.79 | N |
| ATOM | 1518 | C | LYS | B | 37 | 22.133 | 59.393 | 9.034 | 1.00 | 42.72 | C |
| ATOM | 1519 | O | LYS | B | 37 | 21.936 | 60.418 | 8.373 | 1.00 | 43.44 | O |
| ATOM | 1521 | N | ALA | B | 38 | 21.458 | 58.261 | 8.843 | 1.00 | 40.52 | N |
| ATOM | 1522 | CA | ALA | B | 38 | 20.286 | 58.182 | 7.992 | 1.00 | 39.21 | C |
| ATOM | 1524 | CB | ALA | B | 38 | 20.609 | 57.436 | 6.716 | 1.00 | 39.73 | C |
| ATOM | 1528 | C | ALA | B | 38 | 19.152 | 57.487 | 8.750 | 1.00 | 38.11 | C |
| ATOM | 1529 | O | ALA | B | 38 | 19.351 | 56.496 | 9.450 | 1.00 | 36.88 | O |
| ATOM | 1531 | N | VAL | B | 39 | 17.959 | 58.040 | 8.614 | 1.00 | 38.66 | N |
| ATOM | 1532 | CA | VAL | B | 39 | 16.791 | 57.533 | 9.298 | 1.00 | 38.82 | C |
| ATOM | 1534 | CB | VAL | B | 39 | 16.235 | 58.547 | 10.320 | 1.00 | 36.19 | C |
| ATOM | 1536 | CG1 | VAL | B | 39 | 15.163 | 57.897 | 11.197 | 1.00 | 39.39 | C |
| ATOM | 1540 | CG2 | VAL | B | 39 | 17.370 | 59.096 | 11.175 | 1.00 | 37.65 | C |
| ATOM | 1544 | C | VAL | B | 39 | 15.760 | 57.163 | 8.231 | 1.00 | 38.44 | C |
| ATOM | 1545 | O | VAL | B | 39 | 15.238 | 58.029 | 7.502 | 1.00 | 37.67 | O |
| ATOM | 1547 | N | TYR | B | 40 | 15.489 | 55.863 | 8.148 | 1.00 | 38.33 | N |
| ATOM | 1548 | CA | TYR | B | 40 | 14.615 | 55.305 | 7.109 | 1.00 | 37.47 | C |

TABLE 2-continued

| | | | | | | | | |
|---|---|---|---|---|---|---|---|---|
| ATOM | 1550 | CB | TYR | B | 40 | 15.282 | 54.081 | 6.477 | 1.00 | 37.06 | C |
| ATOM | 1553 | CG | TYR | B | 40 | 16.629 | 54.365 | 5.869 | 1.00 | 34.91 | C |
| ATOM | 1554 | CD1 | TYR | B | 40 | 16.745 | 55.002 | 4.630 | 1.00 | 32.80 | C |
| ATOM | 1556 | CE1 | TYR | B | 40 | 17.987 | 55.242 | 4.076 | 1.00 | 34.13 | C |
| ATOM | 1558 | CZ | TYR | B | 40 | 19.115 | 54.866 | 4.757 | 1.00 | 36.42 | C |
| ATOM | 1559 | OH | TYR | B | 40 | 20.353 | 55.132 | 4.229 | 1.00 | 37.60 | O |
| ATOM | 1561 | CE2 | TYR | B | 40 | 19.019 | 54.234 | 5.987 | 1.00 | 34.73 | C |
| ATOM | 1563 | CD2 | TYR | B | 40 | 17.788 | 54.004 | 6.532 | 1.00 | 34.64 | C |
| ATOM | 1565 | C | TYR | B | 40 | 13.206 | 54.990 | 7.615 | 1.00 | 37.63 | C |
| ATOM | 1566 | O | TYR | B | 40 | 13.033 | 54.386 | 8.694 | 1.00 | 39.88 | O |
| ATOM | 1568 | N | CYS | B | 41 | 12.239 | 55.329 | 6.780 | 1.00 | 35.98 | N |
| ATOM | 1569 | CA | CYS | B | 41 | 10.841 | 55.079 | 7.044 | 1.00 | 34.37 | C |
| ATOM | 1571 | CB | CYS | B | 41 | 10.003 | 55.929 | 6.099 | 1.00 | 32.42 | C |
| ATOM | 1574 | SG | CYS | B | 41 | 8.229 | 55.697 | 6.255 | 1.00 | 33.48 | S |
| ATOM | 1576 | C | CYS | B | 41 | 10.472 | 53.610 | 6.902 | 1.00 | 33.69 | C |
| ATOM | 1577 | O | CYS | B | 41 | 10.738 | 52.965 | 5.900 | 1.00 | 35.88 | O |
| ATOM | 1579 | N | ARG | B | 42 | 9.685 | 53.108 | 7.836 | 1.00 | 28.53 | N |
| ATOM | 1580 | CA | ARG | B | 42 | 9.229 | 51.688 | 7.758 | 1.00 | 33.08 | C |
| ATOM | 1582 | CB | ARG | B | 42 | 9.826 | 50.873 | 8.900 | 1.00 | 34.77 | C |
| ATOM | 1585 | CG | ARG | B | 42 | 11.350 | 50.607 | 8.763 | 1.00 | 28.18 | C |
| ATOM | 1588 | CD | ARG | B | 42 | 12.009 | 49.630 | 9.642 | 1.00 | 28.49 | C |
| ATOM | 1591 | NE | ARG | B | 42 | 11.823 | 49.920 | 11.096 | 1.00 | 28.16 | N |
| ATOM | 1593 | CZ | ARG | B | 42 | 12.390 | 49.170 | 12.075 | 1.00 | 30.05 | C |
| ATOM | 1594 | NH1 | ARG | B | 42 | 13.219 | 48.146 | 11.881 | 1.00 | 37.13 | N |
| ATOM | 1597 | NH2 | ARG | B | 42 | 12.129 | 49.508 | 13.325 | 1.00 | 35.19 | N |
| ATOM | 1600 | C | ARG | B | 42 | 7.725 | 51.648 | 7.805 | 1.00 | 31.97 | C |
| ATOM | 1601 | O | ARG | B | 42 | 7.139 | 50.602 | 7.941 | 1.00 | 38.77 | O |
| ATOM | 1603 | N | CYS | B | 43 | 7.098 | 52.840 | 7.762 | 1.00 | 31.12 | N |
| ATOM | 1604 | CA | CYS | B | 43 | 5.635 | 52.989 | 7.838 | 1.00 | 35.22 | C |
| ATOM | 1606 | CB | CYS | B | 43 | 5.194 | 54.056 | 8.885 | 1.00 | 35.22 | C |
| ATOM | 1609 | SG | CYS | B | 43 | 5.466 | 55.787 | 8.452 | 1.00 | 34.25 | S |
| ATOM | 1611 | C | CYS | B | 43 | 5.003 | 53.322 | 6.514 | 1.00 | 36.45 | C |
| ATOM | 1612 | O | CYS | B | 43 | 3.805 | 53.328 | 6.415 | 1.00 | 33.64 | O |
| ATOM | 1614 | N | TRP | B | 44 | 5.770 | 53.673 | 5.503 | 1.00 | 36.75 | N |
| ATOM | 1615 | CA | TRP | B | 44 | 5.195 | 54.095 | 4.209 | 1.00 | 36.62 | C |
| ATOM | 1617 | CB | TRP | B | 44 | 4.558 | 52.865 | 3.539 | 1.00 | 33.41 | C |
| ATOM | 1620 | CG | TRP | B | 44 | 5.548 | 51.735 | 3.407 | 1.00 | 33.38 | C |
| ATOM | 1621 | CD1 | TRP | B | 44 | 5.877 | 50.867 | 4.363 | 1.00 | 33.75 | C |
| ATOM | 1623 | NE1 | TRP | B | 44 | 6.800 | 49.979 | 3.894 | 1.00 | 33.92 | N |
| ATOM | 1625 | CE2 | TRP | B | 44 | 7.112 | 50.288 | 2.605 | 1.00 | 40.09 | C |
| ATOM | 1626 | CD2 | TRP | B | 44 | 6.347 | 51.403 | 2.259 | 1.00 | 36.94 | C |
| ATOM | 1627 | CE3 | TRP | B | 44 | 6.460 | 51.937 | 0.963 | 1.00 | 37.27 | C |
| ATOM | 1629 | CZ3 | TRP | B | 44 | 7.337 | 51.342 | 0.080 | 1.00 | 34.56 | C |
| ATOM | 1631 | CH2 | TRP | B | 44 | 8.104 | 50.226 | 0.456 | 1.00 | 37.23 | C |
| ATOM | 1633 | CZ2 | TRP | B | 44 | 8.022 | 49.694 | 1.723 | 1.00 | 34.62 | C |
| ATOM | 1635 | C | TRP | B | 44 | 4.250 | 55.298 | 4.206 | 1.00 | 35.53 | C |
| ATOM | 1636 | O | TRP | B | 44 | 3.379 | 55.441 | 3.320 | 1.00 | 39.48 | O |
| ATOM | 1638 | N | ARG | B | 45 | 4.440 | 56.206 | 5.177 | 1.00 | 33.30 | N |
| ATOM | 1639 | CA | ARG | B | 45 | 3.624 | 57.373 | 5.330 | 1.00 | 29.58 | C |
| ATOM | 1641 | CB | ARG | B | 45 | 2.939 | 57.420 | 6.712 | 1.00 | 31.23 | C |
| ATOM | 1644 | CG | ARG | B | 45 | 1.960 | 56.272 | 6.965 | 1.00 | 37.34 | C |

TABLE 2-continued

| | | | | | | | | |
|---|---|---|---|---|---|---|---|---|
| ATOM | 1647 | CD | ARG | B | 45 | 0.932 | 56.181 | 5.915 | 1.00 | 40.57 | C |
| ATOM | 1650 | NE | ARG | B | 45 | -0.037 | 55.117 | 6.169 | 1.00 | 46.51 | N |
| ATOM | 1652 | CZ | ARG | B | 45 | 0.036 | 53.913 | 5.617 | 1.00 | 44.58 | C |
| ATOM | 1653 | NH1 | ARG | B | 45 | 1.003 | 53.637 | 4.762 | 1.00 | 41.26 | N |
| ATOM | 1656 | NH2 | ARG | B | 45 | -0.884 | 53.004 | 5.897 | 1.00 | 45.33 | N |
| ATOM | 1659 | C | ARG | B | 45 | 4.411 | 58.658 | 5.139 | 1.00 | 27.55 | C |
| ATOM | 1660 | O | ARG | B | 45 | 3.798 | 59.716 | 4.906 | 1.00 | 34.06 | O |
| ATOM | 1662 | N | SER | B | 46 | 5.755 | 58.514 | 5.180 | 1.00 | 36.48 | N |
| ATOM | 1663 | CA | SER | B | 46 | 6.645 | 59.656 | 4.968 | 1.00 | 35.94 | C |
| ATOM | 1665 | CB | SER | B | 46 | 8.110 | 59.166 | 5.054 | 1.00 | 35.65 | C |
| ATOM | 1668 | OG | SER | B | 46 | 8.954 | 60.322 | 4.916 | 1.00 | 37.02 | O |
| ATOM | 1670 | C | SER | B | 46 | 6.380 | 60.354 | 3.624 | 1.00 | 38.64 | C |
| ATOM | 1671 | O | SER | B | 46 | 6.127 | 59.693 | 2.604 | 1.00 | 39.66 | O |
| ATOM | 1673 | N | LYS | B | 47 | 6.462 | 61.681 | 3.632 | 1.00 | 39.65 | N |
| ATOM | 1674 | CA | LYS | B | 47 | 6.448 | 62.454 | 2.405 | 1.00 | 41.32 | C |
| ATOM | 1676 | CB | LYS | B | 47 | 5.849 | 63.828 | 2.658 | 1.00 | 43.74 | C |
| ATOM | 1679 | CG | LYS | B | 47 | 4.397 | 63.793 | 3.118 | 1.00 | 47.46 | C |
| ATOM | 1682 | CD | LYS | B | 47 | 3.521 | 63.010 | 2.154 | 1.00 | 52.78 | C |
| ATOM | 1685 | CE | LYS | B | 47 | 2.050 | 63.363 | 2.331 | 1.00 | 52.93 | C |
| ATOM | 1688 | NZ | LYS | B | 47 | 1.179 | 62.586 | 1.396 | 1.00 | 55.84 | N |
| ATOM | 1692 | C | LYS | B | 47 | 7.849 | 62.585 | 1.827 | 1.00 | 41.49 | C |
| ATOM | 1693 | O | LYS | B | 47 | 8.028 | 63.158 | 0.759 | 1.00 | 41.94 | O |
| ATOM | 1695 | N | LYS | B | 48 | 8.834 | 62.057 | 2.541 | 1.00 | 42.18 | N |
| ATOM | 1696 | CA | LYS | B | 48 | 10.224 | 62.036 | 2.097 | 1.00 | 42.24 | C |
| ATOM | 1698 | CB | LYS | B | 4B | 11.098 | 62.781 | 3.125 | 1.00 | 43.58 | C |
| ATOM | 1701 | CG | LYS | B | 48 | 10.636 | 64.202 | 3.453 | 1.00 | 46.22 | C |
| ATOM | 1704 | CD | LYS | B | 48 | 10.757 | 65.148 | 2.267 | 1.00 | 50.87 | C |
| ATOM | 1707 | CE | LYS | B | 48 | 10.119 | 66.519 | 2.550 | 1.00 | 52.45 | C |
| ATOM | 1710 | NZ | LYS | B | 48 | 8.610 | 66.539 | 2.448 | 1.00 | 54.46 | N |
| ATOM | 1714 | C | LYS | B | 48 | 10.718 | 60.589 | 1.921 | 1.00 | 40.08 | C |
| ATOM | 1715 | O | LYS | B | 48 | 11.909 | 60.318 | 1.960 | 1.00 | 38.81 | O |
| ATOM | 1717 | N | PHE | B | 49 | 9.789 | 59.663 | 1.689 | 1.00 | 39.78 | N |
| ATOM | 1718 | CA | PHE | B | 49 | 10.119 | 58.265 | 1.553 | 1.00 | 40.08 | C |
| ATOM | 1720 | CB | PHE | B | 49 | 8.881 | 57.441 | 1.178 | 1.00 | 40.50 | C |
| ATOM | 1723 | CG | PHE | B | 49 | 9.066 | 55.983 | 1.404 | 1.00 | 38.27 | C |
| ATOM | 1724 | CD1 | PHE | B | 49 | 9.537 | 55.145 | 0.388 | 1.00 | 40.52 | C |
| ATOM | 1726 | CE1 | PHE | B | 49 | 9.739 | 53.799 | 0.620 | 1.00 | 38.39 | C |
| ATOM | 1728 | CZ | PHE | B | 49 | 9.489 | 53.260 | 1.889 | 1.00 | 38.45 | C |
| ATOM | 1730 | CE2 | PHE | B | 49 | 9.027 | 54.076 | 2.898 | 1.00 | 37.17 | C |
| ATOM | 1732 | CD2 | PHE | B | 49 | 8.817 | 55.428 | 2.660 | 1.00 | 35.48 | C |
| ATOM | 1734 | C | PHE | B | 49 | 11.222 | 58.084 | 0.512 | 1.00 | 40.32 | C |
| ATOM | 1735 | O | PHE | B | 49 | 11.156 | 58.684 | -0.554 | 1.00 | 39.97 | O |
| ATOM | 1737 | N | PRO | B | 50 | 12.238 | 57.246 | 0.802 | 1.00 | 38.37 | N |
| ATOM | 1738 | CA | PRO | B | 50 | 12.463 | 56.226 | 1.851 | 1.00 | 38.85 | C |
| ATOM | 1740 | CB | PRO | B | 50 | 13.575 | 55.375 | 1.241 | 1.00 | 39.25 | C |
| ATOM | 1743 | CG | PRO | B | 50 | 14.378 | 56.362 | 0.443 | 1.00 | 39.24 | C |
| ATOM | 1746 | CD | PRO | B | 50 | 13.407 | 57.367 | -0.091 | 1.00 | 39.75 | C |
| ATOM | 1749 | C | PRO | B | 50 | 12.890 | 56.773 | 3.227 | 1.00 | 36.68 | C |
| ATOM | 1750 | O | PRO | B | 50 | 13.173 | 56.020 | 4.139 | 1.00 | 36.76 | O |
| ATOM | 1751 | N | PHE | B | 51 | 12.955 | 58.081 | 3.376 | 1.00 | 36.46 | N |

TABLE 2-continued

| ATOM | 1752 | CA | PHE | B | 51 | 13.406 | 58.660 | 4.631 | 1.00 | 38.63 | C |
|------|------|----|-----|---|----|--------|--------|-------|------|-------|---|
| ATOM | 1754 | CB | PHE | B | 51 | 14.270 | 59.883 | 4.362 | 1.00 | 40.19 | C |
| ATOM | 1757 | CG | PHE | B | 51 | 15.401 | 59.589 | 3.459 | 1.00 | 40.22 | C |
| ATOM | 1758 | CD1 | PHE | B | 51 | 16.485 | 58.872 | 3.925 | 1.00 | 41.70 | C |
| ATOM | 1760 | CE1 | PHE | B | 51 | 17.530 | 58.555 | 3.084 | 1.00 | 45.00 | C |
| ATOM | 1762 | CZ | PHE | B | 51 | 17.480 | 58.945 | 1.760 | 1.00 | 42.05 | C |
| ATOM | 1764 | CE2 | PHE | B | 51 | 16.395 | 59.652 | 1.283 | 1.00 | 47.03 | C |
| ATOM | 1766 | CD2 | PHE | B | 51 | 15.356 | 59.965 | 2.126 | 1.00 | 42.56 | C |
| ATOM | 1768 | C | PHE | B | 51 | 12.235 | 58.961 | 5.559 | 1.00 | 37.33 | C |
| ATOM | 1769 | O | PHE | B | 51 | 11.118 | 59.308 | 5.123 | 1.00 | 37.13 | O |
| ATOM | 1771 | N | CYS | B | 52 | 12.508 | 58.789 | 6.848 | 1.00 | 36.88 | N |
| ATOM | 1772 | CA | CYS | B | 52 | 11.540 | 59.086 | 7.900 | 1.00 | 37.47 | C |
| ATOM | 1774 | CB | CYS | B | 52 | 11.989 | 58.431 | 9.216 | 1.00 | 38.68 | C |
| ATOM | 1777 | SG | CYS | B | 52 | 10.906 | 58.770 | 10.646 | 1.00 | 36.37 | S |
| ATOM | 1779 | C | CYS | B | 52 | 11.362 | 60.589 | 8.073 | 1.00 | 38.92 | C |
| ATOM | 1780 | O | CYS | B | 52 | 12.326 | 61.319 | 8.272 | 1.00 | 39.29 | O |
| ATOM | 1782 | N | ASP | B | 53 | 10.128 | 61.067 | 8.025 | 1.00 | 37.37 | N |
| ATOM | 1783 | CA | ASP | B | 53 | 9.838 | 62.459 | 8.274 | 1.00 | 37.77 | C |
| ATOM | 1785 | CB | ASP | B | 53 | 9.153 | 63.106 | 7.053 | 1.00 | 36.84 | C |
| ATOM | 1788 | CG | ASP | B | 53 | 7.732 | 62.621 | 6.840 | 1.00 | 33.27 | C |
| ATOM | 1789 | OD1 | ASP | B | 53 | 7.369 | 61.603 | 7.507 | 1.00 | 36.46 | O |
| ATOM | 1790 | OD2 | ASP | B | 53 | 7.048 | 63.132 | 5.943 | 1.00 | 42.47 | O |
| ATOM | 1791 | C | ASP | B | 53 | 8.980 | 62.631 | 9.541 | 1.00 | 38.39 | C |
| ATOM | 1792 | O | ASP | B | 53 | 8.454 | 63.710 | 9.763 | 1.00 | 39.91 | O |
| ATOM | 1794 | N | GLY | B | 54 | 8.837 | 61.584 | 10.361 | 1.00 | 38.91 | N |
| ATOM | 1795 | CA | GLY | B | 54 | 8.001 | 61.677 | 11.558 | 1.00 | 38.45 | C |
| ATOM | 1798 | C | GLY | B | 54 | 6.525 | 61.327 | 11.362 | 1.00 | 39.75 | C |
| ATOM | 1799 | O | GLY | B | 54 | 5.767 | 61.301 | 12.328 | 1.00 | 38.81 | O |
| ATOM | 1801 | N | ALA | B | 55 | 6.127 | 60.998 | 10.128 | 1.00 | 39.22 | N |
| ATOM | 1802 | CA | ALA | B | 55 | 4.745 | 60.592 | 9.824 | 1.00 | 37.57 | C |
| ATOM | 1804 | CB | ALA | B | 55 | 4.594 | 60.370 | 8.341 | 1.00 | 38.28 | C |
| ATOM | 1808 | C | ALA | B | 55 | 4.243 | 59.350 | 10.599 | 1.00 | 37.96 | C |
| ATOM | 1809 | O | ALA | B | 55 | 3.038 | 59.215 | 10.833 | 1.00 | 37.56 | O |
| ATOM | 1811 | N | HIS | B | 56 | 5.156 | 58.497 | 11.028 | 1.00 | 38.74 | N |
| ATOM | 1812 | CA | HIS | B | 56 | 4.811 | 57.340 | 11.841 | 1.00 | 36.32 | C |
| ATOM | 1814 | CB | HIS | B | 56 | 6.057 | 56.507 | 12.153 | 1.00 | 35.39 | C |
| ATOM | 1817 | CG | HIS | B | 56 | 7.090 | 57.229 | 12.951 | 1.00 | 33.28 | C |
| ATOM | 1818 | ND1 | HIS | B | 56 | 8.214 | 57.774 | 12.378 | 1.00 | 34.78 | N |
| ATOM | 1820 | CE1 | HIS | B | 56 | 8.942 | 58.359 | 13.313 | 1.00 | 37.81 | C |
| ATOM | 1822 | NE2 | HIS | B | 56 | 8.322 | 58.220 | 14.470 | 1.00 | 33.49 | N |
| ATOM | 1824 | CD2 | HIS | B | 56 | 7.157 | 57.522 | 14.269 | 1.00 | 34.01 | C |
| ATOM | 1826 | C | HIS | B | 56 | 4.048 | 57.715 | 13.115 | 1.00 | 37.15 | C |
| ATOM | 1827 | O | HIS | B | 56 | 3.233 | 56.946 | 13.574 | 1.00 | 35.02 | O |
| ATOM | 1829 | N | THR | B | 57 | 4.301 | 58.886 | 13.672 | 1.00 | 38.82 | N |
| ATOM | 1830 | CA | THR | B | 57 | 3.648 | 59.275 | 14.918 | 1.00 | 37.85 | C |
| ATOM | 1832 | CB | THR | B | 57 | 4.245 | 60.577 | 15.458 | 1.00 | 39.12 | C |
| ATOM | 1834 | OG1 | THR | B | 57 | 5.648 | 60.389 | 15.640 | 1.00 | 37.76 | O |
| ATOM | 1836 | CG2 | THR | B | 57 | 3.617 | 60.960 | 16.771 | 1.00 | 38.84 | C |
| ATOM | 1840 | C | THR | B | 57 | 2.137 | 59.399 | 14.731 | 1.00 | 37.46 | C |
| ATOM | 1841 | O | THR | B | 57 | 1.359 | 58.834 | 15.497 | 1.00 | 35.96 | O |

TABLE 2-continued

| | | | | | | | | | |
|---|---|---|---|---|---|---|---|---|---|
| ATOM | 1843 | N | LYS | B | 58 | 1.738 | 60.142 | 13.704 | 1.00 | 36.08 | N |
| ATOM | 1844 | CA | LYS | B | 58 | 0.345 | 60.225 | 13.312 | 1.00 | 35.51 | C |
| ATOM | 1846 | CB | LYS | B | 58 | 0.168 | 61.149 | 12.097 | 1.00 | 35.38 | C |
| ATOM | 1849 | CG | LYS | B | 58 | −1.285 | 61.323 | 11.671 | 1.00 | 34.20 | C |
| ATOM | 1852 | CD | LYS | B | 58 | −1.437 | 62.428 | 10.639 | 1.00 | 37.92 | C |
| ATOM | 1855 | CE | LYS | B | 58 | −2.874 | 62.630 | 10.189 | 1.00 | 44.63 | C |
| ATOM | 1858 | NZ | LYS | B | 58 | −3.375 | 61.576 | 9.253 | 1.00 | 52.20 | N |
| ATOM | 1862 | C | LYS | B | 58 | −0.290 | 58.866 | 13.022 | 1.00 | 35.76 | C |
| ATOM | 1863 | O | LYS | B | 58 | −1.431 | 58.630 | 13.459 | 1.00 | 36.13 | O |
| ATOM | 1865 | N | HIS | B | 58 | 0.411 | 58.033 | 12.255 | 1.00 | 35.17 | N |
| ATOM | 1866 | CA | HIS | B | 58 | −0.039 | 56.669 | 11.910 | 1.00 | 34.03 | C |
| ATOM | 1868 | CB | HIS | B | 59 | 0.997 | 55.920 | 11.070 | 1.00 | 35.79 | C |
| ATOM | 1871 | CG | HIS | B | 59 | 0.714 | 54.454 | 10.972 | 1.00 | 35.58 | C |
| ATOM | 1872 | ND1 | HIS | B | 59 | −0.328 | 53.948 | 10.222 | 1.00 | 40.93 | N |
| ATOM | 1874 | CE1 | HIS | B | 59 | −0.371 | 52.635 | 10.365 | 1.00 | 40.10 | C |
| ATOM | 1876 | NE2 | HIS | B | 59 | 0.581 | 52.277 | 11.208 | 1.00 | 37.12 | N |
| ATOM | 1878 | CD2 | HIS | B | 59 | 1.252 | 53.403 | 11.625 | 1.00 | 35.54 | C |
| ATOM | 1880 | C | HIS | B | 59 | −0.359 | 55.849 | 13.173 | 1.00 | 35.85 | C |
| ATOM | 1881 | O | HIS | B | 59 | −1.427 | 55.231 | 13.292 | 1.00 | 35.46 | O |
| ATOM | 1883 | N | ASN | B | 59 | 0.565 | 55.866 | 14.120 | 1.00 | 34.82 | N |
| ATOM | 1884 | CA | ASN | B | 60 | 0.438 | 55.058 | 15.336 | 1.00 | 36.34 | C |
| ATOM | 1886 | CB | ASN | B | 60 | 1.730 | 55.084 | 16.169 | 1.00 | 37.42 | C |
| ATOM | 1889 | CG | ASN | B | 60 | 2.848 | 54.298 | 15.565 | 1.00 | 36.94 | C |
| ATOM | 1890 | OD1 | ASN | B | 60 | 2.642 | 53.418 | 14.720 | 1.00 | 33.80 | O |
| ATOM | 1891 | ND2 | ASN | B | 60 | 4.072 | 54.599 | 16.004 | 1.00 | 34.62 | N |
| ATOM | 1894 | C | ASN | B | 60 | −0.698 | 55.552 | 16.184 | 1.00 | 36.42 | C |
| ATOM | 1895 | O | ASN | B | 60 | −1.456 | 54.757 | 16.737 | 1.00 | 36.42 | O |
| ATOM | 1897 | N | GLU | B | 60 | −0.803 | 56.872 | 16.291 | 1.00 | 37.35 | N |
| ATOM | 1898 | CA | GLU | B | 61 | −1.906 | 57.511 | 17.001 | 1.00 | 37.97 | C |
| ATOM | 1900 | CB | GLU | B | 61 | −1.702 | 59.040 | 17.006 | 1.00 | 38.07 | C |
| ATOM | 1903 | CG | GLU | B | 61 | −2.728 | 59.847 | 17.770 | 1.00 | 43.25 | C |
| ATOM | 1906 | CD | GLU | B | 61 | −2.798 | 59.499 | 19.251 | 1.00 | 47.22 | C |
| ATOM | 1907 | OE1 | GLU | B | 61 | −1.769 | 59.112 | 19.841 | 1.00 | 46.08 | O |
| ATOM | 1908 | OE2 | GLU | B | 61 | −3.891 | 59.625 | 19.831 | 1.00 | 51.54 | O |
| ATOM | 1909 | C | GLU | B | 61 | −3.275 | 57.140 | 16.415 | 1.00 | 39.16 | C |
| ATOM | 1910 | O | GLU | B | 61 | −4.193 | 56.792 | 17.156 | 1.00 | 40.06 | O |
| ATOM | 1912 | N | GLU | B | 62 | −3.398 | 57.199 | 15.095 | 1.00 | 39.43 | N |
| ATOM | 1913 | CA | GLU | B | 62 | −4.681 | 56.964 | 14.425 | 1.00 | 39.86 | C |
| ATOM | 1915 | CB | GLU | B | 62 | −4.654 | 57.519 | 12.989 | 1.00 | 40.36 | C |
| ATOM | 1918 | CG | GLU | B | 62 | −4.193 | 56.792 | 12.921 | 1.00 | 43.88 | C |
| ATOM | 1921 | CD | GLU | B | 62 | −4.502 | 59.041 | 11.507 | 1.00 | 39.57 | C |
| ATOM | 1922 | OE1 | GLU | B | 62 | −3.969 | 58.931 | 10.608 | 1.00 | 46.84 | O |
| ATOM | 1923 | OE2 | GLU | B | 62 | −4.996 | 60.747 | 11.304 | 1.00 | 46.54 | O |
| ATOM | 1924 | C | GLU | B | 62 | −5.081 | 55.485 | 14.393 | 1.00 | 39.49 | C |
| ATOM | 1925 | O | GLU | B | 62 | −6.267 | 55.175 | 14.403 | 1.00 | 40.45 | O |
| ATOM | 1927 | N | THR | B | 63 | −4.107 | 54.587 | 14.348 | 1.00 | 38.82 | N |
| ATOM | 1928 | CA | THR | B | 63 | −4.376 | 53.157 | 14.130 | 1.00 | 37.60 | C |
| ATOM | 1930 | CB | THR | B | 63 | −3.543 | 52.594 | 12.963 | 1.00 | 36.96 | C |
| ATOM | 1932 | OG1 | THR | B | 63 | −2.153 | 52.664 | 13.280 | 1.00 | 36.39 | O |
| ATOM | 1934 | CG2 | THR | B | 63 | −3.787 | 53.361 | 11.702 | 1.00 | 38.01 | C |

TABLE 2-continued

| ATOM | 1938 | C | THR | B | 63 | -4.100 | 52.273 | 15.354 | 1.00 | 38.28 | C |
|---|---|---|---|---|---|---|---|---|---|---|---|
| ATOM | 1939 | O | THR | B | 63 | -4.449 | 51.098 | 15.363 | 1.00 | 38.81 | O |
| ATOM | 1941 | N | GLY | B | 64 | -3.474 | 52.839 | 16.374 | 1.00 | 38.64 | N |
| ATOM | 1942 | CA | GLY | B | 64 | -3.023 | 52.069 | 17.523 | 1.00 | 38.09 | C |
| ATOM | 1945 | C | GLY | B | 64 | -1.785 | 51.233 | 17.280 | 1.00 | 36.88 | C |
| ATOM | 1946 | O | GLY | B | 64 | -1.449 | 50.395 | 18.101 | 1.00 | 37.46 | O |
| ATOM | 1948 | N | ASP | B | 65 | -1.082 | 51.489 | 16.181 | 1.00 | 36.60 | N |
| ATOM | 1949 | CA | ASP | B | 65 | 0.090 | 50.720 | 15.798 | 1.00 | 35.84 | C |
| ATOM | 1951 | CB | ASP | B | 65 | 0.339 | 50.888 | 14.285 | 1.00 | 35.17 | C |
| ATOM | 1954 | CG | ASP | B | 65 | 1.019 | 49.720 | 13.649 | 1.00 | 33.91 | C |
| ATOM | 1955 | OD1 | ASP | B | 65 | 1.467 | 48.788 | 14.346 | 1.00 | 33.84 | O |
| ATOM | 1956 | OD2 | ASP | B | 65 | 1.160 | 49.771 | 12.414 | 1.00 | 35.29 | O |
| ATOM | 1957 | C | ASP | B | 65 | 1.309 | 51.172 | 16.616 | 1.00 | 34.37 | C |
| ATOM | 1958 | O | ASP | B | 65 | 1.243 | 52.127 | 17.377 | 1.00 | 34.97 | O |
| ATOM | 1960 | N | ASN | B | 66 | 2.439 | 50.508 | 16.426 | 1.00 | 34.27 | N |
| ATOM | 1961 | CA | ASN | B | 66 | 3.674 | 50.720 | 17.197 | 1.00 | 34.46 | C |
| ATOM | 1963 | CB | ASN | B | 66 | 3.788 | 49.669 | 18.316 | 1.00 | 33.14 | C |
| ATOM | 1966 | CG | ASN | B | 66 | 4.026 | 48.228 | 17.796 | 1.00 | 32.28 | C |
| ATOM | 1967 | OD1 | ASN | B | 66 | 3.637 | 47.883 | 16.684 | 1.00 | 33.18 | O |
| ATOM | 1968 | ND2 | ASN | B | 66 | 4.648 | 47.405 | 18.608 | 1.00 | 31.47 | N |
| ATOM | 1971 | C | ASN | B | 66 | 4.914 | 50.703 | 16.291 | 1.00 | 32.92 | C |
| ATOM | 1972 | O | ASN | B | 66 | 5.989 | 50.226 | 16.677 | 1.00 | 33.42 | O |
| ATOM | 1974 | N | VAL | B | 67 | 4.778 | 51.202 | 15.075 | 1.00 | 33.90 | N |
| ATOM | 1975 | CA | VAL | B | 67 | 5.878 | 51.171 | 14.120 | 1.00 | 35.47 | C |
| ATOM | 1977 | CB | VAL | B | 67 | 5.419 | 50.899 | 12.633 | 1.00 | 36.22 | C |
| ATOM | 1979 | CG1 | VAL | B | 67 | 4.812 | 49.482 | 12.535 | 1.00 | 35.93 | C |
| ATOM | 1983 | CG2 | VAL | B | 67 | 4.499 | 52.001 | 12.097 | 1.00 | 36.13 | C |
| ATOM | 1987 | C | VAL | B | 67 | 6.752 | 52.389 | 14.203 | 1.00 | 35.34 | C |
| ATOM | 1988 | O | VAL | B | 67 | 6.355 | 53.431 | 14.659 | 1.00 | 35.03 | O |
| ATOM | 1990 | N | GLY | B | 68 | 7.977 | 52.228 | 13.775 | 1.00 | 33.48 | N |
| ATOM | 1991 | CA | GLY | B | 68 | 8.967 | 53.280 | 13.839 | 1.00 | 34.36 | C |
| ATOM | 1994 | C | GLY | B | 68 | 10.067 | 53.056 | 12.846 | 1.00 | 35.04 | C |
| ATOM | 1995 | O | GLY | B | 68 | 10.129 | 51.974 | 12.254 | 1.00 | 37.39 | O |
| ATOM | 1997 | N | PRO | B | 69 | 10.965 | 54.048 | 12.694 | 1.00 | 36.38 | N |
| ATOM | 1998 | CA | PRO | B | 69 | 12.120 | 53.993 | 11.772 | 1.00 | 35.65 | C |
| ATOM | 2000 | CB | PRO | B | 69 | 12.597 | 55.459 | 11.736 | 1.00 | 38.08 | C |
| ATOM | 2003 | CG | PRO | B | 69 | 12.206 | 56.000 | 13.061 | 1.00 | 37.66 | C |
| ATOM | 2006 | CD | PRO | B | 69 | 10.863 | 55.367 | 13.353 | 1.00 | 37.45 | C |
| ATOM | 2009 | C | PRO | B | 69 | 13.284 | 53.050 | 12.072 | 1.00 | 35.38 | C |
| ATOM | 2010 | O | PRO | B | 69 | 13.371 | 52.406 | 13.109 | 1.00 | 34.63 | O |
| ATOM | 2011 | N | LEU | B | 70 | 14.092 | 52.905 | 11.032 | 1.00 | 33.74 | N |
| ATOM | 2012 | CA | LEU | B | 70 | 15.391 | 52.282 | 11.065 | 1.00 | 35.82 | C |
| ATOM | 2014 | CB | LEU | B | 70 | 15.499 | 51.262 | 9.938 | 1.00 | 36.22 | C |
| ATOM | 2017 | CG | LEU | B | 70 | 16.876 | 50.597 | 9.810 | 1.00 | 38.51 | C |
| ATOM | 2019 | CD1 | LEU | B | 70 | 17.156 | 49.547 | 10.882 | 1.00 | 39.36 | C |
| ATOM | 2023 | CD2 | LEU | B | 70 | 17.029 | 49.986 | 8.451 | 1.00 | 40.05 | C |
| ATOM | 2027 | C | LEU | B | 70 | 16.485 | 53.343 | 10.906 | 1.00 | 36.26 | C |
| ATOM | 2028 | O | LEU | B | 70 | 16.564 | 54.106 | 9.921 | 1.00 | 35.02 | O |
| ATOM | 2030 | N | ILE | B | 71 | 17.367 | 53.346 | 11.899 | 1.00 | 33.45 | N |

TABLE 2-continued

| | | | | | | | | |
|---|---|---|---|---|---|---|---|---|
| ATOM | 2031 | CA | ILE | B | 71 | 18.534 | 54.241 | 11.961 | 1.00 | 36.48 | C |
| ATOM | 2033 | CB | ILE | B | 71 | 18.652 | 54.918 | 13.343 | 1.00 | 36.69 | C |
| ATOM | 2035 | CG1 | ILE | B | 71 | 17.318 | 55.598 | 13.688 | 1.00 | 36.91 | C |
| ATOM | 2038 | CD1 | ILE | B | 71 | 17.171 | 56.022 | 15.151 | 1.00 | 38.97 | C |
| ATOM | 2042 | CG2 | ILE | B | 71 | 19.753 | 55.936 | 13.326 | 1.00 | 34.23 | C |
| ATOM | 2046 | C | ILE | B | 71 | 19.832 | 53.548 | 11.600 | 1.00 | 36.20 | C |
| ATOM | 2047 | O | ILE | B | 71 | 20.274 | 52.556 | 12.230 | 1.00 | 33.44 | O |
| ATOM | 2049 | N | ILE | B | 72 | 20.489 | 54.123 | 10.599 | 1.00 | 37.18 | N |
| ATOM | 2050 | CA | ILE | B | 72 | 21.860 | 53.753 | 10.263 | 1.00 | 36.48 | C |
| ATOM | 2052 | CB | ILE | B | 72 | 22.042 | 53.334 | 8.771 | 1.00 | 36.48 | C |
| ATOM | 2054 | CG1 | ILE | B | 72 | 21.042 | 52.249 | 8.373 | 1.00 | 41.51 | C |
| ATOM | 2057 | CD1 | ILE | B | 72 | 21.131 | 50.989 | 9.178 | 1.00 | 36.18 | C |
| ATOM | 2061 | CG2 | ILE | B | 72 | 23.458 | 52.846 | 8.510 | 1.00 | 37.20 | C |
| ATOM | 2065 | C | ILE | B | 72 | 22.777 | 54.932 | 10.565 | 1.00 | 38.38 | C |
| ATOM | 2066 | O | ILE | B | 72 | 22.575 | 56.034 | 10.057 | 1.00 | 37.97 | O |
| ATOM | 2068 | N | LYS | B | 73 | 23.796 | 54.690 | 11.379 | 1.00 | 40.32 | N |
| ATOM | 2069 | CA | LYS | B | 73 | 24.714 | 55.749 | 11.809 | 1.00 | 43.20 | C |
| ATOM | 2071 | CB | LYS | B | 73 | 24.317 | 56.271 | 13.193 | 1.00 | 43.38 | C |
| ATOM | 2074 | CG | LYS | B | 73 | 23.913 | 55.178 | 14.173 | 1.00 | 45.66 | C |
| ATOM | 2077 | CD | LYS | B | 73 | 23.873 | 55.696 | 15.599 | 1.00 | 45.43 | C |
| ATOM | 2080 | CE | LYS | B | 73 | 23.082 | 54.758 | 16.508 | 1.00 | 47.74 | C |
| ATOM | 2083 | NZ | LYS | B | 73 | 23.608 | 53.356 | 16.499 | 1.00 | 50.89 | N |
| ATOM | 2087 | C | LYS | B | 73 | 26.146 | 55.283 | 11.854 | 1.00 | 42.89 | C |
| ATOM | 2088 | O | LYS | B | 73 | 26.420 | 54.093 | 11.841 | 1.00 | 43.11 | O |
| ATOM | 2090 | N | LYS | B | 74 | 27.057 | 56.250 | 11.898 | 1.00 | 44.01 | N |
| ATOM | 2091 | CA | LYS | B | 74 | 28.462 | 55.993 | 12.185 | 1.00 | 44.68 | C |
| ATOM | 2093 | CB | LYS | B | 74 | 29.337 | 57.114 | 11.618 | 1.00 | 44.34 | C |
| ATOM | 2096 | CG | LYS | B | 74 | 29.248 | 57.285 | 10.115 | 1.00 | 42.46 | C |
| ATOM | 2099 | CD | LYS | B | 74 | 30.219 | 58.348 | 9.621 | 1.00 | 43.81 | C |
| ATOM | 2104 | C | LYS | B | 74 | 28.634 | 55.890 | 13.708 | 1.00 | 45.87 | C |
| ATOM | 2105 | O | LYS | B | 74 | 28.056 | 56.683 | 14.454 | 1.00 | 45.76 | O |
| ATOM | 2107 | N | LYS | B | 75 | 29.419 | 54.912 | 14.160 | 1.00 | 47.74 | N |
| ATOM | 2108 | CA | LYS | B | 75 | 29.670 | 54.706 | 15.593 | 1.00 | 49.25 | C |
| ATOM | 2110 | CB | LYS | B | 75 | 30.731 | 53.618 | 15.812 | 1.00 | 49.40 | C |
| ATOM | 2113 | CG | LYS | B | 75 | 30.900 | 53.186 | 17.262 | 1.00 | 48.44 | C |
| ATOM | 2119 | C | LYS | B | 75 | 30.090 | 55.998 | 16.306 | 1.00 | 50.80 | C |
| ATOM | 2120 | O | LYS | B | 75 | 29.611 | 56.276 | 17.408 | 1.00 | 51.73 | O |
| ATOM | 2122 | N | GLU | B | 76 | 30.969 | 56.782 | 15.677 | 1.00 | 51.99 | N |
| ATOM | 2123 | CA | GLU | B | 76 | 31.420 | 58.059 | 16.246 | 1.00 | 52.71 | C |
| ATOM | 2125 | CB | GLU | B | 76 | 32.920 | 58.263 | 16.016 | 1.00 | 52.99 | C |
| ATOM | 2128 | CG | GLU | B | 76 | 33.821 | 57.094 | 16.437 | 1.00 | 54.35 | C |
| ATOM | 2131 | CD | GLU | B | 76 | 34.115 | 57.040 | 17.936 | 1.00 | 55.11 | C |
| ATOM | 2132 | OE1 | GLU | B | 76 | 33.215 | 57.328 | 18.762 | 1.00 | 54.35 | O |
| ATOM | 2133 | OE2 | GLU | B | 76 | 35.261 | 56.685 | 18.287 | 1.00 | 56.76 | O |
| ATOM | 2134 | C | GLU | B | 76 | 30.644 | 59.233 | 15.641 | 1.00 | 52.94 | C |
| ATOM | 2135 | O | GLU | B | 76 | 29.642 | 59.692 | 16.198 | 1.00 | 52.78 | O |
| ATOM | 2137 | S2 | FES | B | 500 | 8.762 | 55.437 | 10.029 | 1.00 | 34.71 | S |
| ATOM | 2138 | FE2 | FES | B | 500 | 8.999 | 57.535 | 10.406 | 1.00 | 37.57 | FE |
| ATOM | 2139 | S1 | FES | B | 500 | 7.885 | 58.358 | 8.740 | 1.00 | 35.48 | S |

TABLE 2-continued

| ATOM | | FE1 | FES | B | | | | | | | FE |
|------|------|-----|-----|---|---|---|---|---|---|---|---|
| ATOM | 2140 | O | | | 500 | | 7.643 | 56.280 | 8.420 | 1.00 | 35.15 | O |
| ATOM | 2141 | O | HOH | | 1 | | 12.827 | 53.083 | 3.967 | 1.00 | 20.66 | O |
| ATOM | 2144 | O | HOH | | 2 | | 13.751 | 46.765 | 9.481 | 1.00 | 24.03 | O |
| ATOM | 2147 | O | HOH | | 3 | | 11.217 | 50.377 | 23.088 | 1.00 | 28.20 | O |
| ATOM | 2150 | O | HOH | | 4 | | −0.125 | 48.163 | 18.303 | 1.00 | 29.90 | O |
| ATOM | 2153 | O | HOH | | 5 | | 3.037 | 41.536 | 11.986 | 1.00 | 27.75 | O |
| ATOM | 2156 | O | HOH | | 6 | | 11.894 | 50.634 | 19.913 | 1.00 | 24.14 | O |
| ATOM | 2159 | O | HOH | | 7 | | 1.011 | 59.304 | 8.936 | 1.00 | 31.87 | O |
| ATOM | 2162 | O | HOH | | 8 | | 3.821 | 40.851 | 19.924 | 1.00 | 32.89 | O |
| ATOM | 2165 | O | HOH | | 9 | | 1.249 | 55.261 | 1.544 | 1.00 | 32.57 | O |
| ATOM | 2168 | O | HOH | | 10 | | 20.339 | 56.989 | 2.276 | 1.00 | 33.39 | O |
| ATOM | 2171 | O | HOH | | 11 | | 10.916 | 45.880 | −8.374 | 1.00 | 32.49 | O |
| ATOM | 2174 | O | HOH | | 12 | | 10.044 | 52.985 | 21.964 | 1.00 | 28.72 | O |
| ATOM | 2177 | O | HOH | | 13 | | 4.434 | 56.746 | 17.961 | 1.00 | 27.96 | O |
| ATOM | 2180 | O | HOH | | 14 | | 12.825 | 52.101 | −5.323 | 1.00 | 32.98 | O |
| ATOM | 2183 | O | HOH | | 15 | | 4.215 | 55.194 | 20.142 | 1.00 | 33.31 | O |
| ATOM | 2186 | O | HOH | | 16 | | 3.354 | 62.470 | 12.595 | 1.00 | 32.61 | O |
| ATOM | 2189 | O | HOH | | 17 | | 24.115 | 54.994 | −2.105 | 1.00 | 36.40 | O |
| ATOM | 2192 | O | HOH | | 18 | | 13.167 | 47.854 | 18.798 | 1.00 | 31.78 | O |
| ATOM | 2195 | O | HOH | | 19 | | 2.785 | 48.423 | −10.440 | 1.00 | 36.93 | O |
| ATOM | 2198 | O | HOH | | 20 | | 1.929 | 58.106 | 18.115 | 1.00 | 34.83 | O |
| ATOM | 2201 | O | HOH | | 21 | | 3.865 | 37.769 | 4.633 | 1.00 | 33.71 | O |
| ATOM | 2204 | O | HOH | | 22 | | −0.207 | 48.162 | −4.885 | 1.00 | 32.54 | O |
| ATOM | 2207 | O | HOH | | 23 | | 15.042 | 44.124 | −6.558 | 1.00 | 34.06 | O |
| ATOM | 2210 | O | HOH | | 24 | | 8.742 | 34.431 | 6.738 | 1.00 | 41.86 | O |
| ATOM | 2213 | O | HOH | | 25 | | −0.027 | 53.383 | 19.456 | 1.00 | 32.96 | O |
| ATOM | 2216 | O | HOH | | 26 | | 6.513 | 40.877 | −4.338 | 1.00 | 32.06 | O |
| ATOM | 2219 | O | HOH | | 27 | | 1.234 | 47.979 | 20.568 | 1.00 | 35.39 | O |
| ATOM | 2222 | O | HOH | | 28 | | 15.196 | 43.491 | 17.691 | 1.00 | 50.26 | O |
| ATOM | 2225 | O | HOH | | 29 | | 3.066 | 48.492 | 23.841 | 1.00 | 31.98 | O |
| ATOM | 2228 | O | HOH | | 30 | | 10.065 | 43.535 | −9.211 | 1.00 | 37.84 | O |
| ATOM | 2231 | O | HOH | | 31 | | 9.531 | 38.785 | 13.609 | 1.00 | 38.76 | O |
| ATOM | 2234 | O | HOH | | 32 | | 0.208 | 40.733 | 5.045 | 1.00 | 39.05 | O |
| ATOM | 2237 | O | HOH | | 33 | | 20.353 | 41.097 | 6.217 | 1.00 | 33.65 | O |
| ATOM | 2240 | O | HOH | | 34 | | 2.645 | 39.079 | 10.633 | 1.00 | 38.09 | O |
| ATOM | 2243 | O | HOH | | 35 | | 6.225 | 58.782 | 17.692 | 1.00 | 43.18 | O |
| ATOM | 2246 | O | HOH | | 36 | | 1.962 | 52.255 | 20.641 | 1.00 | 41.61 | O |
| ATOM | 2249 | O | HOH | | 37 | | 2.952 | 44.710 | −7.282 | 1.00 | 40.92 | O |
| ATOM | 2252 | O | HOH | | 38 | | −2.021 | 55.254 | 8.560 | 1.00 | 34.28 | O |
| ATOM | 2255 | O | HOH | | 39 | | 1.301 | 38.320 | 4.597 | 1.00 | 41.53 | O |
| ATOM | 2258 | O | HOH | | 40 | | 25.148 | 48.504 | 15.664 | 1.00 | 38.64 | O |
| ATOM | 2261 | O | HOH | | 41 | | 5.678 | 58.075 | −5.012 | 1.00 | 44.93 | O |
| ATOM | 2264 | O | HOH | | 42 | | 10.278 | 56.067 | −2.925 | 1.00 | 43.32 | O |
| ATOM | 2267 | O | HOH | | 43 | | 7.429 | 39.548 | 18.295 | 1.00 | 44.04 | O |
| ATOM | 2270 | O | HOH | | 44 | | 22.928 | 48.419 | 17.076 | 1.00 | 41.30 | O |
| ATOM | 2273 | O | HOH | | 45 | | 1.933 | 56.360 | −6.737 | 1.00 | 40.64 | O |
| ATOM | 2276 | O | HOH | | 46 | | 1.321 | 49.877 | 22.378 | 1.00 | 39.04 | O |
| ATOM | 2279 | O | HOH | | 47 | | −1.406 | 58.295 | 9.007 | 1.00 | 41.99 | O |
| ATOM | 2282 | O | HOH | | 48 | | 16.137 | 43.177 | −3.994 | 1.00 | 45.32 | O |

TABLE 2-continued

| | | | | | | | | |
|---|---|---|---|---|---|---|---|---|
| ATOM | 2285 | O | HOH | 49 | 22.244 | 45.120 | 11.028 | 1.00 | 44.12 | O |
| ATOM | 2288 | O | HOH | 50 | −3.099 | 51.981 | 7.539 | 1.00 | 45.61 | O |
| ATOM | 2291 | O | HOH | 51 | 0.319 | 57.592 | 2.798 | 1.00 | 46.50 | O |
| ATOM | 2294 | O | HOH | 52 | 22.211 | 53.760 | −3.975 | 1.00 | 40.02 | O |
| ATOM | 2297 | O | HOH | 53 | −2.586 | 50.464 | 20.614 | 1.00 | 45.05 | O |
| ATOM | 2300 | O | HOH | 54 | 1.461 | 62.243 | 19.193 | 1.00 | 48.75 | O |
| ATOM | 2303 | O | HOH | 55 | −4.088 | 55.169 | 19.223 | 1.00 | 45.39 | O |
| ATOM | 2306 | O | HOH | 56 | 29.385 | 57.097 | 5.738 | 1.00 | 50.82 | O |
| ATOM | 2309 | O | HOH | 57 | 6.627 | 35.638 | 7.976 | 1.00 | 43.91 | O |
| ATOM | 2312 | O | HOH | 58 | 27.329 | 46.625 | −3.502 | 1.00 | 40.59 | O |
| ATOM | 2315 | O | HOH | 59 | 12.618 | 33.337 | 8.275 | 1.00 | 43.96 | O |
| ATOM | 2318 | O | HOH | 60 | 7.929 | 65.728 | 4.980 | 1.00 | 42.47 | O |
| ATOM | 2321 | O | HOH | 61 | 18.899 | 43.654 | −4.591 | 1.00 | 46.61 | O |
| ATOM | 2324 | O | HOH | 62 | 21.109 | 45.542 | −4.017 | 1.00 | 44.42 | O |
| ATOM | 2327 | O | HOH | 63 | 1.116 | 40.565 | 20.202 | 1.00 | 49.60 | O |
| ATOM | 2330 | O | HOH | 64 | 13.441 | 42.093 | −2.644 | 1.00 | 51.70 | O |
| ATOM | 2333 | O | HOH | 65 | −1.961 | 45.883 | 19.055 | 1.00 | 45.53 | O |
| ATOM | 2336 | O | HOH | 66 | 6.663 | 59.881 | 0.010 | 1.00 | 38.90 | O |
| ATOM | 2339 | O | HOH | 67 | 5.470 | 37.900 | 11.677 | 1.00 | 52.16 | O |
| ATOM | 2342 | O | HOH | 68 | 2.129 | 63.382 | 10.463 | 1.00 | 43.69 | O |
| ATOM | 2345 | O | HOH | 69 | 4.631 | 63.862 | 6.532 | 1.00 | 43.19 | O |
| ATOM | 2348 | O | HOH | 70 | 1.423 | 59.836 | 3.776 | 1.00 | 51.60 | O |
| ATOM | 2351 | O | HOH | 71 | 1.262 | 48.684 | −7.220 | 1.00 | 42.71 | O |
| ATOM | 2354 | O | HOH | 72 | 2.743 | 62.077 | 5.826 | 1.00 | 42.20 | O |
| ATOM | 2357 | O | HOH | 73 | 18.159 | 39.629 | 5.870 | 1.00 | 43.02 | O |
| ATOM | 2360 | O | HOH | 74 | −1.455 | 45.237 | 21.811 | 1.00 | 60.31 | O |
| ATOM | 2363 | O | HOH | 75 | −5.136 | 62.639 | 13.206 | 1.00 | 50.74 | O |
| ATOM | 2366 | O | HOH | 76 | −1.543 | 46.932 | 6.875 | 1.00 | 50.10 | O |
| ATOM | 2369 | O | HOH | 77 | 1.131 | 61.900 | 8.098 | 1.00 | 47.72 | O |
| ATOM | 2372 | O | HOH | 78 | −2.780 | 42.279 | 15.253 | 1.00 | 47.50 | O |
| ATOM | 2375 | O | HOH | 79 | 15.893 | 41.893 | −1.684 | 1.00 | 55.32 | O |
| ATOM | 2378 | O | HOH | 80 | 9.747 | 34.076 | 3.642 | 1.00 | 47.75 | O |
| ATOM | 2381 | O | HOH | 81 | 13.278 | 42.107 | −7.599 | 1.00 | 53.59 | O |
| ATOM | 2384 | O | HOH | 82 | 21.410 | 59.057 | 3.348 | 1.00 | 45.21 | O |
| ATOM | 2387 | O | HOH | 83 | −6.107 | 44.886 | −0.556 | 1.00 | 54.30 | O |
| ATOM | 2390 | O | HOH | 84 | 5.988 | 55.914 | 22.195 | 1.00 | 48.14 | O |
| ATOM | 2393 | O | HON | 85 | 5.812 | 42.531 | −6.733 | 1.00 | 45.63 | O |
| ATOM | 2396 | O | HOH | 86 | 1.529 | 42.804 | −5.810 | 1.00 | 41.29 | O |
| ATOM | 2399 | O | HOH | 87 | 17.605 | 60.778 | 7.008 | 1.00 | 47.01 | O |
| ATOM | 2402 | O | HOH | 88 | 24.596 | 49.804 | −6.280 | 1.00 | 47.01 | O |
| ATOM | 2405 | O | HOH | 89 | 13.151 | 56.441 | −4.353 | 1.00 | 44.41 | O |
| ATOM | 2408 | O | HOH | 90 | 5.821 | 39.505 | 21.085 | 1.00 | 43.73 | O |
| ATOM | 2411 | O | HDH | 91 | −1.670 | 59.427 | 6.577 | 1.00 | 68.02 | O |
| ATOM | 2414 | O | HOH | 92 | −0.225 | 42.826 | 22.727 | 1.00 | 53.61 | O |
| ATOM | 2417 | O | HOH | 93 | −6.850 | 49.974 | 13.682 | 1.00 | 51.83 | O |
| ATOM | 2420 | O | HOH | 94 | −4.049 | 45.731 | 9.545 | 1.00 | 47.13 | O |
| ATOM | 2423 | O | HOH | 95 | 0.452 | 56.494 | 19.458 | 1.00 | 50.23 | O |
| ATOM | 2426 | O | HOH | 96 | 16.576 | 39.054 | 13.722 | 1.00 | 44.12 | O |
| ATOM | 2429 | O | HOH | 97 | 1.943 | 59.729 | −4.492 | 1.00 | 59.80 | O |

TABLE 2-continued

| | | | | | | | |
|---|---|---|---|---|---|---|---|
| ATOM | 2432 | O | HOH | 98 | 7.583 | 40.933 | 22.752 | 1.00 | 50.60 | O |
| ATOM | 2435 | O | HOH | 99 | 27.822 | 50.054 | −5.559 | 1.00 | 52.06 | O |
| ATOM | 2438 | O | HOH | 100 | 23.113 | 43.501 | −3.154 | 1.00 | 48.71 | O |
| ATOM | 2441 | O | HOH | 101 | −1.272 | 62.753 | 6.804 | 1.00 | 57.98 | O |
| ATOM | 2444 | O | HOH | 102 | 14.964 | 37.745 | 15.201 | 1.00 | 61.18 | O |
| ATOM | 2447 | O | HOH | 103 | 22.848 | 57.467 | −2.041 | 1.00 | 50.70 | O |
| ATOM | 2450 | O | HOH | 104 | −2.158 | 49.758 | 6.394 | 1.00 | 50.98 | O |
| ATOM | 2453 | O | HOH | 105 | 18.443 | 38.205 | 2.713 | 1.00 | 59.59 | O |
| ATOM | 2456 | O | HOH | 106 | 9.942 | 39.861 | 16.305 | 1.00 | 57.42 | O |
| ATOM | 2459 | O | HOH | 107 | 10.212 | 66.742 | 6.158 | 1.00 | 52.93 | O |
| ATOM | 2462 | O | HOH | 108 | −0.453 | 59.776 | −4.378 | 1.00 | 63.12 | O |
| ATOM | 2465 | O | HOH | 109 | 4.784 | 38.967 | −4.606 | 1.00 | 45.48 | O |
| ATOM | 2468 | O | HOH | 110 | 4.845 | 62.486 | −1.196 | 1.00 | 52.43 | O |
| ATOM | 2471 | O | HOH | 111 | 3.293 | 34.297 | −4.307 | 1.00 | 59.56 | O |
| ATOM | 2474 | O | HOH | 112 | −1.816 | 36.819 | 6.123 | 1.00 | 63.66 | O |
| ATOM | 2477 | O | HOH | 113 | 23.349 | 59.853 | 5.467 | 1.00 | 61.43 | O |
| ATOM | 2480 | O | HOH | 114 | 25.946 | 63.690 | 7.329 | 1.00 | 49.02 | O |
| ATOM | 2483 | O | HOH | 115 | 6.794 | 35.373 | 1.151 | 1.00 | 42.87 | O |
| ATOM | 2486 | O | HOH | 116 | −3.027 | 51.555 | −5.581 | 1.00 | 64.82 | O |
| ATOM | 2489 | O | HOH | 117 | 5.434 | 64.425 | 9.645 | 1.00 | 51.59 | O |
| ATOM | 2492 | O | HOH | 118 | 1.808 | 59.998 | 19.956 | 1.00 | 54.80 | O |
| ATOM | 2495 | O | HOH | 119 | −2.135 | 49.372 | −5.934 | 1.00 | 53.29 | O |
| ATOM | 2498 | O | HOH | 120 | 7.215 | 41.632 | 26.993 | 1.00 | 47.19 | O |
| ATOM | 2501 | O | HOH | 121 | 4.399 | 63.984 | 18.343 | 1.00 | 51.32 | O |
| ATOM | 2504 | O | HOH | 122 | 13.022 | 61.573 | −0.299 | 1.00 | 56.08 | O |
| ATOM | 2507 | O | HOH | 123 | 15.264 | 60.159 | −2.151 | 1.00 | 48.88 | O |
| ATOM | 2510 | O | HOH | 124 | 15.302 | 38.381 | 1.627 | 1.00 | 57.94 | O |
| ATOM | 2513 | O | HOH | 125 | 33.103 | 49.100 | −0.660 | 1.00 | 55.70 | O |
| ATOM | 2516 | O | HOH | 126 | 3.505 | 34.230 | −2.002 | 1.00 | 52.44 | O |
| ATOM | 2519 | O | HOH | 127 | 7.046 | 62.558 | 14.896 | 1.00 | 59.75 | O |
| ATOM | 2522 | O | HOH | 128 | 5.090 | 56.116 | −13.896 | 1.00 | 44.44 | O |
| ATOM | 2525 | O | HOH | 129 | 24.988 | 60.298 | 14.018 | 1.00 | 49.56 | O |
| ATOM | 2528 | O | HOH | 130 | 18.973 | 62.120 | 9.038 | 1.00 | 63.28 | O |
| ATOM | 2531 | O | HOH | 131 | 10.213 | 34.654 | −2.687 | 1.00 | 60.00 | O |
| ATOM | 2534 | O | HOH | 132 | 10.807 | 33.563 | 0.220 | 1.00 | 62.07 | O |
| ATOM | 2537 | O | HOH | 133 | 7.830 | 41.976 | −8.540 | 1.00 | 53.55 | O |
| ATOM | 2540 | O | HOH | 134 | 32.254 | 58.413 | 0.423 | 1.00 | 55.74 | O |
| ATOM | 2543 | O | HOH | 135 | 29.562 | 40.531 | 5.495 | 1.00 | 58.95 | O |
| END | | | | | | | | | | |

What is claimed is:

1. An isolated crystal comprising a human mitoNEET protein comprising the amino acid sequence as set forth in SEQ ID NO: 1, wherein said crystal has an orthorhombic space group P212121 and unit cell dimensions of a=46.8 Å, b=49.6 Å, and c=59.0 Å.

2. The crystal of claim 1, having a three dimensional structure characterized by the atomic coordinates of Table 2.

3. The crystal of claim 1, wherein said human mitoNEET protein has tertiary structure comprising a NEET fold.

4. The crystal of claim 1, wherein said human mitoNEET protein is truncated.

* * * * *